(12) United States Patent
Curnow et al.

(10) Patent No.: US 9,346,758 B2
(45) Date of Patent: May 24, 2016

(54) PYRIDINONE COMPOUNDS FOR USE IN PHOTODYNAMIC THERAPY

(71) Applicant: UNIVERSITY OF EXETER, Exeter (GB)

(72) Inventors: Alison Curnow, Cornwall (GB); Mark Wood, Exeter (GB); Alexis Perry, Exeter (GB)

(73) Assignee: UNIVERSITY OF EXETER, Exeter (GB)

( * ) Notice: Subject to any disclaimer, the term of this patent is extended or adjusted under 35 U.S.C. 154(b) by 0 days.

(21) Appl. No.: 14/425,385

(22) PCT Filed: Sep. 2, 2013

(86) PCT No.: PCT/GB2013/052297
§ 371 (c)(1),
(2) Date: Mar. 3, 2015

(87) PCT Pub. No.: WO2014/033477
PCT Pub. Date: Mar. 6, 2014

(65) Prior Publication Data
US 2015/0210642 A1    Jul. 30, 2015

(30) Foreign Application Priority Data
Sep. 3, 2012 (GB) .................................. 1215675.8

(51) Int. Cl.
*C07D 213/69* (2006.01)
*A61K 31/4412* (2006.01)
*A61K 41/00* (2006.01)
*A61K 49/00* (2006.01)
*A61K 8/49* (2006.01)
*A61Q 19/00* (2006.01)

(52) U.S. Cl.
CPC ............ *C07D 213/69* (2013.01); *A61K 8/4926* (2013.01); *A61K 41/0057* (2013.01); *A61K 49/0021* (2013.01); *A61Q 19/00* (2013.01); *A61K 2800/81* (2013.01)

(58) Field of Classification Search
None
See application file for complete search history.

(56) References Cited

U.S. PATENT DOCUMENTS 5,480,894 A    1/1996    Hider et al.

FOREIGN PATENT DOCUMENTS

| GB | 2 269 589 A | 2/1994 |
| WO | 02/10120 A1 | 2/2002 |
| WO | 2014/033477 A1 | 3/2014 |

OTHER PUBLICATIONS

International Search Report for PCT/GB2013/052297 dated Mar. 3, 2015.*

Battah et al., "Synthesis and Biological Studies of 5-Aminolevulinic Acid-Containing Dendrimers for Photodynamic Therapy", Bioconjugate Chem., 2001, pp. 980-988, vol. 12, No. 6.

Bech et al., "A Hydroxypyridinone (CP94) Enhances Protoporphyrin IX Formation in 5-Aminolaevulinic Acid Treated Cells", Journal of Photochemistry and Photobiology B: Biology, 1997, pp. 136-144, vol. 41.

Blake et al., "The Hydroxypyridinone Iron Chelator CP94 Can Enhance PpIX-Induced PDT of Cultured Human Glioma Cells", Photochemistry and Photobiology, 2010, pp. 1154-1160, vol. 86, No. 5.

Blake et al., "An in Vitro Comparison of the Effects of the Iron-Chelating Agents, CP94 and Dexrazoxane, on Protoporphyrin IX Accumulation for Photodynamic Therapy and/or Fluorescence Guided Resection", Photochemistry and Photobiology, 2011, pp. 1419-1426, vol. 87, No. 6.

Curnow et al., "Enhancement of 5-Aminolaevulinic Acid-Induced Photodynamic Therapy in Normal Rat Colon Using Hydroxypyridinone Iron-Chelating Agents", British Journal of Cancer, 1998, pp. 1278-1282, vol. 78, No. 10.

Curnow et al., "Biochemical Manipulation via Iron Chelation to Enhance Porphyrin Production from Porphyrin Precursors", Journal of Environmental Pathology, Toxicology, and Oncology, 2007, pp. 89-103, vol. 26, No. 2.

Dobbin et al., "Synthesis, Physicochemical Properties, and Biological Evaluation of N-Substituted 2-Alkyl-3-hydroxy-4 (1H)-pyridinones: Orally Active Iron Chelators with Clinical Potential", Journal of Medicinal Chemistry, 1993, pp. 2448-2458, vol. 36, No. 17.

Great Britain Search Report from Application No. GB1215675.8, dated Dec. 13, 2012; 5 pgs.

International Preliminary Report on Patentability from related International Application No. PCT/GB2013/052297, dated Mar. 12, 2015; 7 pgs.

International Search Report and Written Opinion from related International Application No. PCT/GB2013/052297, dated Nov. 13, 2013; 9 pgs.

(Continued)

*Primary Examiner* — Zinna Northington Davis

(57) ABSTRACT

A compound which is a compound of formula (I) or any salt thereof: wherein R1 is a Ci-C6 alkyl group, R2 is H or a Ci-C6 alkyl group, R3 is H or a Ci-C6 alkyl group, and n is an integer from 0 to 5.

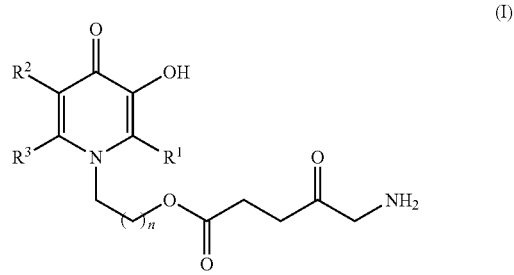

(I)

25 Claims, 31 Drawing Sheets

(56) References Cited

OTHER PUBLICATIONS

Liu et al., "Synthesis, Physicochemical Properties and Biological Evaluation of Aromatic Ester Prodrugs of 1-(2'-Hydroxyethyl)-2-ethyl-3-hydroxypyridin-4-one (CP102): Orally Active Iron Chelators with Clinical Potential", J. Pharm. Pharmacol., 1999, pp. 555-564, vol. 51.

Neuberger et al., "Synthesis and Metabolism of some Substances Related to δ-Aminolaevulic Acid", Biochem J., 1956, pp. 137-145, vol. 64.

Piyamongkol et al., "Design and Characterisation of Novel Hexadentate 3-hydroxypyridin-4-one Ligands", Tetrahedron Letters, 2005, pp. 1333-1336, vol. 46.

Pye et al., "Direct Comparison of δ-Aminolevulinic Acid and Methyl-Aminolevulinate-Derived Protoporphyrin IX Accumulations Potentiated by Desferrioxamine or the Novel Hydroxypyridinone Iron Chelator CP94 in Cultured Human Cells", Photochemistry and Photobiology, 2007, pp. 766-773, vol. 83, No. 3.

Pye et al., "Enhancement of Methyl-Aminolevulinate Photodynamic Therapy by Iron Chelation with CP94: an in vitro Investigation and Clinical Dose-Escalating Safety Study for the Treatment of Nodular Basal Cell Carcinoma", J Cancer Res Clin Oncol, 2008, pp. 841-849, vol. 134, No. 8.

Rai et al., "Synthesis, Physicochemical Properties and Biological Evaluation of Ester Prodrugs of 3-hydroxypyridin-4-ones: Design of Orally Active Chelators with Clinical Potential", Eur. J. Med. Chem., 1999, pp. 475-485, vol. 34, No. 6.

* cited by examiner

| AP2-18 (250 µM) vs | Time (hours) | | | | | | |
|---|---|---|---|---|---|---|---|
| | 0 | 1 | 2 | 3 | 4 | 5 | 6 |
| ALA (250 µM) | n.s | n.s | P<0.05 | P<0.001 | P<0.001 | P<0.001 | P<0.001 |
| ALA (500 µM) | n.s | n.s | n.s | P<0.01 | P<0.001 | P<0.001 | P<0.001 |
| ALA (1000 µM) | n.s | n.s | n.s | P<0.05 | P<0.01 | P<0.001 | P<0.001 |
| ALA (250 µM) + CP94 (250 µM) | n.s | n.s | n.s | n.s | n.s | n.s | n.s |
| ALA (500 µM) + CP94 (500 µM) | n.s | n.s | n.s | n.s | n.s | n.s | P<0.05 |
| ALA (1000 µM) + CP94 (1000 µM) | n.s | n.s | n.s | n.s | n.s | n.s | n.s |
| MAL (250 µM) | n.s | n.s | P<0.001 | P<0.001 | P<0.001 | P<0.001 | P<0.001 |
| MAL (500 µM) | n.s | n.s | P<0.001 | P<0.001 | P<0.001 | P<0.001 | P<0.001 |
| MAL (1000 µM) | n.s | n.s | n.s | n.s | n.s | P<0.05 | P<0.01 |
| MAL (250 µM) + CP94 (250 µM) | P<0.001 | n.s | n.s | n.s | P<0.001 | P<0.001 | P<0.001 |
| MAL (500 µM) + CP94 (500 µM) | P<0.001 | n.s | n.s | n.s | P<0.05 | P<0.01 | P<0.001 |
| MAL (1000 µM) + CP94 (1000 µM) | n.s | n.s | n.s | n.s | n.s | n.s | n.s |
| AP-18 (250 µM) | | | | | | | |
| AP-18 (500 µM) | n.s | n.s | n.s | n.s | n.s | n.s | n.s |
| AP-18 (1000 µM) | n.s | n.s | P<0.01 | P<0.001 | P<0.001 | P<0.001 | P<0.001 |

| AP2-18 (500 µM) vs | Time (hours) | | | | | | |
|---|---|---|---|---|---|---|---|
| | 0 | 1 | 2 | 3 | 4 | 5 | 6 |
| ALA (250 µM) | n.s | n.s | P<0.001 | P<0.001 | P<0.001 | P<0.001 | P<0.001 |
| ALA (500 µM) | n.s | P<0.05 | P<0.001 | P<0.001 | P<0.001 | P<0.001 | P<0.001 |
| ALA (1000 µM) | n.s | n.s | P<0.01 | P<0.001 | P<0.001 | P<0.001 | P<0.001 |
| ALA (250 µM) + CP94 (250 µM) | n.s | n.s | n.s | n.s | n.s | n.s | n.s |
| ALA (500 µM) + CP94 (500 µM) | n.s | n.s | n.s | n.s | n.s | n.s | n.s |
| ALA (1000 µM) + CP94 (1000 µM) | n.s | n.s | n.s | n.s | n.s | n.s | P<0.05 |
| MAL (250 µM) | n.s | P<0.05 | P<0.001 | P<0.001 | P<0.001 | P<0.001 | P<0.001 |
| MAL (500 µM) | n.s | P<0.05 | P<0.001 | P<0.001 | P<0.001 | P<0.001 | P<0.001 |
| MAL (1000 µM) | n.s | n.s | P<0.05 | P<0.01 | P<0.001 | P<0.001 | P<0.001 |
| MAL (250 µM) + CP94 (250 µM) | P<0.001 | n.s | P<0.05 | P<0.001 | P<0.001 | P<0.001 | P<0.001 |
| MAL (500 µM) + CP94 (500 µM) | P<0.001 | n.s | n.s | P<0.01 | P<0.001 | P<0.001 | P<0.001 |
| MAL (1000 µM) + CP94 (1000 µM) | n.s | n.s | n.s | n.s | n.s | n.s | P<0.05 |
| AP-18 (250 µM) | n.s | n.s | n.s | n.s | n.s | n.s | n.s |
| AP-18 (500 µM) | | | | | | | |
| AP-18 (1000 µM) | n.s | n.s | n.s | n.s | P<0.05 | P<0.01 | P<0.001 |

| AP2-18 (1000 µM) vs | Time (hours) | | | | | | |
|---|---|---|---|---|---|---|---|
| | 0 | 1 | 2 | 3 | 4 | 5 | 6 |
| ALA (250 µM) | n.s | P<0.01 | P<0.001 | P<0.001 | P<0.001 | P<0.001 | P<0.001 |
| ALA (500 µM) | n.s | P<0.001 | P<0.001 | P<0.001 | P<0.001 | P<0.001 | P<0.001 |
| ALA (1000 µM) | n.s | P<0.001 | P<0.001 | P<0.001 | P<0.001 | P<0.001 | P<0.001 |
| ALA (250 µM) + CP94 (250 µM) | n.s | P<0.01 | P<0.001 | P<0.001 | P<0.001 | P<0.001 | P<0.001 |
| ALA (500 µM) + CP94 (500 µM) | n.s | P<0.05 | P<0.05 | n.s | P<0.05 | n.s | P<0.001 |
| ALA (1000 µM) + CP94 (1000 µM) | P<0.05 | P<0.01 | P<0.001 | P<0.001 | P<0.001 | P<0.001 | P<0.001 |
| MAL (250 µM) | P<0.01 | P<0.001 | P<0.001 | P<0.001 | P<0.001 | P<0.001 | P<0.001 |
| MAL (500 µM) | P<0.05 | P<0.001 | P<0.001 | P<0.001 | P<0.001 | P<0.001 | P<0.001 |
| MAL (1000 µM) | n.s | P<0.01 | P<0.001 | P<0.001 | P<0.001 | P<0.001 | P<0.001 |
| MAL (250 µM) + CP94 (250 µM) | P<0.001 | P<0.05 | P<0.001 | P<0.001 | P<0.001 | P<0.001 | P<0.001 |
| MAL (500 µM) + CP94 (500 µM) | P<0.001 | P<0.01 | P<0.001 | P<0.001 | P<0.001 | P<0.001 | P<0.001 |
| MAL (1000 µM) + CP94 (1000 µM) | n.s | P<0.05 | P<0.01 | P<0.01 | P<0.001 | P<0.001 | P<0.001 |
| AP-18 (250 µM) | n.s | n.s | P<0.01 | P<0.001 | P<0.001 | P<0.001 | P<0.001 |
| AP-18 (500 µM) | n.s | n.s | n.s | n.s | P<0.05 | P<0.01 | P<0.001 |
| AP-18 (1000 µM) | | | | | | | |

P<.... Significantly greater than
P<.... Significantly less than
n.s No significant difference

| vs | 0 | 1 | 2 | 3 | 4 | 5 | 6 |
|---|---|---|---|---|---|---|---|
| | | | | Time (hours) | | | |
| ALA (250 μM) | n.s | n.s | P<0.01 | P<0.001 | P<0.001 | P<0.001 | P<0.001 |
| ALA (500 μM) | n.s | n.s | P<0.05 | P<0.01 | P<0.001 | P<0.001 | P<0.001 |
| ALA (1000 μM) | n.s | n.s | n.s | P<0.01 | P<0.001 | P<0.001 | P<0.001 |
| ALA (250 μM) + CP94 (250 μM) | n.s | n.s | P<0.05 | P<0.01 | P<0.001 | P<0.001 | P<0.001 |
| ALA (500 μM) + CP94 (500 μM) | n.s | n.s | n.s | P<0.05 | P<0.001 | P<0.001 | P<0.001 |
| ALA (1000 μM) + CP94 (1000 μM) | n.s | n.s | n.s | P<0.05 | P<0.01 | P<0.001 | P<0.001 |
| MAL (250 μM) | n.s | n.s | P<0.001 | P<0.001 | P<0.001 | P<0.001 | P<0.001 |
| MAL (500 μM) | n.s | n.s | P<0.001 | P<0.001 | P<0.001 | P<0.001 | P<0.001 |
| MAL (1000 μM) | n.s | n.s | P<0.05 | P<0.01 | P<0.001 | P<0.001 | P<0.001 |
| MAL (250 μM) + CP94 (250 μM) | n.s | n.s | P<0.01 | P<0.001 | P<0.001 | P<0.001 | P<0.001 |
| MAL (500 μM) + CP94 (500 μM) | n.s | n.s | P<0.001 | P<0.001 | P<0.001 | P<0.001 | P<0.001 |
| MAL (1000 μM) + CP94 (1000 μM) | n.s | n.s | P<0.05 | P<0.001 | P<0.001 | P<0.001 | P<0.001 |
| AP-18 (250 μM) | | | | | | | |
| AP-18 (500 μM) | n.s | n.s | n.s | P<0.01 | P<0.001 | P<0.001 | P<0.001 |
| AP-18 (1000 μM) | n.s | n.s | P<0.001 | P<0.001 | P<0.001 | P<0.001 | P<0.001 |

AP2-18 (500 μM)

| vs | 0 | 1 | 2 | 3 | 4 | 5 | 6 |
|---|---|---|---|---|---|---|---|
| | | | | Time (hours) | | | |
| ALA (250 μM) | n.s | P<0.05 | P<0.01 | P<0.001 | P<0.001 | P<0.001 | P<0.001 |
| ALA (500 μM) | n.s | n.s | P<0.001 | P<0.001 | P<0.001 | P<0.001 | P<0.001 |
| ALA (1000 μM) | n.s | n.s | P<0.001 | P<0.001 | P<0.001 | P<0.001 | P<0.001 |
| ALA (250 μM) + CP94 (250 μM) | n.s | n.s | P<0.001 | P<0.001 | P<0.001 | P<0.001 | P<0.001 |
| ALA (500 μM) + CP94 (500 μM) | n.s | n.s | P<0.001 | P<0.001 | P<0.001 | P<0.001 | P<0.001 |
| ALA (1000 μM) + CP94 (1000 μM) | n.s | n.s | P<0.001 | P<0.001 | P<0.001 | P<0.001 | P<0.001 |
| MAL (250 μM) | n.s | P<0.01 | P<0.001 | P<0.001 | P<0.001 | P<0.001 | P<0.001 |
| MAL (500 μM) | n.s | P<0.05 | P<0.001 | P<0.001 | P<0.001 | P<0.001 | P<0.001 |
| MAL (1000 μM) | n.s | n.s | P<0.001 | P<0.001 | P<0.001 | P<0.001 | P<0.001 |
| MAL (250 μM) + CP94 (250 μM) | n.s | n.s | P<0.001 | P<0.001 | P<0.001 | P<0.001 | P<0.001 |
| MAL (500 μM) + CP94 (500 μM) | n.s | P<0.05 | P<0.001 | P<0.001 | P<0.001 | P<0.001 | P<0.001 |
| MAL (1000 μM) + CP94 (1000 μM) | n.s | n.s | P<0.001 | P<0.001 | P<0.001 | P<0.001 | P<0.001 |
| AP-18 (250 μM) | n.s | n.s | n.s | P<0.01 | P<0.001 | P<0.001 | P<0.001 |
| AP-18 (500 μM) | | | | | | | |
| AP-18 (1000 μM) | n.s | n.s | n.s | n.s | P<0.05 | P<0.05 | P<0.01 |

AP2-18 (1000 μM)

| vs | 0 | 1 | 2 | 3 | 4 | 5 | 6 |
|---|---|---|---|---|---|---|---|
| | | | | Time (hours) | | | |
| ALA (250 μM) | n.s | P<0.001 | P<0.001 | P<0.001 | P<0.001 | P<0.001 | P<0.001 |
| ALA (500 μM) | n.s | P<0.01 | P<0.001 | P<0.001 | P<0.001 | P<0.001 | P<0.001 |
| ALA (1000 μM) | n.s | P<0.01 | P<0.001 | P<0.001 | P<0.001 | P<0.001 | P<0.001 |
| ALA (250 μM) + CP94 (250 μM) | n.s | P<0.01 | P<0.001 | P<0.001 | P<0.001 | P<0.001 | P<0.001 |
| ALA (500 μM) + CP94 (500 μM) | n.s | P<0.01 | P<0.001 | P<0.001 | P<0.001 | P<0.001 | P<0.001 |
| ALA (1000 μM) + CP94 (1000 μM) | n.s | P<0.01 | P<0.001 | P<0.001 | P<0.001 | P<0.001 | P<0.001 |
| MAL (250 μM) | n.s | P<0.001 | P<0.001 | P<0.001 | P<0.001 | P<0.001 | P<0.001 |
| MAL (500 μM) | n.s | P<0.001 | P<0.001 | P<0.001 | P<0.001 | P<0.001 | P<0.001 |
| MAL (1000 μM) | n.s | P<0.01 | P<0.001 | P<0.001 | P<0.001 | P<0.001 | P<0.001 |
| MAL (250 μM) + CP94 (250 μM) | n.s | P<0.01 | P<0.001 | P<0.001 | P<0.001 | P<0.001 | P<0.001 |
| MAL (500 μM) + CP94 (500 μM) | n.s | P<0.001 | P<0.001 | P<0.001 | P<0.001 | P<0.001 | P<0.001 |
| MAL (1000 μM) + CP94 (1000 μM) | n.s | P<0.01 | P<0.001 | P<0.001 | P<0.001 | P<0.001 | P<0.001 |
| AP-18 (250 μM) | n.s | n.s | P<0.001 | P<0.001 | P<0.001 | P<0.001 | P<0.001 |
| AP-18 (500 μM) | n.s | n.s | n.s | n.s | P<0.05 | P<0.05 | P<0.01 |
| AP-18 (1000 μM) | | | | | | | |

P<... Significantly greater than
P<... Significantly less than
n.s No significant difference

Figure 4B

AP2-18 (250 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | P<0.05 |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.05 |
| MAL (1000 µM) + CP94 (1000 µM) | n.s |
| AP-18 (250 µM) | |
| AP-18 (500 µM) | n.s |
| AP-18 (1000 µM) | n.s |

| | |
|---|---|
| P<... | Significantly greater than |
| P<... | Significantly less than |
| n.s | No significant difference |

AP2-18 (500 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | P<0.05 |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.05 |
| MAL (1000 µM) + CP94 (1000 µM) | n.s |
| AP-18 (250 µM) | n.s |
| AP-18 (500 µM) | |
| AP-18 (1000 µM) | n.s |

AP2-18 (1000 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | P<0.05 |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.05 |
| MAL (1000 µM) + CP94 (1000 µM) | n.s |
| AP-18 (250 µM) | n.s |
| AP-18 (500 µM) | n.s |
| AP-18 (1000 µM) | |

| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | n.s |
| AP-18 (250 µM) | ▬ |
| AP-18 (500 µM) | n.s |
| AP-18 (1000 µM) | n.s |

| | | |
|---|---|---|
| | P<... | Significantly greater than |
| | P<... | Significantly less than |
| | n.s | No significant difference |

AP2-18 (500 µM)
vs

| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | n.s |
| AP-18 (250 µM) | n.s |
| AP-18 (500 µM) | ▬ |
| AP-18 (1000 µM) | n.s |

AP2-18 (1000 µM)
vs

| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | n.s |
| AP-18 (250 µM) | n.s |
| AP-18 (500 µM) | n.s |
| AP-18 (1000 µM) | ▬ |

Figure 6C

AP2-18 (250 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | P<0.001 |
| AP-18 (500 µM) | n.s |
| AP-18 (1000 µM) | n.s |

| | | |
|---|---|---|
| P<... | | Significantly greater than |
| P<... | | Significantly less than |
| n.s | | No significant difference |

AP2-18 (500 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | n.s |
| AP-18 (500 µM) | P<0.001 |
| AP-18 (1000 µM) | n.s |

AP2-18 (1000 µM)
vs
| | |
|---|---|
| Untreated | P<0.001 |
| ALA (250 µM) | P<0.01 |
| ALA (500 µM) | P<0.05 |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | n.s |
| AP-18 (500 µM) | n.s |
| AP-18 (1000 µM) | P<0.001 |

| | | | |
|---|---|---|---|
| ALA (250 µM) | P<0.05 | P<.... | Significantly greater than |
| ALA (500 µM) | n.s | P<.... | Significantly less than |
| ALA (1000 µM) | n.s | n.s | No significant difference |
| ALA (250 µM) + CP94 (250 µM) | n.s | | |
| ALA (500 µM) + CP94 (500 µM) | n.s | | |
| ALA (1000 µM) + CP94 (1000 µM) | n.s | | |
| MAL (250 µM) | P<0.001 | | |
| MAL (500 µM) | P<0.001 | | |
| MAL (1000 µM) | n.s | | |
| MAL (250 µM) + CP94 (250 µM) | n.s | | |
| MAL (500 µM) + CP94 (500 µM) | n.s | | |
| MAL (1000 µM) + CP94 (1000 µM) | n.s | | |
| AP-18 (250 µM) | | | |
| AP-18 (500 µM) | n.s | | |
| AP-18 (1000 µM) | P<0.01 | | |

AP2-18 (500 µM)
vs

| | |
|---|---|
| ALA (250 µM) | P<0.001 |
| ALA (500 µM) | P<0.001 |
| ALA (1000 µM) | P<0.01 |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.05 |
| MAL (250 µM) + CP94 (250 µM) | P<0.05 |
| MAL (500 µM) + CP94 (500 µM) | n.s |
| MAL (1000 µM) + CP94 (1000 µM) | n.s |
| AP-18 (250 µM) | n.s |
| AP-18 (500 µM) | |
| AP-18 (1000 µM) | n.s |

AP2-18 (1000 µM)
vs

| | |
|---|---|
| ALA (250 µM) | P<0.001 |
| ALA (500 µM) | P<0.001 |
| ALA (1000 µM) | P<0.001 |
| ALA (250 µM) + CP94 (250 µM) | P<0.001 |
| ALA (500 µM) + CP94 (500 µM) | P<0.05 |
| ALA (1000 µM) + CP94 (1000 µM) | P<0.001 |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | P<0.01 |
| AP-18 (250 µM) | P<0.01 |
| AP-18 (500 µM) | n.s |
| AP-18 (1000 µM) | |

| | |
|---|---|
| ALA (250 µM) | P<0.001 |
| ALA (500 µM) | P<0.01 |
| ALA (1000 µM) | P<0.05 |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | ■ |
| AP-18 (500 µM) | n.s |
| AP-18 (1000 µM) | P<0.001 |

| P<.... | Significantly greater than |
|---|---|
| P<.... | Significantly less than |
| n.s | No significant difference |

AP2-18 (500 µM)
vs

| | |
|---|---|
| ALA (250 µM) | P<0.001 |
| ALA (500 µM) | P<0.001 |
| ALA (1000 µM) | P<0.001 |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.01 |
| MAL (250 µM) + CP94 (250 µM) | P<0.001 |
| MAL (500 µM) + CP94 (500 µM) | P<0.01 |
| MAL (1000 µM) + CP94 (1000 µM) | n.s |
| AP-18 (250 µM) | n.s |
| AP-18 (500 µM) | ■ |
| AP-18 (1000 µM) | n.s |

AP2-18 (1000 µM)
vs

| | |
|---|---|
| ALA (250 µM) | P<0.001 |
| ALA (500 µM) | P<0.001 |
| ALA (1000 µM) | P<0.001 |
| ALA (250 µM) + CP94 (250 µM) | P<0.001 |
| ALA (500 µM) + CP94 (500 µM) | n.s |
| ALA (1000 µM) + CP94 (1000 µM) | P<0.001 |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | P<0.01 |
| AP-18 (250 µM) | P<0.001 |
| AP-18 (500 µM) | n.s |
| AP-18 (1000 µM) | ■ |

| | |
|---|---|
| ALA (250 µM) | P<0.001 |
| ALA (500 µM) | P<0.001 |
| ALA (1000 µM) | P<0.01 |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | n.s |
| MAL (250 µM) + CP94 (250 µM) | P<0.001 |
| MAL (500 µM) + CP94 (500 µM) | P<0.05 |
| MAL (1000 µM) + CP94 (1000 µM) | n.s |
| AP-18 (250 µM) | |
| AP-18 (500 µM) | n.s |
| AP-18 (1000 µM) | P<0.001 |

| | | |
|---|---|---|
| P<.... | | Significantly greater than |
| P<.... | | Significantly less than |
| n.s | | No significant difference |

AP2-18 (500 µM)
vs

| | |
|---|---|
| ALA (250 µM) | P<0.001 |
| ALA (500 µM) | P<0.001 |
| ALA (1000 µM) | P<0.001 |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | n.s |
| AP-18 (250 µM) | n.s |
| AP-18 (500 µM) | |
| AP-18 (1000 µM) | P<0.05 |

AP2-18 (1000 µM)
vs

| | |
|---|---|
| ALA (250 µM) | P<0.001 |
| ALA (500 µM) | P<0.001 |
| ALA (1000 µM) | P<0.001 |
| ALA (250 µM) + CP94 (250 µM) | P<0.001 |
| ALA (500 µM) + CP94 (500 µM) | P<0.05 |
| ALA (1000 µM) + CP94 (1000 µM) | P<0.001 |
| MAL (250 µM) | P<0.001 |
| MAL (500 µM) | P<0.001 |
| MAL (1000 µM) | P<0.001 |
| MAL (250 µM) + CP94 (250 µM) | P<0.001 |
| MAL (500 µM) + CP94 (500 µM) | P<0.001 |
| MAL (1000 µM) + CP94 (1000 µM) | P<0.001 |
| AP-18 (250 µM) | P<0.001 |
| AP-18 (500 µM) | P<0.05 |
| AP-18 (1000 µM) | |

| | |
|---|---|
| Untreated | n.s |
| ALA (250 µM) | n.s |
| ALA (500 µM) | n.s |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | ■ |
| AP-18 (500 µM) | n.s |
| AP-18 (1000 µM) | n.s |

AP2-18 (500 µM)
vs

| | |
|---|---|
| Untreated | n.s |
| ALA (250 µM) | n.s |
| ALA (500 µM) | n.s |
| ALA (1000 µM) | $P<0.05$ |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | n.s |
| AP-18 (500 µM) | ■ |
| AP-18 (1000 µM) | n.s |

AP2-18 (1000 µM) vs

| | |
|---|---|
| Untreated | n.s |
| ALA (250 µM) | n.s |
| ALA (500 µM) | n.s |
| ALA (1000 µM) | n.s |
| ALA (250 µM) + CP94 (250 µM) | n.s |
| ALA (500 µM) + CP94 (500 µM) | n.s |
| ALA (1000 µM) + CP94 (1000 µM) | n.s |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | n.s |
| AP-18 (250 µM) | n.s |
| AP-18 (500 µM) | n.s |
| AP-18 (1000 µM) | ■ |

| | |
|---|---|
| $P<....$ (black) | Significantly greater than |
| $P<....$ (shaded) | Significantly less than |
| n.s | No significant difference |

| | |
|---|---|
| Untreated | n.s |
| ALA (250 µM) | n.s |
| ALA (500 µM) | n.s |
| ALA (1000 µM) | n.s |
| ALA (250 µM) + CP94 (250 µM) | n.s |
| ALA (500 µM) + CP94 (500 µM) | P<0.001 |
| ALA (1000 µM) + CP94 (1000 µM) | P<0.001 |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | P<0.001 |
| AP-18 (250 µM) | |
| AP-18 (500 µM) | n.s |
| AP-18 (1000 µM) | n.s |

AP2-18 (500 µM)
vs

| | |
|---|---|
| Untreated | n.s |
| ALA (250 µM) | n.s |
| ALA (500 µM) | n.s |
| ALA (1000 µM) | P<0.05 |
| ALA (250 µM) + CP94 (250 µM) | n.s |
| ALA (500 µM) + CP94 (500 µM) | P<0.001 |
| ALA (1000 µM) + CP94 (1000 µM) | P<0.001 |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | P<0.001 |
| AP-18 (250 µM) | n.s |
| AP-18 (500 µM) | |
| AP-18 (1000 µM) | n.s |

AP2-18 (1000 µM) vs

| | |
|---|---|
| Untreated | n.s |
| ALA (250 µM) | n.s |
| ALA (500 µM) | n.s |
| ALA (1000 µM) | n.s |
| ALA (250 µM) + CP94 (250 µM) | n.s |
| ALA (500 µM) + CP94 (500 µM) | P<0.001 |
| ALA (1000 µM) + CP94 (1000 µM) | P<0.001 |
| MAL (250 µM) | n.s |
| MAL (500 µM) | n.s |
| MAL (1000 µM) | n.s |
| MAL (250 µM) + CP94 (250 µM) | n.s |
| MAL (500 µM) + CP94 (500 µM) | n.s |
| MAL (1000 µM) + CP94 (1000 µM) | P<0.001 |
| AP-18 (250 µM) | n.s |
| AP-18 (500 µM) | n.s |
| AP-18 (1000 µM) | |

| | |
|---|---|
| P<.... | Significantly greater than |
| P<.... | Significantly less than |
| n.s | No significant difference |

Figure 11B(ii)

AP2-18 (250 μM)
vs
| | |
|---|---|
| Untreated | P<0.001 |
| ALA (250 μM) | P<0.01 |
| ALA (500 μM) | P<0.05 |
| ALA (1000 μM) | n.s |
| ALA (250 μM) + CP94 (250 μM) | n.s |
| ALA (500 μM) + CP94 (500 μM) | n.s |
| ALA (1000 μM) + CP94 (1000 μM) | n.s |
| MAL (250 μM) | P<0.001 |
| MAL (500 μM) | P<0.001 |
| MAL (1000 μM) | P<0.001 |
| MAL (250 μM) + CP94 (250 μM) | P<0.001 |
| MAL (500 μM) + CP94 (500 μM) | P<0.001 |
| MAL (1000 μM) + CP94 (1000 μM) | n.s |
| AP-18 (250 μM) | ■ |
| AP-18 (500 μM) | n.s |
| AP-18 (1000 μM) | n.s |

| | |
|---|---|
| P<.... | Significantly greater than |
| P<.... | Significantly less than |
| n.s | No significant difference |

AP2-18 (500 μM)
vs
| | |
|---|---|
| Untreated | P<0.001 |
| ALA (250 μM) | P<0.01 |
| ALA (500 μM) | P<0.05 |
| ALA (1000 μM) | n.s |
| ALA (250 μM) + CP94 (250 μM) | n.s |
| ALA (500 μM) + CP94 (500 μM) | n.s |
| ALA (1000 μM) + CP94 (1000 μM) | n.s |
| MAL (250 μM) | P<0.001 |
| MAL (500 μM) | P<0.001 |
| MAL (1000 μM) | P<0.001 |
| MAL (250 μM) + CP94 (250 μM) | P<0.001 |
| MAL (500 μM) + CP94 (500 μM) | P<0.001 |
| MAL (1000 μM) + CP94 (1000 μM) | n.s |
| AP-18 (250 μM) | n.s |
| AP-18 (500 μM) | ■ |
| AP-18 (1000 μM) | n.s |

AP2-18 (1000 μM) vs
| | |
|---|---|
| Untreated | P<0.001 |
| ALA (250 μM) | P<0.01 |
| ALA (500 μM) | P<0.05 |
| ALA (1000 μM) | n.s |
| ALA (250 μM) + CP94 (250 μM) | n.s |
| ALA (500 μM) + CP94 (500 μM) | n.s |
| ALA (1000 μM) + CP94 (1000 μM) | n.s |
| MAL (250 μM) | P<0.001 |
| MAL (500 μM) | P<0.001 |
| MAL (1000 μM) | P<0.001 |
| MAL (250 μM) + CP94 (250 μM) | P<0.001 |
| MAL (500 μM) + CP94 (500 μM) | P<0.001 |
| MAL (1000 μM) + CP94 (1000 μM) | n.s |
| AP-18 (250 μM) | n.s |
| AP-18 (500 μM) | n.s |
| AP-18 (1000 μM) | ■ |

Figure 11C(ii)

PYRIDINONE COMPOUNDS FOR USE IN PHOTODYNAMIC THERAPY

FIELD OF THE INVENTION

The present invention relates to a novel compound and its preparation and use, and to compositions comprising the compound.

BACKGROUND TO THE INVENTION

Photodynamic therapy (PDT) is a therapy employed routinely in the treatment of superficial dermatological malignancies and is under investigation for a range of additional tumour types. Most applications of PDT involve the use of an active compound, known as a photosensitizer, and a light source, the wavelength of which can be chosen to be appropriate for exciting the photosensitizer to produce reactive oxygen species. This leads to the destruction of any tissues which have either selectively taken up the photosensitizer or have been locally exposed to light.

For example, a PDT treatment of human skin cancer may involve the following steps. Firstly, a photosensitizer precursor is administered to the patient. The photosensitizer precursor is taken up by the cells and converted to a photosensitizer. The area to be treated is then exposed to light of the appropriate wavelength. The photosensitizer absorbs light and reacts with nearby tissue oxygen, resulting in reactive oxygen species. These reactive oxygen species react with biomolecules, fatally damaging some of the cells in the treatment area.

PDT has particularly found a niche in the treatment of dermatological tumours where light can be readily applied to the surface of the skin; clinically substantial subsets of skin tumours are difficult to treat by conventional therapies (because of size, site or multiple lesions presentation). In the treatment of skin conditions, the photosensitizer or photosensitizer precursor can be applied topically, and locally excited by a light source. In the local treatment of internal cancer cells, on the other hand, photosensitizers or photosensitizer precursors can for example be administered intravenously and light can be delivered to the target area using endoscopes and fibre optic catheters. Compared to normal healthy tissues, most types of cancer cells are especially active in both the uptake and accumulation of photosensitizers, which makes cancer cells especially vulnerable to PDT, since having more photosensitizer present in a cell leads to more damage to that cell during PDT.

Photosensitizer precursors currently employed in dermatological PDT include aminolevulinic acid (ALA), methyl aminolevulinate (MAL) and hexyl aminolevulinate (HAL). If ALA, MAL or HAL is used as a photosensitizer precursor, it is converted by the cells to the photosensitizer protoporphyrin IX (PpIX).

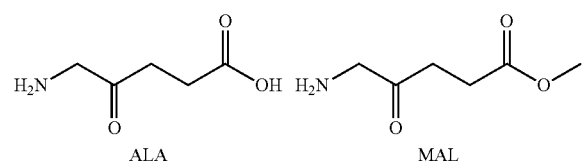

Porphyrins have long been considered as suitable agents for tumour photodiagnosis and tumour PDT because cancer cells exhibit a significantly greater uptake and affinity for porphyrins compared to normal quiescent tissues; cancer cells therefore naturally accumulate porphyrins.

An additional feature of the photosensitizer protoporphyrin IX (PpIX) is its ability to fluoresce, which in combination with cancer cells' natural accumulation of porphyrins allows for photodiagnosis (PD) of tumours. PD has been used by surgeons for enabling greater precision in the removal of tumours, such as for example brain tumours.

PpIX is naturally present in all nucleated mammalian cells at low concentrations; it is an intermediate in the biosynthesis of haem. In the haem biosynthesis, ALA is converted to PpIX (via a number of intermediate steps), after which PpIX is converted to haem by the insertion of a $Fe^{2+}$ ion into PpIX by the enzyme ferrochelatase.

In order for PDT to be effective, it is necessary to increase the amount of PpIX which is present in a cell. One way of doing this is to add more ALA, MAL or HAL to a cell, which will be converted to PpIX. However, the haem biosynthesis pathway has a maximum limit over which additional precursor administration does not produce any additional benefit. Furthermore, excessive ALA oral administration has been demonstrated to induce liver toxicity in humans. Usually, the presence of free haem acts as a negative feedback mechanism inhibiting ALA synthesis. However, the exogenous administration of large amounts of ALA or MAL bypasses this negative feedback signal and results in a temporary accumulation of PpIX within the cells, since the insertion of $Fe^{2+}$ into PpIX to form haem is relatively slow. Furthermore, PpIX may accumulate in the cell even more by slowing down the step of converting PpIX to haem by insertion of $Fe^{2+}$, which may be achieved by limiting the iron supply in a cell. Bech, O. et al., J Photochem Photobiol B, 1997, 41, 136-144; Curnow, A. et al., BJC, 1998, 78, 1278-1282; Pye, A. et al., Photochem Photobiol, 2007, 83(3), 766-73; and Blake, E. et al., Photochem Photobiol, 2010, 86(5), 1154-60 describe how the use of the iron chelator CP94, shown below, in combination with ALA can increase accumulation of PpIX.

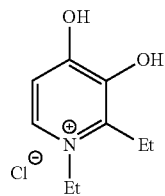

CP94

A need however remains for new photosensitizer precursors which have an improved activity profile in photodynamic therapy, especially since currently photodynamic therapy is not effective for all tumour types; clearance rates for thicker nodular basal cell carcinoma (BCC), for example, remain lower than for superficial BCC.

It is an aim of the invention to provide a new compound which can be used as a photosensitizer precursor, and which can show an improved activity profile in photodynamic therapy.

STATEMENTS OF THE INVENTION

According to a first aspect of the invention there is provided a compound which is a compound of formula (I) or any salt thereof:

(I)

wherein $R^1$ is a $C_1$-$C_6$ alkyl group, $R^2$ is H or a $C_1$-$C_6$ alkyl group, $R^3$ is H or a $C_1$-$C_6$ alkyl group, and n is an integer from 0 to 5.

In an embodiment, the compound according to the first aspect of the invention is a compound of formula (I) as defined above, a salt of formula (Ia) or a salt of formula (Ib):

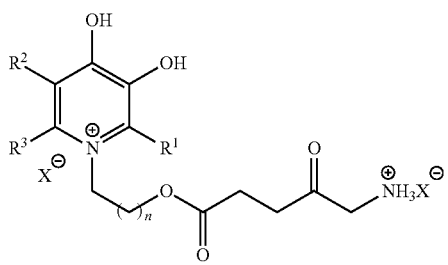

(Ia)

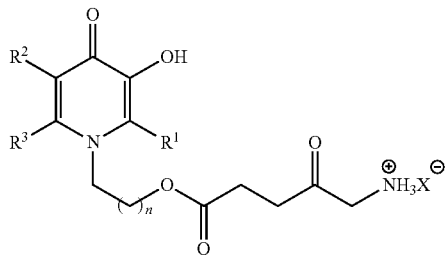

(Ib)

wherein $R^1$, $R^2$, $R^3$ and n are as defined above; and each $X^-$ is independently selected from monovalent counterions.

In an embodiment, the compound according to the first aspect of the invention is a compound of formula (I) or a salt of formula (Ia) as defined above. In an embodiment, the compound according to the first aspect of the invention is a compound of formula (I) as defined above.

In an embodiment, the compound according to the first aspect of the invention is a salt of formula (Ia) as defined above.

The monovalent counterion $X^-$ may be the conjugate base of any common acid. $X^-$ may, for example, be a halide, hydrogen sulphate, nitrate, or a carboxylate such as acetate or formate.

In an embodiment, $X^-$ is a halide, such as, for example, $F^-$, $Cl^-$, $Br^-$ or $I^-$. In an embodiment, $X^-$ is $Cl^-$.

An alkyl group may be a straight or branched chain alkyl group.

In the compound according to the first aspect of the invention, $R^1$ is a $C_1$-$C_6$ alkyl group, which includes, for example, methyl, ethyl, n-propyl, i-propyl, n-butyl, t-butyl, n-pentyl, i-pentyl, t-pentyl and hexyl. In an embodiment, $R^1$ is a $C_1$-$C_5$ alkyl group, which includes, for example, methyl, ethyl, n-propyl, i-propyl, n-butyl, t-butyl, n-pentyl, i-pentyl, and t-pentyl. In an embodiment, $R^1$ is a $C_1$-$C_4$ alkyl group, which includes, for example, methyl, ethyl, n-propyl, i-propyl, n-butyl and t-butyl. In an embodiment, $R^1$ is a $C_1$-$C_3$ alkyl group, which includes, for example, methyl, ethyl, n-propyl and i-propyl. In an embodiment, $R^1$ is a $C_1$-$C_2$ alkyl group, i.e. methyl or ethyl. In an embodiment, $R^1$ is a $C_2$ alkyl group, i.e. ethyl.

In the compound according to the first aspect of the invention, $R^2$ is H or a $C_1$-$C_6$ alkyl group, which includes, for example, methyl, ethyl, n-propyl, i-propyl, n-butyl, t-butyl, n-pentyl, i-pentyl, t-pentyl and hexyl. In an embodiment, $R^2$ is H or a $C_1$-$C_5$ alkyl group, which includes, for example, methyl, ethyl, n-propyl, i-propyl, n-butyl, t-butyl, n-pentyl, i-pentyl, and t-pentyl. In an embodiment, $R^2$ is H or a $C_1$-$C_4$ alkyl group, which includes, for example, methyl, ethyl, n-propyl, i-propyl, n-butyl and t-butyl. In an embodiment, $R^2$ is H or a $C_1$-$C_3$ alkyl group, which includes, for example, methyl, ethyl, n-propyl and i-propyl. In an embodiment, $R^2$ is H or a $C_1$-$C_2$ alkyl group, i.e. methyl or ethyl. In an embodiment, $R^2$ is H.

In the compound according to the first aspect of the invention, $R^3$ is H or a $C_1$-$C_6$ alkyl group, which includes, for example, methyl, ethyl, n-propyl, i-propyl, n-butyl, t-butyl, n-pentyl, i-pentyl, t-pentyl and hexyl. In an embodiment, $R^3$ is H or a $C_1$-$C_5$ alkyl group, which includes, for example, methyl, ethyl, n-propyl, i-propyl, n-butyl, t-butyl, n-pentyl, i-pentyl, and t-pentyl. In an embodiment, $R^3$ is H or a $C_1$-$C_4$ alkyl group, which includes, for example, methyl, ethyl, n-propyl, i-propyl, n-butyl and t-butyl. In an embodiment, $R^3$ is H or a $C_1$-$C_3$ alkyl group, which includes, for example, methyl, ethyl, n-propyl and i-propyl. In an embodiment, $R^3$ is H or a $C_1$-$C_2$ alkyl group, i.e. methyl or ethyl. In an embodiment, $R^3$ is H.

In an embodiment, $R^2$ and $R^3$ are H.

In the compound according to the first aspect of the invention, n is an integer from 0 to 5. In an embodiment, n is from 0 to 4, or from 0 to 3, or from 0 to 2, or from 0 to 1, or from 1 to 5, or from 1 to 4, or from 1 to 3, or from 1 to 2. In an embodiment, n is 1.

In an embodiment, $R^1$ is methyl or ethyl; $R^2$ is H, methyl or ethyl; $R^3$ is H, methyl or ethyl; and n is 1.

In an embodiment, $R^1$ is ethyl, $R^2$ and $R^3$ are H, and n is 1. This compound and its salt forms are effectively a combination of ALA and the iron chelating compound CP94, which have been linked via an ester linkage. Surprisingly, this linked compound has a better activity profile than a combination of ALA and CP94 as separate active agents.

This is highly surprising for a number of reasons. Firstly, delivering ALA and CP94 in a linked format (rather than separately) might be expected to alter the way the compounds enter the cell; bigger molecules tend to not enter cells as effectively as smaller molecules and may use different transporters. In fact, it is thought that ALA and MAL may enter cells via different membrane transporters and hence this might also have been true for the compound of the invention in which ALA and CP94 are linked. This new entity, therefore, was not guaranteed to produce even the same level of results as ALA and CP94 as separate agents, let alone better ones.

In addition to this, it was very difficult to predict how the linked format would affect the innate cellular biochemistry relied on to produce the natural photosensitiser PpIX. ALA is normally formed by ALA synthase in the mitochondrion before entering the portion of the haem biosynthesis pathway that occurs in the cytosol. The later step of insertion of iron into the PpIX porphyrin ring to form haem occurs in the mitochondrion. In order to influence this pathway in such a way that PpIX accumulates, the iron chelator needs to be able to diminish mitochondrial levels of iron either directly or indirectly. However, the compound of the invention in which ALA and CP94 are linked first needs to be separated into the active agents by esterases present in the cytosol. The linked format might therefore be expected to alter the cellular compartments (such as the cytosol and the mitochondrion) in which the separate compounds end up, which could also alter the regulation of the haem biosynthetic pathway. In addition, in theory it might seem better to deliver the CP94 before the ALA, in order to chelate the iron prior to producing the PpIX, whereas delivering the agents in a linked format means that the agents are delivered simultaneously. These factors contributed further to render the utility of the invented compound even more surprising.

Furthermore, iron chelator CP94 is bidentate and it therefore takes three CP94 molecules to bind one $Fe^{2+}$ ion. In addition to this, in the haem biosynthesis pathway two molecules of ALA dimerize to form porphobilinogen after which four molecules of the latter are condensed, rearranged and cyclised to produce uroporphyrinogen III; this is then converted into protoporphyrin IX via coproporphyrinogen III. Therefore, eight molecules of ALA are needed to form one PpIX molecule, which binds to one $Fe^{2+}$ ion to form one molecule of haem. The theoretical ratio of ALA:CP94 required per $Fe^{2+}$ ion would, therefore, in simplistic biosynthetic terms, be 8 ALA: 3 CP94, i.e. over twice as much ALA as CP94. Despite this, the inventors have found that, highly surprisingly, equal quantities of ALA and CP94 in the specific linked format of the compound of the invention give an excellent activity profile. Without wishing to be bound by theory, in retrospect it may be the case that, in order to make haem formation from PpIX less likely to occur, more CP94 may be required than was theoretically predicted in order to drain the intracellular iron stores.

As set out above, there are a large number of different factors in the environment inside a living cell which influence the activity profile of any active agent added to it, making it very difficult to predict the success of the active agent. It was, therefore, highly surprising to find that equal quantities of ALA and CP94 in the specific linked format of the compound of the invention gave such an excellent activity profile.

In an embodiment, the compound according to the first aspect of the invention is a salt of formula (Ic):

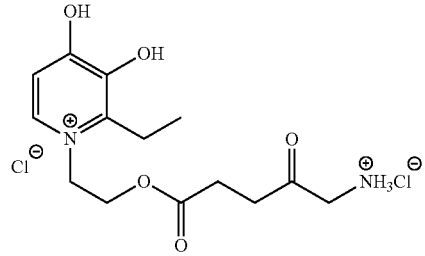

(Ic)

As can be seen from Example 2B, the salt of formula (Ic) is able to produce a significant increase in PpIX accumulation relative to ALA, MAL, a combination of ALA and CP94 as separate active agents, and a combination of MAL and CP94 as separate active agents. Furthermore, as can be seen from Example 2C, the salt of formula (Ic) was also found to be significantly better at reducing cell viability following PDT, especially at low concentrations.

The clinical employment of the salt of formula (Ic) could, therefore, lead to a substantial benefit to patients undergoing dermatological PDT and other PDT applications.

According to a second aspect of the invention there is provided a pharmaceutical composition comprising a compound according to the first aspect of the invention and a pharmaceutically acceptable carrier. Throughout this specification, the term "pharmaceutical" includes veterinary. In an embodiment, the composition is a topical skin treatment formulation.

According to a third aspect of the invention there is provided a process for making a compound according to the first aspect of the invention, the method comprising the step of:

(a) reacting a compound of formula (II) with a compound of formula (III) via an esterification reaction to form a compound of formula (IV);

in accordance with the following reaction scheme:

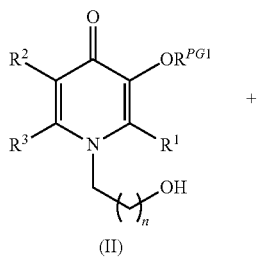

(II)

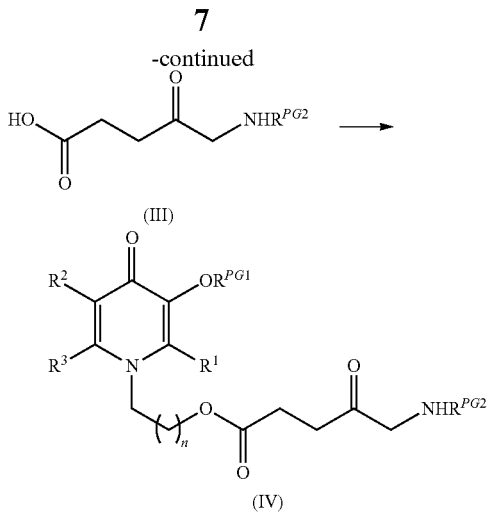

wherein $R^1$, $R^2$, $R^3$ and n are as defined for the first aspect; and $R^{PG1}$ and $R^{PG2}$ are protecting groups.

The term "protecting group" means a group capable of protecting an oxygen atom or a nitrogen atom, which protecting group may, subsequent to the reaction for which protection is employed, be removed without disturbing the remainder of the molecule. Protecting groups are well known and listed in standard texts such as Kocienski P. J., Protecting Groups, 3rd ed., Georg Thieme Verlag, New York, 2005; and Greene T. W., Wuts P. G. M., Protective Groups In Organic Synthesis, 3rd ed., John Wiley & Sons, New York, 1998.

In an embodiment, $R^{PG1}$ is a protecting group selected from benzyl, benzoyl, methoxymethyl (MOM), methoxyethoxymethyl ether (MEM), tetrahydropyranyl (THP), and silicon protecting groups such as, for example, trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

$R^{PG1}$ is an alcohol protecting group. Alcohol protecting groups are well-known to the skilled person and listed in standard texts such as those mentioned above.

In an embodiment, $R^{PG2}$ is a protecting group selected from benzoyl and urethane-type protecting groups such as carboxybenzyl (Cbz), tert-butoxycarbonyl (Boc), 4-methoxybenzyloxycarbonyl, 4-nitrobenzyloxycarbonyl and 9-fluorenylmethyloxycarbonyl (Fmoc).

$R^{PG2}$ is a primary amine protecting group. Primary amine protecting groups are well-known to the skilled person and listed in standard texts such as those mentioned above.

In an embodiment, the process according to the third aspect further comprises the step of:

(b1) deprotecting the compound of formula (IV) to give a compound of formula (I);

in accordance with the following reaction scheme:

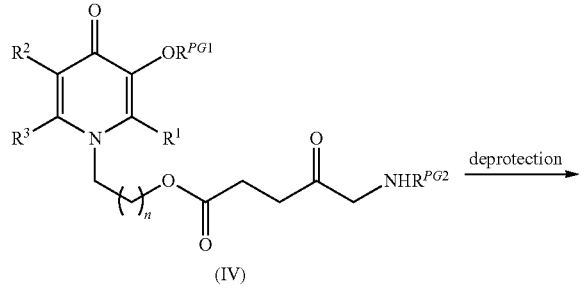

Protection and deprotection can be carried out in the usual ways known to the skilled person; these are routine steps in chemical synthesis.

In an embodiment, the process according to the third aspect further comprises the step of:

(b2) deprotecting the compound of formula (IV) in the presence of acid $H^+X^-$ to give a salt of formula (Ia); in accordance with the following reaction scheme:

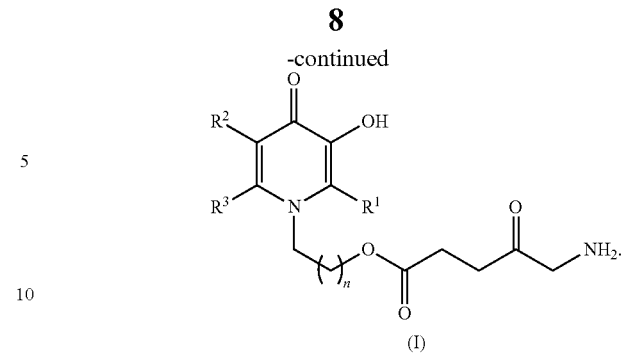

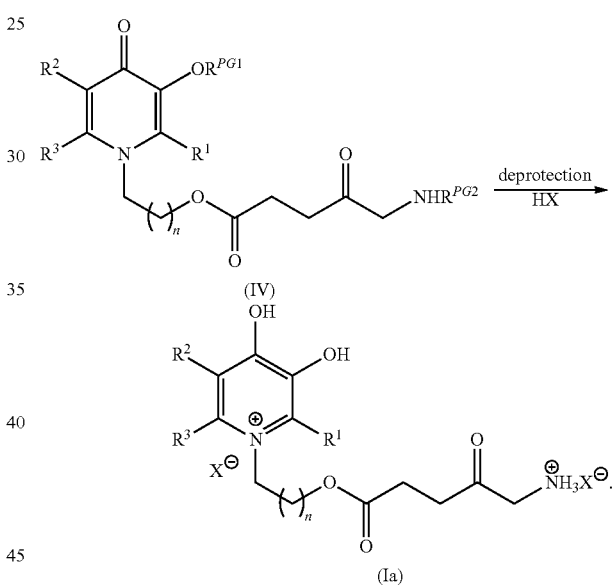

In an embodiment, the process according to the third aspect further comprises the step of:

(b3) deprotecting the compound of formula (IV) in the presence of acid $H^+X^-$ to give a salt of formula (Ib);

in accordance with the following reaction scheme:

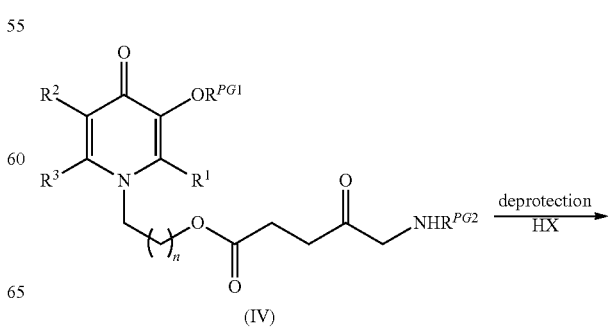

-continued

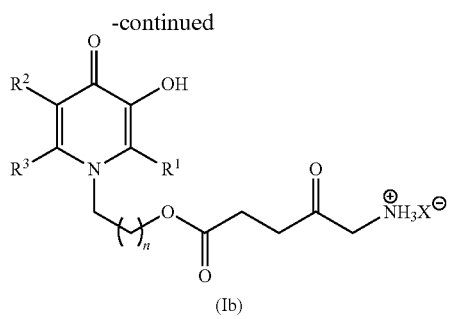
(Ib)

According to a fourth aspect of the invention there is provided a compound according to the first aspect of the invention for use in therapy.

According to a fifth aspect of the invention there is provided a compound according to the first aspect of the invention for use in photodynamic therapy.

In an embodiment, the compound for use according to the fifth aspect of the invention is for use in treating a condition, which is caused by and/or exacerbated by the abnormal proliferation of cells, by photodynamic therapy.

In an embodiment, the compound for use according to the fifth aspect of the invention is for use in treating cancer, by photodynamic therapy. In an embodiment, the compound is for use in treating skin cancer, by photodynamic therapy. In an embodiment, the compound is for use in treating internal cancer cells, by photodynamic therapy.

In an embodiment, the compound for use according to the fifth aspect of the invention is for use in treating *scleroderma*, lichen sclerosus, psoriasis or warts, by photodynamic therapy. In an embodiment, the compound for use according to the fifth aspect of the invention is for use in treating chronic wounds, by photodynamic therapy. Such chronic wounds may, for example, be leg ulcers in the elderly. In an embodiment, the compound for use according to the fifth aspect of the invention is for use in treating acne, by photodynamic therapy. In an embodiment, the compound for use according to the fifth aspect of the invention is for use in treating a microbial infection, by photodynamic therapy. Such a microbial infection may, for example, be caused by bacteria, fungi, viruses and/or yeasts. In an embodiment, the compound for use according to the fifth aspect of the invention is for use in treating a parasitic infestation, by photodynamic therapy. In an embodiment, the compound for use according to the fifth aspect of the invention is for use in treating rheumatoid arthritis, by photodynamic therapy. In an embodiment, the compound for use according to the fifth aspect of the invention is for use in bone marrow purging, by photodynamic therapy, in the treatment of leukaemia.

In an embodiment, the compound for use according to the fifth aspect of the invention is administered topically. In an embodiment, the compound for use according to the fifth aspect of the invention is administered orally. In an embodiment, the compound for use according to the fifth aspect of the invention is administered intravenously.

According to a sixth aspect of the invention there is provided the use of a compound according to the first aspect of the invention in photodynamic treatment for cosmetic purposes.

In an embodiment, the compound is used in the photodynamic treatment for cosmetic purposes of hypertrophic scars, acne scars, wrinkles (rhytides), actinically damaged skin (also known as photodamaged skin or sun damaged skin), rosacea, actinic keratosis, sebaceous gland hyperplasia, lentigines, hirsutism, telangiectasias, port wine stains, erythema, poikiloderma, melisma, dyschromia, hyperpigmentation, mottled or blotchy pigmentation, rough skin patches, poor skin texture, enlarged pores, and/or skin laxity.

In an embodiment, the compound is used in cosmetic photorejuvenation of skin by photodynamic treatment.

According to a seventh aspect of the invention there is provided a compound according to the first aspect of the invention for use in a diagnostic method practised on the human or animal body. In an embodiment, the diagnostic method is a method of diagnosing a condition which is caused by and/or exacerbated by the abnormal proliferation of cells. In an embodiment, the condition which is caused by and/or exacerbated by the abnormal proliferation of cells is cancer.

As mentioned above, PpIX has a fluorescent ability, which enables the photodiagnosis (PD) of tumours. The production of a significantly greater level of PpIX in a significantly shorter time by using the compound according to the first aspect of the invention, therefore, can also result in improved PD.

According to an eighth aspect of the invention there is provided the use of a compound according to the first aspect of the invention in a diagnostic method other than a diagnostic method practised on the human or animal body. In an embodiment, the diagnostic method is an in vitro diagnostic method. For example, PD could be used to enhance the histological and/or microscopic analysis of tumours; this may help to further distinguish normal cells from abnormal cells in a specimen.

In an embodiment, the diagnostic method is a method of diagnosing a condition which is caused by and/or exacerbated by the abnormal proliferation of cells. In an embodiment, the condition which is caused by and/or exacerbated by the abnormal proliferation of cells is cancer.

According to a ninth aspect there is provided the use of a compound according to the first aspect of the invention in the manufacture of a medicament for the treatment, by photodynamic therapy, of a condition which is caused by and/or exacerbated by the abnormal proliferation of cells. In an embodiment, the condition which is caused by and/or exacerbated by the abnormal proliferation of cells is cancer.

A compound according to the first aspect of the invention may also be used in the manufacture of a medicament for the treatment, by photodynamic therapy, of any of the conditions referred to in connection with the fifth aspect of the invention.

According to a tenth aspect of the invention there is provided a method of treatment of a human or animal patient suffering from or at risk of suffering from a condition which is caused by and/or exacerbated by the abnormal proliferation of cells, the method involving administering to the patient a therapeutically effective amount of a compound according to the first aspect of the invention, and exposing a region of the patient containing the compound to light as part of a photodynamic therapy. In an embodiment, the condition which is caused by and/or exacerbated by the abnormal proliferation of cells is cancer.

A compound according to the first aspect of the invention may also be used in a method of treatment of a human or animal patient suffering from or at risk of suffering from any of the conditions referred to in connection with the fifth aspect of the invention, the method involving administering to the patient a therapeutically effective amount of a compound according to the first aspect of the invention, and exposing a region of the patient containing the compound to light as part of a photodynamic therapy.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to compound properties such as optical rotations are—unless stated otherwise—to properties measured under ambient conditions, i.e. at atmospheric pressure and at a temperature of from 16 to 22 or 25° C., or from 18 to 22 or 25° C., for example about 20° C. or about 25° C.

BRIEF DESCRIPTION OF THE DRAWINGS

The present invention will now be further described with reference to the following non-limiting examples, and the accompanying illustrative drawings, of which:

FIG. 2B shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 2 way ANOVA with Bonferroni post-test to compare replicate means).

FIG. 3B shows the results of a statistical analysis of the PpIX accumulation data in Table 2 and FIG. 3A for human epithelial squamous cell carcinoma cells (A431); FIG. 3B shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 2 way ANOVA with Bonferroni post-test to compare replicate means).

FIG. 4B shows the results of a statistical analysis of the PpIX accumulation data in Table 3 and FIG. 4A for human glioblastoma cells (U87MG); FIG. 4B shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 2 way ANOVA with Bonferroni post-test to compare replicate means).

FIG. 5C shows the results of a statistical analysis of the cell viability data in Table 5 and FIG. 5B for human dermal fibroblasts (84BR); FIG. 5C shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 1 way ANOVA with Tukey post-test comparing all pairs of columns).

FIG. 6C shows the results of a statistical analysis of the cell viability data in Table 7 and FIG. 6B for human epithelial squamous cell carcinoma cells (A431); FIG. 6C shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 1 way ANOVA with Tukey post-test comparing all pairs of columns).

FIG. 7C shows the results of a statistical analysis of the cell viability data in Table 9 and FIG. 7B for human glioblastoma cells (U87MG); FIG. 7C shows a statistical comparison of each of the three concentrations of compound AP2-18 (8) tested vs the other compounds tested (ALA, ALA and CP94 (3), MAL, MAL and CP94 (3) and the other concentrations of AP2-18 (8)) (obtained by 1 way ANOVA with Tukey post-test comparing all pairs of columns).

FIG. 9 shows the mean PpIX fluorescence measured in A431 cells following increasing doses (250, 500 or 1000 μM) of ALA+/− CP94, MAL+/− CP94 and AP2-18 after incubation periods of A(i) 2 hours, B(i) 3 hours and C(i) 4 hours with the corresponding statistical analysis for each time period presented in A(ii), B(ii) and C(ii) respectively.

Figure 10A:
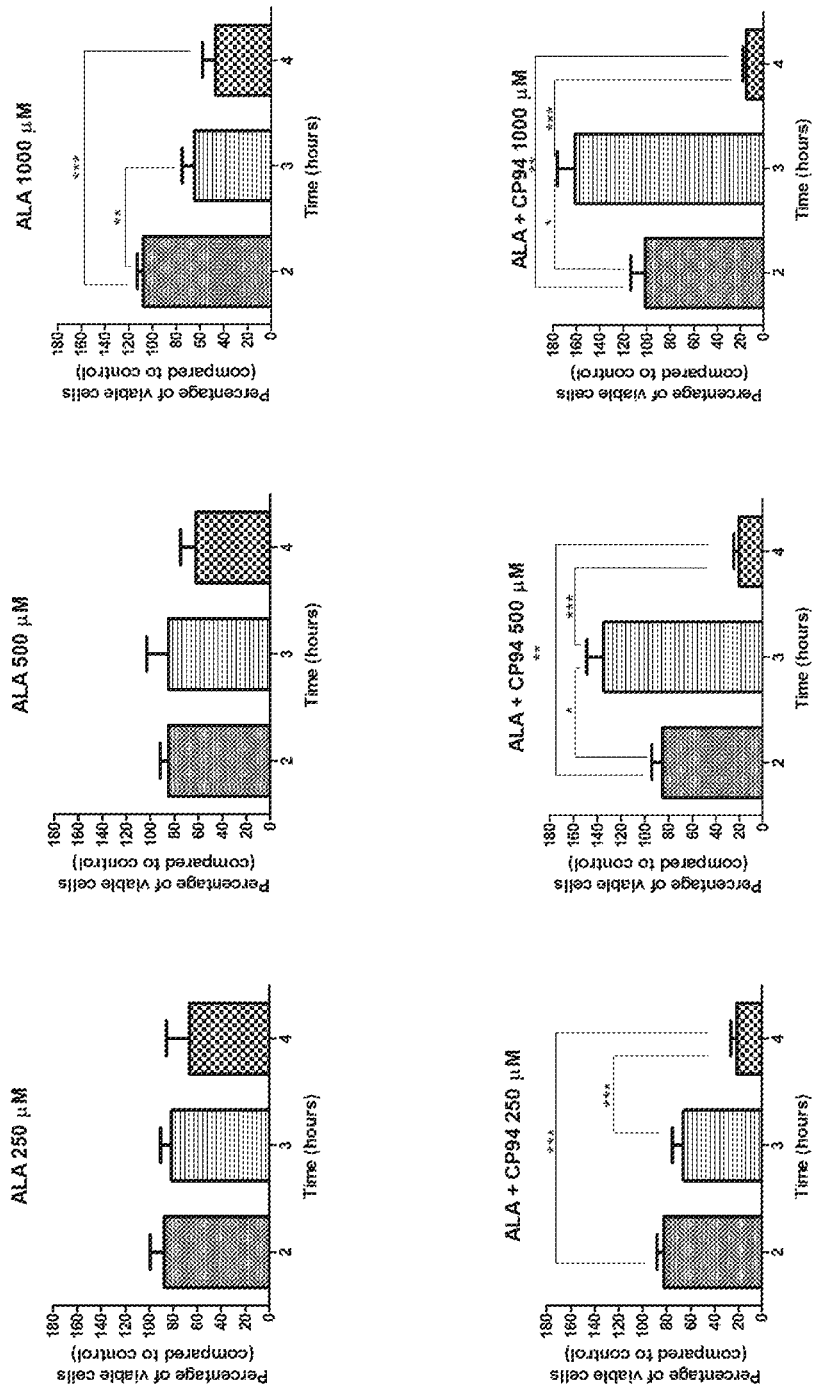
Figure 10B:
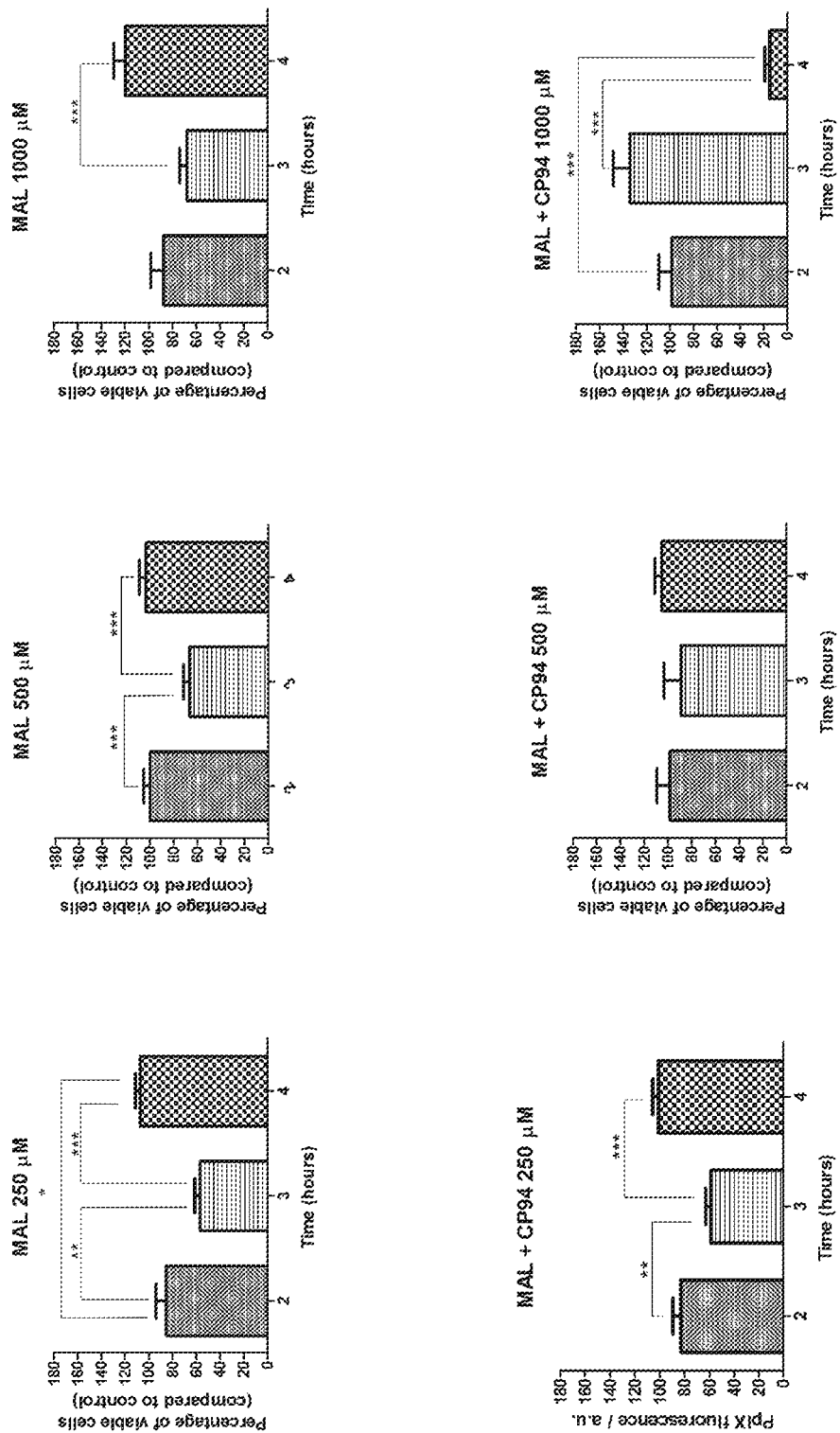
Figure 10C:
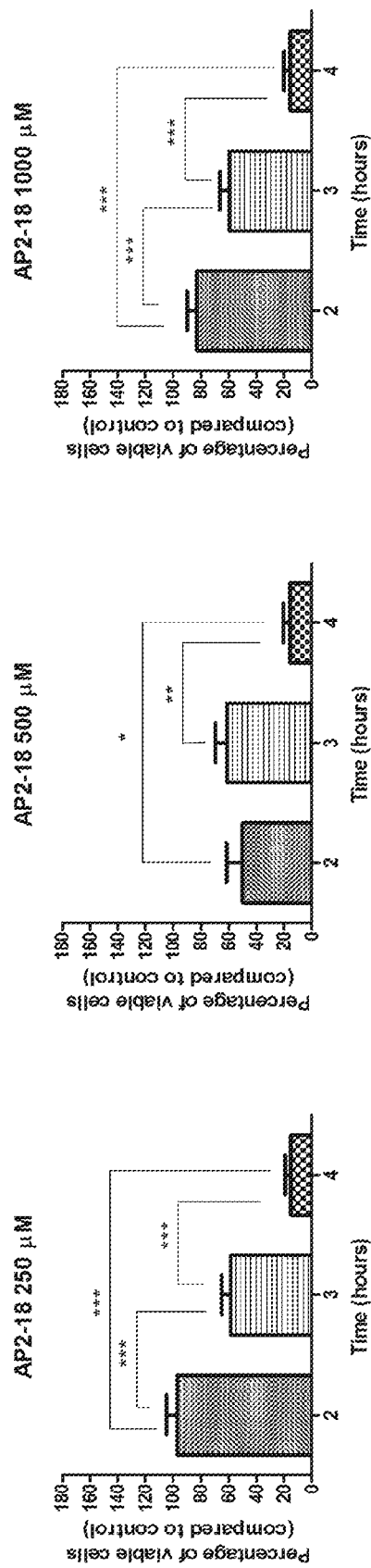

FIG. 10 shows the mean cell viability of A431 cells following increasing doses (250, 500 or 1000 mM) of (A) ALA+/− CP94, (B) MAL+/− CP94 and (C) AP2-18 after varying incubation periods (2, 3 or 4 hours); *,  and * indicates statistical significance at the 0.050, 0.010 and 0.001 levels respectively.

FIG. 11 shows the mean cell viability of A431 cells following increasing doses (250, 500 or 1000 mM) of ALA+/− CP94, MAL+/− CP94 and AP2-18 after incubation periods of A(i) 2 hours, B(i) 3 hours and C(i) 4 hours with the corresponding statistical analysis for each time period presented in A(ii), B(ii) and C(ii) respectively; DLI stands for 'drug-light interval', i.e. the incubation period during which the cells have been exposed to the drug before irradiation takes place.

EXAMPLES

Example 1

Synthesis of 1-(2-(5-amino-4-oxopentanoyloxy) ethyl)-2-ethyl-3,4-dihydroxypyridinium chloride hydrochloride (AP2-18), 8

Synthesis of AP2-18 (8) was achieved via the coupling of benyloxycarbonyl-protected aminolevulinic acid 5 with CP94 analogue 6.

ALA-derivative 5 was synthesised by exposure of ALA.HCl (4) (obtained from Sigma-Aldrich) to benzyl chloroformate, under basic conditions, to give benzyloxy-protected ALA 5.

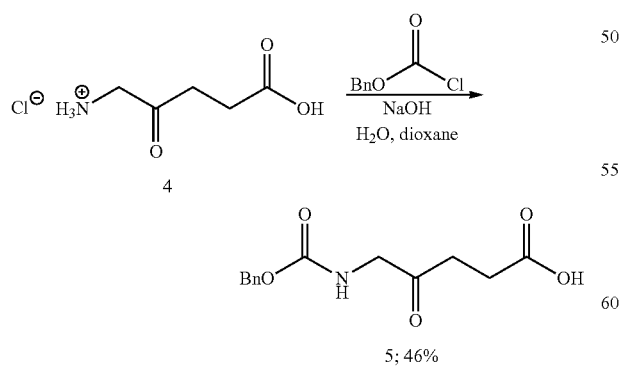

The complementary coupling partner, CP94 analogue 6, was synthesised from ethyl maltol (1) by benzyl protection then amination with ethanolamine.

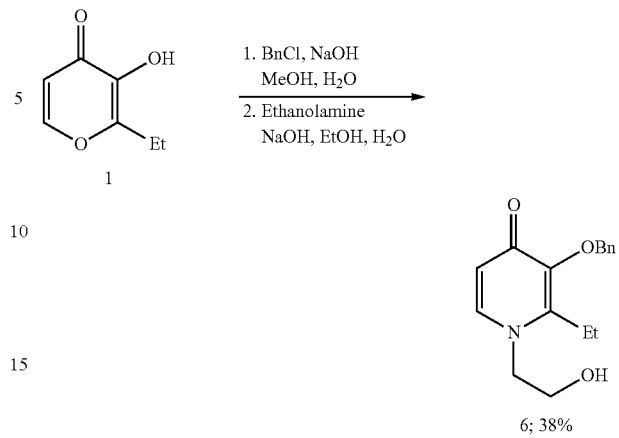

Esterification of 5 and 6, promoted by DCC/DMAP, proceeded smoothly to give the coupled product 7, which was deprotected by hydrogenolysis to give the target compound AP2-18 (8):

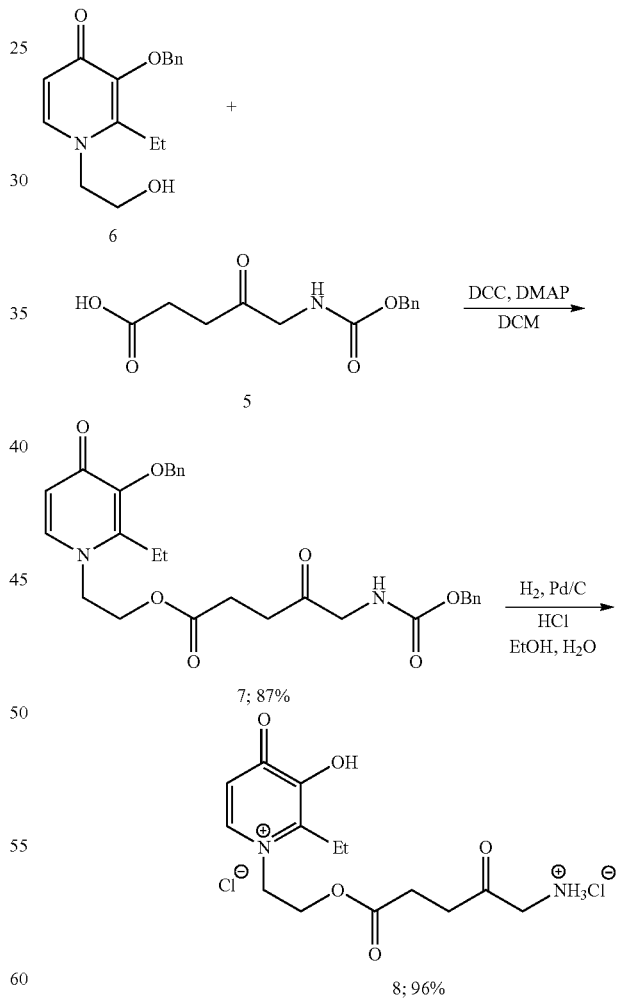

Compound AP2-18 (8) is a compound according to the first aspect of the invention, and corresponds to the salt of formula (Ic).

Full experimental procedures for these steps are given below.

1A. ALA-Derivative 5

ALA-derivative 5 is a known compound which can, for example, be obtained via the procedure in Neuberger A. et al., Biochemistry Journal, 1956, 64, 137-145.

1B. CP94 Analogue 6

CP94 analogue 6 was prepared according to a previously published procedure (Dobbin, P. S., et al., J Med Chem, 1993. 36(17): p. 2448-58; Liu, Z. D. et al., J. Pharm. Pharmacol, 1999, 51, 555-564.

1C. 2-(3-(Benzyloxy)-2-ethyl-4-oxopyridin-1(4H)-yl)ethyl 5-(benzyloxycarbonylamino)-4-oxopentanoate, 7

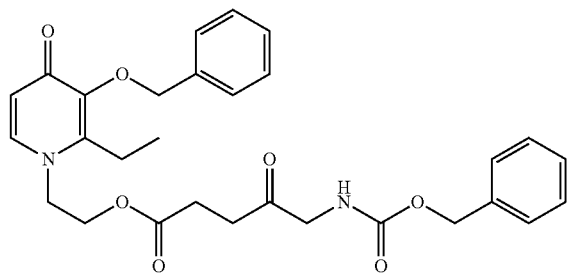 [SMILES: CCc1c(OCc2ccccc2)c(=O)ccn1CCOC(=O)CCC(=O)CNC(=O)OCc1ccccc1]

4-(Dimethylamino)pyridine (3.3 mg, 0.0274 mmol) was added to a stirred solution of 3-(benzyloxy)-2-ethyl-1-(2-hydroxyethyl)pyridin-4(1H)-one (6) (149 mg, 0.547 mmol), 5-(benzyloxycarbonylamino)-4-oxopentanoic acid (5) (145 mg, 0.547 mmol) and N,N'-dicyclohexylcarbodiimide (118 mg, 0.574 mmol) in dichloromethane (8 mL). After 24 h, the resulting suspension was filtered through cotton wool, eluting with dichloromethane. The filtrate was concentrated in vacuo and the residue was purified by flash chromatography on silica gel, eluting with ethyl acetate then methanol, to give the title compound 7 (247 mg, 87%) as a colourless oil, $R_F$ 0.7 (MeOH); $\delta_H$ (300 MHz; CDCl$_3$) 7.46-7.20 (11H, m, Ar and Pyr 6-H), 6.40 (1H, d, J 9.0 Hz, Pyr 5-H), 5.97 (1H, br s, NH), 5.22 (2H, s, PhCH$_2$), 5.09 (2H, s, PhCH$_2$), 4.22 (2H, t, J 6.0 Hz, OCH$_2$CH$_2$), 4.10-3.95 (4H, m, HNCH$_2$ and OCH$_2$CH$_2$), 2.71-2.50 (6H, m, CH$_3$CH$_2$ and C(O)CH$_2$CH$_2$) and 0.99 (3H, t, J 7.0 Hz, CH$_3$) $\delta_C$ (75 MHz; CDCl$_3$) 204.7, 174.3, 172.3, 156.9, 146.2, 139.4, 138.0, 136.8, 129.1, 128.9, 128.8, 128.7, 128.5, 128.4, 128.3, 117.8, 73.3, 67.3, 63.3, 51.5, 50.9, 34.4, 27.9, 19.8 and 13.5.

1D. 1-(2-(5-amino-4-oxopentanoyloxy)ethyl)-2-ethyl-3,4-dihydroxypyridinium chloride hydrochloride (AP2-18), 8

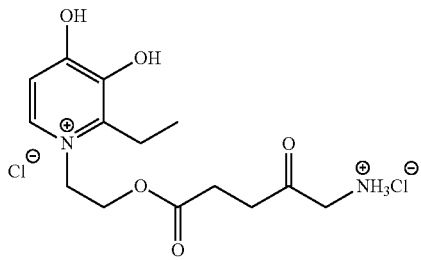

A stirred solution of 2-(3-(benzyloxy)-2-ethyl-4-oxopyridin-1(4H)-yl)ethyl 5-(benzyloxycarbonylamino)-4-oxopentanoate (7) (247 mg, 0.475 mmol) in 6:1 v/v ethanol:water (3.5 mL) was acidified to pH=1 by addition of hydrochloric acid (37% aq.). Palladium on activated charcoal (11 mg, 10% w/w) was added, the reaction vessel was evacuated then filled with hydrogen and the reaction was stirred under hydrogen (at atmospheric pressure) for 2 h. The resulting suspension was filtered through Celite®, eluting with ethanol and the filtrate was then concentrated in vacuo to give the product as a mixture of mono- and di-salts. Three cycles of dissolution in water, addition of hydrochloric acid (37% aq.) then concentration in vacuo gave the title compound 8 (169 mg, 96%) as a brown oil, $\delta_H$ (300 MHz; D$_2$O) 7.82 (1H, d, J 8.0 Hz, Ar 6-H), 6.92 (1H, d, J 8.0 Hz, Ar 5-H), 4.27 (2H, t, J 6.0 Hz, OCH$_2$CH$_2$), 3.91 (2H, s, H$_3$N$^+$CH$_2$), 3.74 (2H, t, J 6.0 Hz, OCH$_2$CH$_2$), 2.80 (2H, q, J 7.0 Hz, CH$_3$CH$_2$), 2.66 (2H, t, J 6.0 Hz, C(O)CH$_2$), 2.45 (2H, t, J 6.0 Hz, C(O)CH$_2$) and 0.98 ppm (3H, t, J 7.0 Hz, CH$_3$); $\delta_C$ (75 MHz; D$_2$O) 204.3, 176.9, 158.6, 147.7, 142.5, 139.5, 111.0, 60.6, 57.8, 47.3, 34.6, 27.6, 20.1 and 11.3 ppm; m/z (ES+) 297.1445 (100%, [M-H-2Cl]$^+$), C$_{14}$H$_{21}$N$_2$O$_5$ requires M, 297.1445.

Comparative Example 1

Synthesis of CP94 (3)

Compound CP94 (3) was prepared according to a previously published procedure (Dobbin, P. S., et al., J Med Chem, 1993. 36(17): p. 2448-58). Ethyl maltol (1) was benzyl protected and aminated to give 2; and deprotection by hydrogenolysis gave CP94 (3), as shown below.

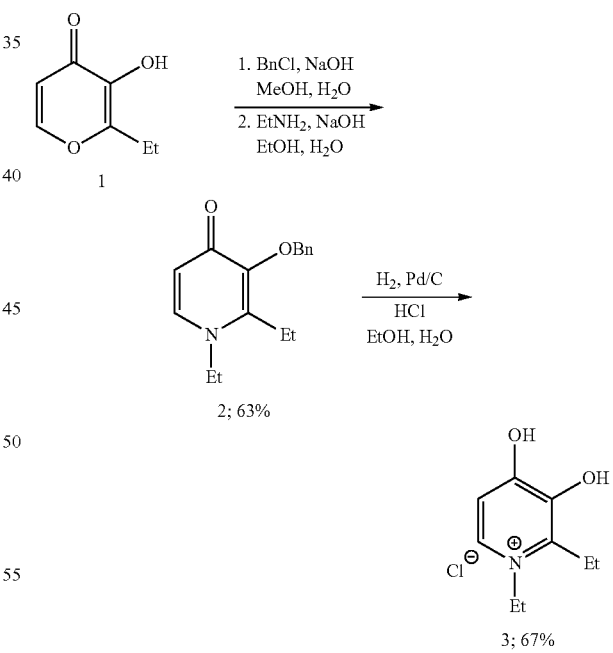

Example 2

Experimental Testing of AP2-18 (8)

NB: Unless otherwise stated all data presented is the mean of three independent experiments each consisting of three internal repeats of each condition.

2A. Toxicity Testing

To establish if compound AP2-18 (8) possessed any inherent toxic properties, a 1000 µM test solution was prepared (the highest concentration to be tested in this study) in standard cell culture medium (minimum essential medium (MEM) containing 1% (v/v) fetal bovine serum (FBS), 200 mM L-glutamine, 200 U mL$^{-1}$ penicillin and 200 µg mL$^{-1}$ streptomycin). This was applied to MRC-5 (human embryonic lung fibroblast) cells, under reduced light conditions, and left for 4 hours (this time period was chosen as it is equivalent to that used in dermatological PDT clinics) in the dark and following this cell viability was determined using the neutral red uptake (NRU) assay. Neutral red is an inert dye actively taken up and stored by viable (living) cells, an action which is unable to be performed by non-viable cells, therefore the level of neutral red taken up is directly proportional to the number of viable cells present following a given exposure. Following uptake of the dye, cells are lysed and the level of neutral red quantified using a plate reader.

Figure 1:
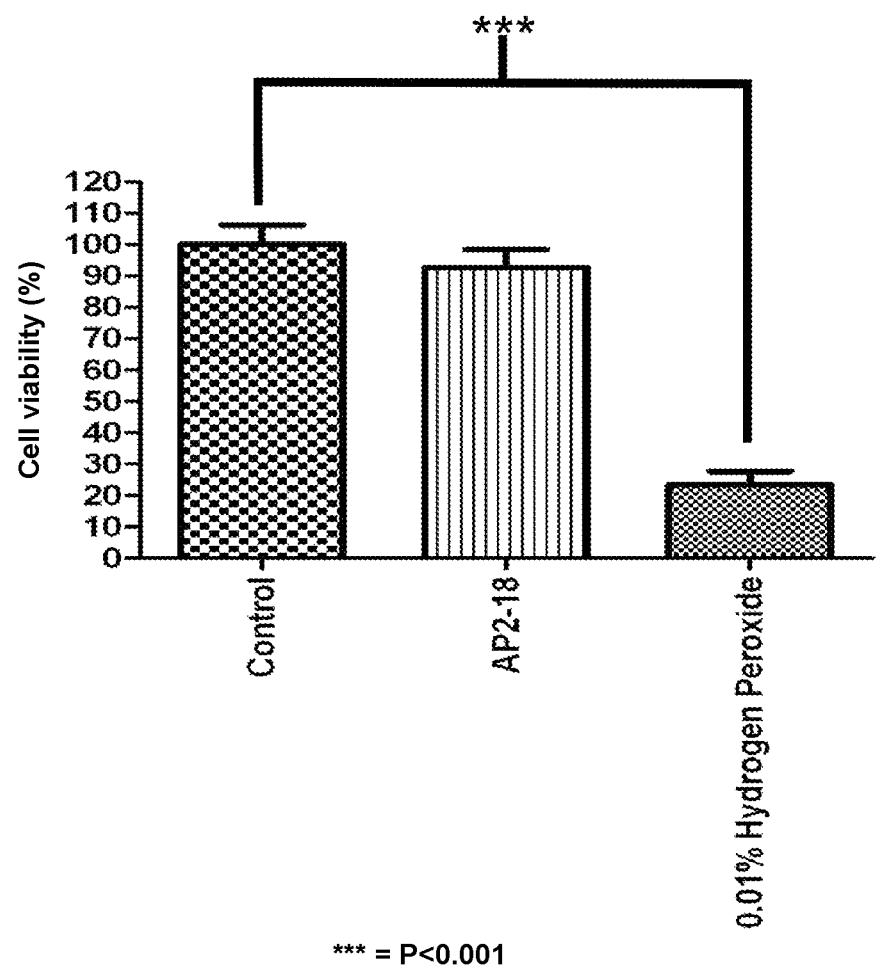
FIG. 1 shows the results from a neutral red uptake assay to assess the level of inherent (dark) toxicity possessed by compound AP2-18 (8); *** indicates significance at the P<0.001 level (student's t-test).

Control cells were incubated in standard cell culture medium. Cells were also exposed to 0.01% (v/v) hydrogen peroxide which acted as a positive control for the NRU assay. As can be seen from FIG. 1, exposure to 0.01% (v/v) hydrogen peroxide resulted in a significant reduction in cell viability. Treatment with AP2-18 (8) did result in a very slight reduction in the number of viable cells, however on statistical analysis this was not found to be significantly different to control cells incubated in standard cell culture medium. AP2-18 (8), therefore, is not inherently toxic to MRC-5 (lung fibroblast) cells when compared to cells only exposed to cell medium.

2B. PpIX Fluorescence Accumulation

The level of protoporphyrin IX (PpIX) accumulation was monitored using a well-established previously validated fluorescence based assay described in Blake, E. et al., Photochem Photobiol, 2011, 87(6), 1419-26; Blake, E. et al., Photochem Photobiol, 2010, 86(5), 1154-60; Curnow, A. et al., J Environ Pathol Toxicol Oncol, 2007, 26(2), 89-103; and Pye, A. et al., J Cancer Res Clin Oncol, 2008, 134(8), 841-9.

Briefly, cells were seeded at 2×10$^4$ cells per well in a 96 well plate and left to adhere overnight. Test solutions were prepared on the day of the assay and applied to the cells. The level of PpIX produced was monitored using a multi-well fluorescent plate reader with a 400 (±30) nm excitation filter and a 645 (±40) nm emission filter, with the level of fluorescence produced being directly proportional to the level of PpIX present. Readings were taken hourly for 6 hours and were conducted under low light conditions to reduce photobleaching of PpIX.

Figure 2A:
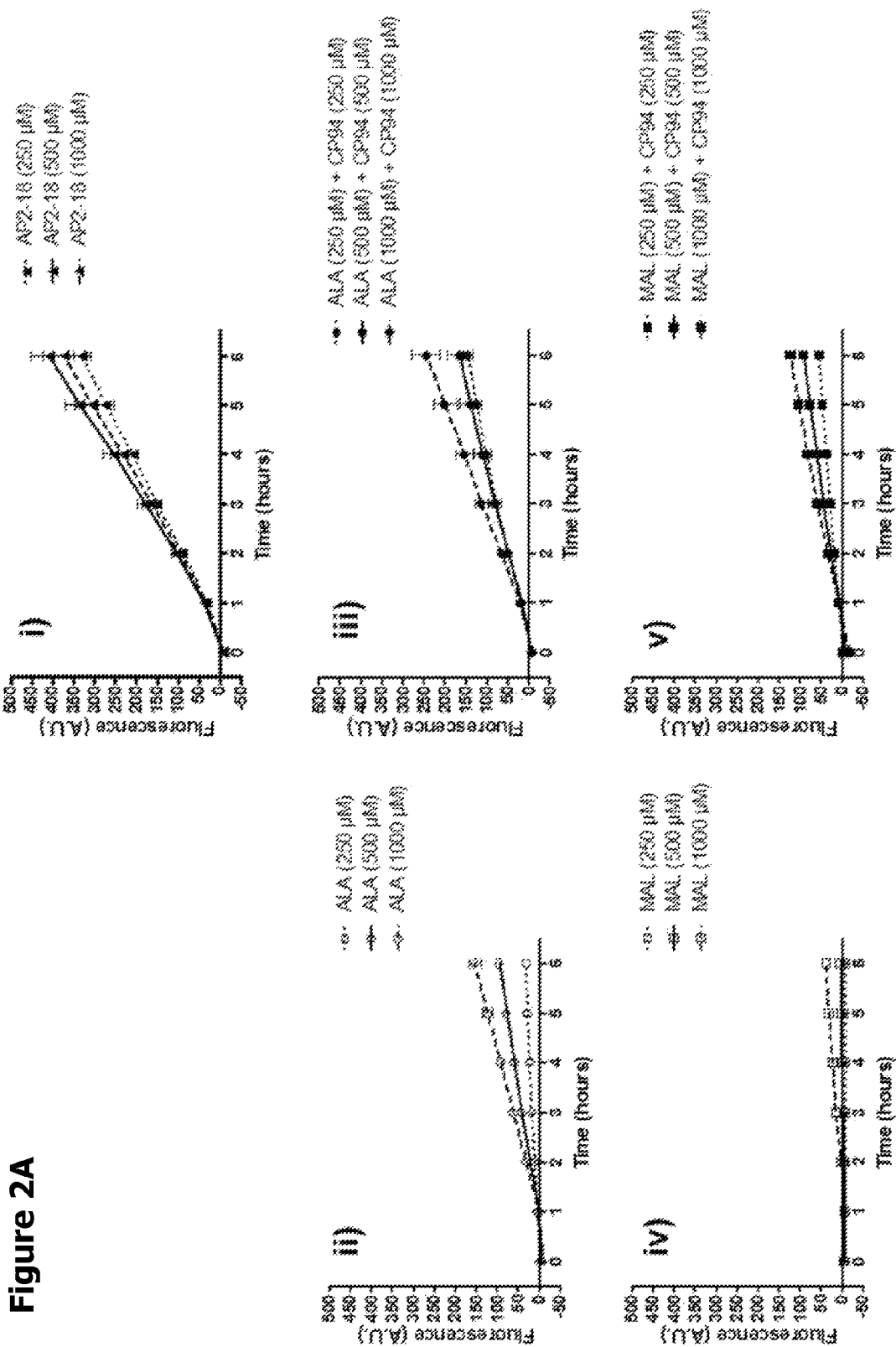
FIG. 2A shows the accumulation of PpIX fluorescence (+/− the standard error of the mean) in human dermal fibroblasts (84BR) over time following exposure to i) compound AP2-18 (8), ii) ALA alone, iii) ALA and CP94 (3), iv) MAL alone, and v) MAL and CP94 (3).
Figure 2B:
FIG. 2B shows the results of a statistical analysis of the PpIX accumulation data in Table 1 and FIG. 2A for human dermal fibroblasts (84BR)
Figure 3A:
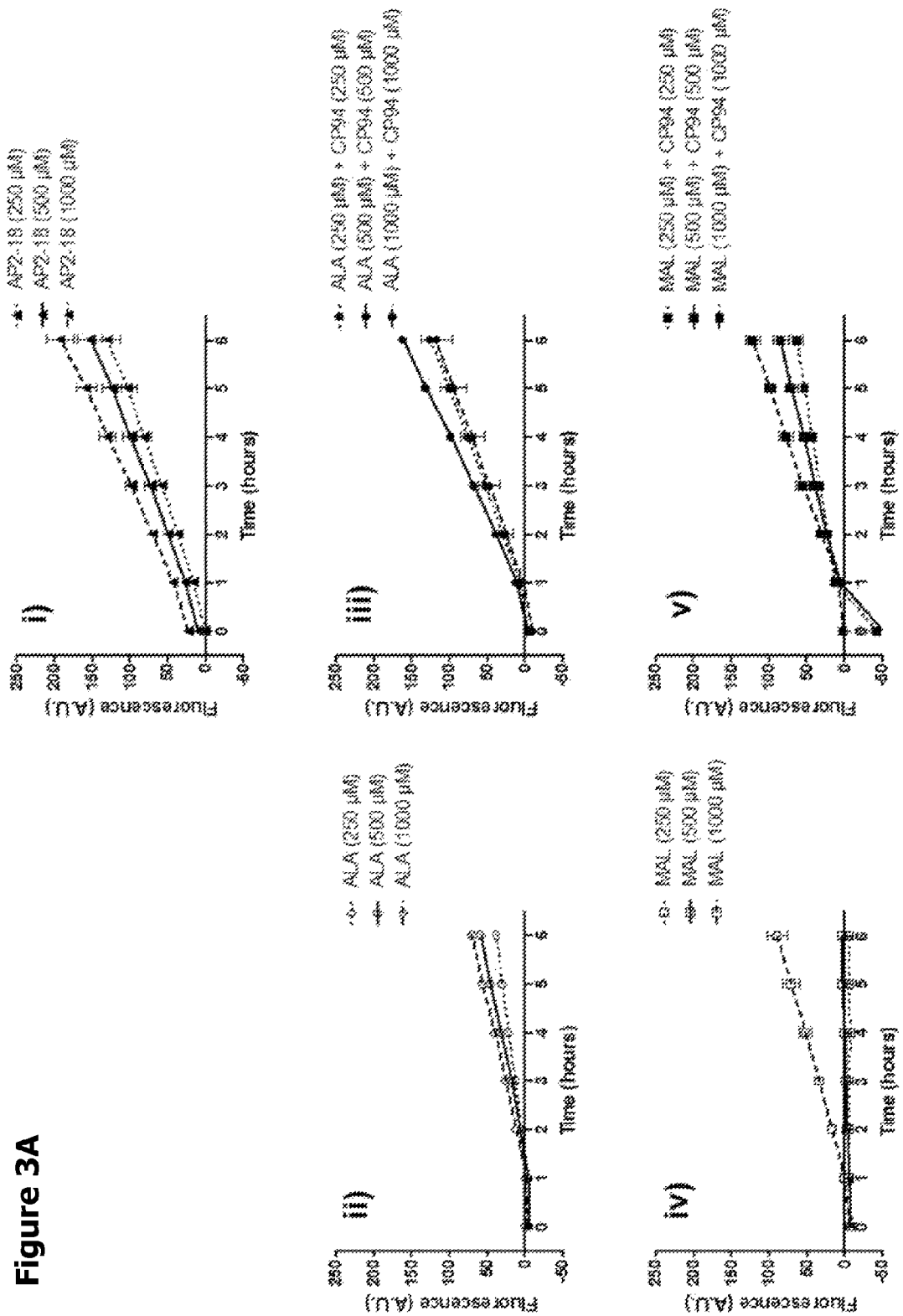
FIG. 3A shows the accumulation of PpIX fluorescence (+/− the standard error of the mean) in human epithelial squamous cell carcinoma cells (A431) over time following exposure to i) compound AP2-18 (8), ii) ALA alone, iii) ALA and CP94 (3), iv) MAL alone, and v) MAL and CP94 (3).
Figure 4A:
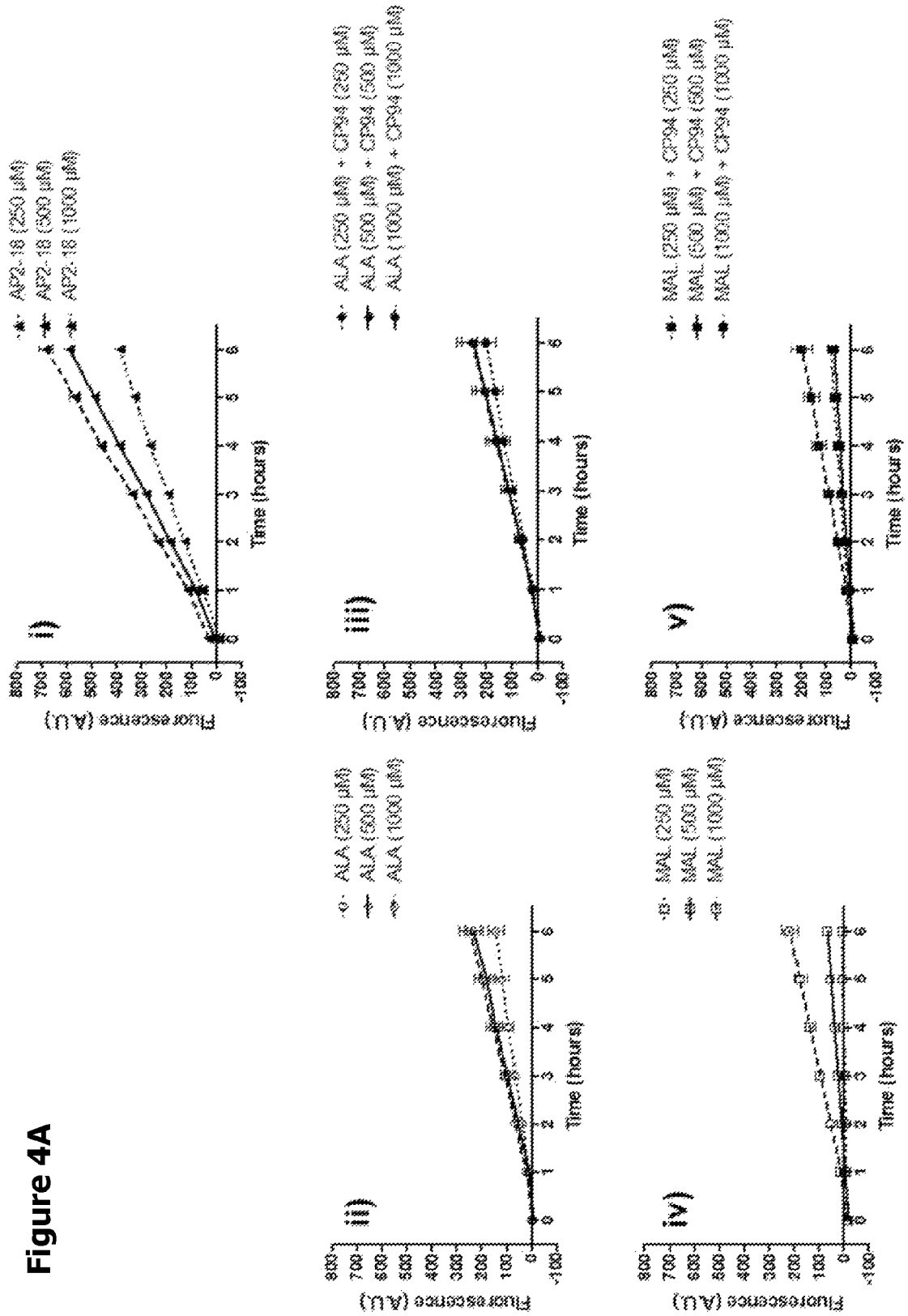
FIG. 4A shows the accumulation of PpIX fluorescence (+/− the standard error of the mean) in human glioblastoma cells (U87MG) over time following exposure to i) compound AP2-18 (8), ii) ALA alone, iii) ALA and CP94 (3), iv) MAL alone, and v) MAL and CP94 (3).

To evaluate the ability of AP2-18 (8) to cause an increase in PpIX accumulation within cells a series of concentrations were prepared (250 µM; 500 µM; 1000 µM) which reflect those previously used by our group (see citations mentioned above). These were tested alongside equimolar concentrations of ALA, ALA and CP94 (3), MAL, and MAL and CP94 (3), with all test compounds being investigated in human dermal fibroblasts (84BR; FIGS. 2A and 2B), human epithelial squamous cell carcinoma cells (A431; FIGS. 3A and 3B) and human glioblastoma cells (U87MG; FIGS. 4A and 4B).

The results are given in the tables below: Table 1 shows the results for the tests with human dermal fibroblasts (84BR) corresponding to FIGS. 2A and 2B; Table 2 shows the results for the tests with human epithelial squamous cell carcinoma cells (A431) corresponding to FIGS. 3A and 3B; and Table 3 shows the results for the tests with human glioblastoma cells (U87MG) corresponding to FIGS. 4A and 4B.

TABLE 1

PpIX accumulation in human dermal fibroblasts (84BR)

| Exposure Time (hours) | Drug | | | | | | | | |
|---|---|---|---|---|---|---|---|---|---|
| | ALA (250 µM) | | | | | | | | |
| 0 | 0 | −3 | −3 | −6.33 | −3.33 | −4.33 | 0.33 | 2.33 | 3.33 |
| 1 | 8.33 | 7.33 | 4.33 | −0.33 | 0.67 | 0.67 | 5 | 8 | 7 |
| 2 | 15 | 14 | 13 | 14.67 | 13.67 | 12.67 | 3 | 5 | 5 |
| 3 | 23 | 20 | 20 | 28 | 26 | 27 | 4.33 | 8.33 | 6.33 |
| 4 | 23 | 25 | 21 | 39.67 | 34.67 | 38.67 | 8 | 10 | 9 |
| 5 | 25 | 26 | 22 | 53 | 49 | 52 | 6.67 | 9.67 | 9.67 |
| 6 | 25.67 | 28.67 | 25.67 | 62.33 | 56.33 | 61.33 | 9.33 | 11.33 | 10.33 |
| | ALA (500 µM) | | | | | | | | |
| 0 | −1.33 | −9.33 | −5.33 | −9 | −4 | −6 | −2.67 | −4.67 | −15.67 |
| 1 | 9.33 | 5.33 | 5.33 | −1 | 1 | −1 | −4.67 | 8.33 | −3.67 |
| 2 | 29.67 | 25.67 | 23.67 | 25.67 | 25.67 | 23.67 | 8.33 | 21.33 | 8.33 |
| 3 | 51 | 52 | 48 | 50 | 51 | 48 | 20 | 36 | 19 |
| 4 | 66.67 | 67.67 | 64.67 | 74 | 73 | 70 | 37.67 | 55.67 | 35.67 |
| 5 | 84.33 | 87.33 | 85.33 | 99.33 | 97.33 | 93.33 | 50 | 68 | 48 |
| 6 | 97 | 108 | 105 | 122.33 | 119.33 | 115.33 | 63 | 81 | 59 |
| | ALA (1000 µM) | | | | | | | | |
| 0 | −2 | −11 | −11 | −4.67 | −4.67 | −3.67 | −8.33 | −9.33 | −8.33 |
| 1 | 12.67 | 9.67 | 7.67 | 0 | 4 | 8 | −4.33 | −1.33 | −1.33 |
| 2 | 48.67 | 43.67 | 41.67 | 31.33 | 37.33 | 44.33 | 13 | 14 | 12 |
| 3 | 85.67 | 81.67 | 80.67 | 65 | 73 | 84 | 35.33 | 35.33 | 30.33 |
| 4 | 117.67 | 115.67 | 113.67 | 95.67 | 105.67 | 115.67 | 57.33 | 56.33 | 47.33 |
| 5 | 154.67 | 154.67 | 149.67 | 131.33 | 142.33 | 158.33 | 79.33 | 77.33 | 69.33 |
| 6 | 186 | 191 | 186 | 163 | 175 | 195 | 104.33 | 100.33 | 89.33 |

TABLE 1-continued

PpIX accumulation in human dermal fibroblasts (84BR)

| Exposure Time (hours) | Drug | | | | | | | | |
|---|---|---|---|---|---|---|---|---|---|
| | ALA (250 µM) + CP94 (250 µM) | | | | | | | | |
| 0 | −4 | −5 | 0 | −9 | −4 | −12 | −6.33 | −5.33 | −5.33 |
| 1 | 29 | 28 | 27 | 16 | 15 | 13 | 11.67 | 13.67 | 11.67 |
| 2 | 62 | 64 | 66 | 52.33 | 48.33 | 46.33 | 34.67 | 37.67 | 36.67 |
| 3 | 95 | 99 | 102 | 84.67 | 76.67 | 74.67 | 52 | 58 | 56 |
| 4 | 121.33 | 126.33 | 129.33 | 114.33 | 100.33 | 99.33 | 71.33 | 77.33 | 73.33 |
| 5 | 150 | 155 | 155 | 141.33 | 126.33 | 124.33 | 85.67 | 91.67 | 89.67 |
| 6 | 172.67 | 179.67 | 185.67 | 169.33 | 149.33 | 147.33 | 102.33 | 107.33 | 103.33 |
| | ALA (500 µM) + CP94 (500 µM) | | | | | | | | |
| 0 | −0.33 | −3.33 | 4.67 | −18.67 | −7.67 | −8.67 | −7.67 | −1.67 | −0.67 |
| 1 | 40.33 | 38.33 | 35.33 | −8 | 0 | 4 | 10.33 | 14.33 | 16.33 |
| 2 | 87.33 | 89.33 | 87.33 | 7.33 | 20.33 | 24.33 | 40.67 | 46.67 | 48.67 |
| 3 | 134.67 | 145.67 | 138.67 | 17.67 | 34.67 | 46.67 | 71.67 | 74.67 | 77.67 |
| 4 | 177.33 | 190.33 | 181.33 | 24 | 50 | 61 | 102.33 | 105.33 | 107.33 |
| 5 | 224.67 | 241.67 | 230.67 | 31 | 62 | 78 | 128.67 | 131.67 | 136.67 |
| 6 | 265 | 284 | 274 | 35.67 | 71.67 | 94.67 | 155 | 155 | 159 |
| | ALA (1000 µM) + CP94 (1000 µM) | | | | | | | | |
| 0 | 1.67 | −0.33 | 3.67 | −10.67 | −8.67 | −7.67 | −19.67 | −19.67 | −12.67 |
| 1 | 50 | 40 | 39 | 20 | 23 | 20 | −1.67 | 1.33 | 6.33 |
| 2 | 101.33 | 101.33 | 95.33 | 70.67 | 73.67 | 70.67 | 17.67 | 29.67 | 35.67 |
| 3 | 169.33 | 167.33 | 158.33 | 122 | 123 | 119 | 39.33 | 55.33 | 65.33 |
| 4 | 226.33 | 224.33 | 210.33 | 170.67 | 171.67 | 162.67 | 58.33 | 78.33 | 91.33 |
| 5 | 292.67 | 287.67 | 270.67 | 222.67 | 224.67 | 212.67 | 77.33 | 101.33 | 116.33 |
| 6 | 360.67 | 352.67 | 330.67 | 268 | 273 | 259 | 98.33 | 126.33 | 136.33 |
| | MAL (250 µM) | | | | | | | | |
| 0 | −8.33 | −0.33 | 0.67 | −12.67 | −7.67 | −5.67 | −12.33 | −11.33 | −7.33 |
| 1 | 0 | 3 | 0 | −13 | −8 | −9 | −11 | −10 | −7 |
| 2 | −5.33 | −0.33 | −2.33 | −12 | −7 | −7 | −13 | −10 | −9 |
| 3 | −6.33 | −0.33 | −1.33 | −10.67 | −5.67 | −5.67 | −11 | −9 | −8 |
| 4 | −5 | −1 | −1 | −11 | −7 | −6 | −12 | −9 | −10 |
| 5 | −5 | 1 | 1 | −8.67 | −4.67 | −3.67 | −12.33 | −9.33 | −7.33 |
| 6 | −4 | 0 | −1 | −10 | −5 | −5 | −10 | −10 | −8 |
| | MAL (500 µM) | | | | | | | | |
| 0 | −11 | −8 | −4 | −10.33 | −7.33 | −2.33 | −23.67 | 1.33 | 14.33 |
| 1 | −8.67 | −6.67 | −6.67 | −11 | −11 | −11 | −21 | 2 | 6 |
| 2 | −8.67 | −4.67 | −0.67 | −4.33 | −4.33 | −4.33 | −18.33 | 1.67 | 5.67 |
| 3 | −6.33 | −3.33 | −0.33 | 2 | 2 | 2 | −18.67 | 2.33 | 3.33 |
| 4 | −5.67 | −0.67 | 1.33 | 1.33 | 4.33 | 4.33 | −12.33 | 3.67 | 9.67 |
| 5 | −3.67 | 1.33 | 0.33 | 9.67 | 9.67 | 9.67 | −7.67 | 5.33 | 7.33 |
| 6 | −4 | −1 | 1 | 10.67 | 11.67 | 11.67 | −4.33 | 8.67 | 10.67 |
| | MAL (1000 µM) | | | | | | | | |
| 0 | −2.33 | 8.67 | 7.67 | −23.67 | −17.67 | −17.67 | 5 | 14 | −7 |
| 1 | 1 | 7 | 6 | −22 | −11 | −22 | −9.33 | −2.33 | 0.67 |
| 2 | 8.67 | 14.67 | 14.67 | −8 | 4 | −6 | −5.67 | 2.33 | 3.33 |
| 3 | 16.33 | 22.33 | 20.33 | 11.67 | 21.67 | 19.67 | 2 | 10 | 9 |
| 4 | 21.33 | 23.33 | 27.33 | 27.67 | 36.67 | 33.67 | 9.33 | 14.33 | 14.33 |
| 5 | 29 | 28 | 32 | 39 | 51 | 49 | 14 | 23 | 20 |
| 6 | 34 | 32 | 38 | 53.33 | 62.33 | 63.33 | 14.67 | 26.67 | 20.67 |
| | MAL (250 µM) + CP94 (250 µM) | | | | | | | | |
| 0 | −0.33 | −2.33 | −3.33 | −12.33 | −7.33 | −3.33 | 5 | 5 | 5 |
| 1 | 16 | 12 | 9 | −2 | 2 | 3 | 12.67 | 10.67 | 13.67 |
| 2 | 28 | 27 | 23 | 9 | 14 | 15 | 19.33 | 17.33 | 22.33 |
| 3 | 37.33 | 37.33 | 35.33 | 18.67 | 25.67 | 26.67 | 24 | 24 | 30 |
| 4 | 48.33 | 48.33 | 44.33 | 27.33 | 32.33 | 34.33 | 33 | 31 | 37 |
| 5 | 60.33 | 59.33 | 56.33 | 39.67 | 43.67 | 46.67 | 38 | 35 | 43 |
| 6 | 74.33 | 68.33 | 66.33 | 47 | 54 | 52 | 43 | 42 | 51 |
| | MAL (500 µM) + CP94 (500 µM) | | | | | | | | |
| 0 | −11.67 | −6.67 | 3.33 | −12 | −8 | −10 | −4.67 | −1.67 | 0.33 |
| 1 | 16.33 | 16.33 | 15.33 | −2.33 | 1.67 | −0.33 | 4.67 | 8.67 | 10.67 |
| 2 | 35.67 | 37.67 | 39.67 | 19.67 | 24.67 | 17.67 | 21.67 | 24.67 | 25.67 |
| 3 | 58.33 | 59.33 | 62.33 | 40 | 40 | 35 | 32.67 | 33.67 | 40.67 |
| 4 | 77.33 | 78.33 | 79.33 | 54 | 54 | 48 | 45 | 48 | 53 |
| 5 | 103 | 101 | 103 | 72.33 | 71.33 | 62.33 | 59 | 59 | 66 |
| 6 | 123.67 | 120.67 | 121.67 | 83 | 85 | 77 | 70.67 | 68.67 | 76.67 |

TABLE 1-continued

PpIX accumulation in human dermal fibroblasts (84BR)

| Exposure Time (hours) | Drug | | | | | | | | |
|---|---|---|---|---|---|---|---|---|---|
| | MAL (1000 μM) + CP94 (1000 μM) | | | | | | | | |
| 0 | −6.67 | −12.67 | −16.67 | −34 | 0 | −8 | −16.33 | −16.33 | −20.33 |
| 1 | 16 | 20 | 12 | −11 | 10 | 11 | 5 | 10 | 0 |
| 2 | 46.67 | 45.67 | 37.67 | 14 | 35 | 34 | 30 | 51 | 31 |
| 3 | 79 | 76 | 68 | 34.33 | 50.33 | 52.33 | 47 | 77 | 55 |
| 4 | 107.67 | 105.67 | 93.67 | 52 | 67 | 67 | 69.33 | 103.33 | 78.33 |
| 5 | 140 | 139 | 120 | 66.67 | 78.67 | 81.67 | 85.67 | 127.67 | 94.67 |
| 6 | 170.67 | 164.67 | 150.67 | 87.67 | 88.67 | 92.67 | 103 | 152 | 113 |
| | AP2-18 (250 μM) | | | | | | | | |
| 0 | −11 | −11 | −7 | −12.33 | −10.33 | −14.33 | −1.67 | −4.67 | −2.67 |
| 1 | 28.67 | 30.67 | 33.67 | 16.67 | 19.67 | 17.67 | 49 | 40 | 46 |
| 2 | 84 | 73 | 89 | 70.33 | 68.33 | 73.33 | 119 | 108 | 115 |
| 3 | 143 | 123 | 152 | 124 | 124 | 126 | 194.67 | 179.67 | 183.67 |
| 4 | 191.67 | 166.67 | 203.67 | 174.67 | 174.67 | 181.67 | 272.67 | 255.67 | 261.67 |
| 5 | 245.33 | 216.33 | 263.33 | 228 | 231 | 237 | 354.33 | 335.33 | 343.33 |
| 6 | 302.33 | 262.33 | 321.33 | 283.33 | 282.33 | 288.33 | 422.67 | 396.67 | 406.67 |
| | AP2-18 (500 μM) | | | | | | | | |
| 0 | −8.33 | −6.33 | −7.33 | −12.33 | −11.33 | −12.33 | −3.33 | −1.33 | 0.67 |
| 1 | 34.67 | 33.67 | 35.67 | 20.67 | 17.67 | 11.67 | 62.67 | 55.67 | 53.67 |
| 2 | 101.67 | 96.67 | 99.67 | 77.33 | 65.33 | 57.33 | 165.67 | 144.67 | 139.67 |
| 3 | 169.67 | 160.67 | 168.67 | 142.33 | 118.33 | 105.33 | 276.33 | 236.33 | 231.33 |
| 4 | 236.67 | 223.67 | 231.67 | 205 | 171 | 149 | 391 | 336 | 329 |
| 5 | 311.33 | 293.33 | 304.33 | 269 | 223 | 197 | 522.33 | 450.33 | 440.33 |
| 6 | 387.67 | 363.67 | 374.67 | 332 | 275 | 240 | 627.67 | 543.67 | 529.67 |
| | AP2-18 (1000 μM) | | | | | | | | |
| 0 | −5.67 | −12.67 | −5.67 | −24.33 | −20.33 | −9.33 | −6.33 | −0.33 | −1.33 |
| 1 | 29.33 | 33.33 | 38.33 | −2.33 | 3.67 | 19.67 | 52.67 | 58.67 | 57.67 |
| 2 | 84.67 | 94.67 | 96.67 | 39 | 45 | 67 | 144.67 | 150.67 | 149.67 |
| 3 | 144.33 | 156.33 | 157.33 | 77.33 | 81.33 | 117.33 | 241.33 | 246.33 | 245.33 |
| 4 | 203.67 | 218.67 | 213.67 | 114 | 119 | 166 | 341.67 | 348.67 | 347.67 |
| 5 | 265.33 | 287.33 | 277.33 | 158 | 160 | 220 | 457 | 464 | 462 |
| 6 | 330.67 | 358.67 | 341.67 | 196.33 | 196.33 | 270.33 | 549 | 555 | 557 |

TABLE 2

PpIX accumulation in human epithelial squamous cell carcinoma cells (A431)-missing data is due to an infection present in these wells in this replicate and therefore data was discarded

| Exposure Time (hours) | Drug | | | | | |
|---|---|---|---|---|---|---|
| | ALA (250 μM) | | | | | |
| 0 | −9 | −5 | −4 | 2.67 | 2.67 | 7.67 |
| 1 | −6 | −3 | −2 | 1.67 | 1.67 | 4.67 |
| 2 | −1.33 | 1.67 | 3.67 | 10 | 9 | 11 |
| 3 | 3 | 8 | 8 | 18 | 19 | 18 |
| 4 | 13.33 | 17.33 | 17.33 | 28 | 28 | 28 |
| 5 | 20.33 | 26.33 | 26.33 | 35.67 | 36.67 | 35.67 |
| 6 | 26.33 | 32.33 | 30.33 | 44.67 | 47.67 | 44.67 |
| | ALA (500 μM) | | | | | |
| 0 | −16.67 | −15.67 | −19.67 | 5 | 2 | 10 |
| 1 | −15.33 | −13.33 | −15.33 | 7.33 | 3.33 | 7.33 |
| 2 | −3.67 | −1.67 | −2.67 | 15.33 | 12.33 | 19.33 |
| 3 | 7 | 9 | 6 | 27 | 24 | 32 |
| 4 | 22.67 | 25.67 | 27.67 | 38 | 36 | 43 |
| 5 | 39.67 | 42.67 | 45.67 | 49.33 | 49.33 | 51.33 |
| 6 | 52.33 | 55.33 | 61.33 | 61.67 | 62.67 | 62.67 |
| | ALA (1000 μM) | | | | | |
| 0 | −15.67 | −5.67 | 1.33 | 0.67 | −0.33 | −0.33 |
| 1 | −11 | −6 | 2 | 2.67 | 1.67 | 3.67 |
| 2 | 1.33 | 9.33 | 14.33 | 12.33 | 15.33 | 16.33 |
| 3 | 14.33 | 25.33 | 26.33 | 27.33 | 28.33 | 32.33 |
| 4 | 32.33 | 45.33 | 43.33 | 38.33 | 38.33 | 45.33 |

TABLE 2-continued

PpIX accumulation in human epithelial squamous cell carcinoma cells (A431)-
missing data is due to an infection present in these wells in this replicate and
therefore data was discarded

| Exposure Time (hours) | Drug | | | | | | | | |
|---|---|---|---|---|---|---|---|---|---|
| 5 | 50.67 | 63.67 | 60.67 | 51.67 | 54.67 | 57.67 | | | |
| 6 | 63 | 79 | 72 | 65 | 68 | 75 | | | |
| ALA (250 μM) + CP94 (250 μM) | | | | | | | | | |
| 0 | −7.33 | −7.33 | −11.33 | 1.33 | −0.67 | −3.67 | | | |
| 1 | 3 | 4 | 0 | 12 | 9 | 10 | | | |
| 2 | 26.67 | 24.67 | 19.67 | 37 | 34 | 39 | | | |
| 3 | 46 | 46 | 38 | 62 | 58 | 67 | | | |
| 4 | 70.67 | 71.67 | 61.67 | 87.33 | 77.33 | 89.33 | | | |
| 5 | 97.33 | 99.33 | 87.33 | 109 | 101 | 111 | | | |
| 6 | 118.33 | 121.33 | 110.33 | 135.33 | 128.33 | 140.33 | | | |
| ALA (500 μM) + CP94 (500 μM) | | | | | | | | | |
| 0 | −11.67 | −9.67 | −5.67 | 0 | 7 | 0 | | | |
| 1 | 9.67 | 6.67 | 9.67 | 11.33 | 16.33 | 14.33 | | | |
| 2 | 38.67 | 33.67 | 37.67 | 38 | 44 | 40 | | | |
| 3 | 69.33 | 61.33 | 69.33 | 68 | 73 | 71 | | | |
| 4 | 108 | 95 | 102 | 95 | 100 | 94 | | | |
| 5 | 145.67 | 131.67 | 140.67 | 123.67 | 127.67 | 121.67 | | | |
| 6 | 177.67 | 160.67 | 171.67 | 152 | 155 | 152 | | | |
| ALA (1000 μM) + CP94 (1000 μM) | | | | | | | | | |
| 0 | −19.33 | −15.33 | −19.33 | −4 | −2 | 2 | | | |
| 1 | −9 | −7 | −8 | 11.33 | 15.33 | 15.33 | | | |
| 2 | 4 | 4 | 5 | 45 | 46 | 50 | | | |
| 3 | 15.67 | 17.67 | 15.67 | 76.67 | 77.67 | 81.67 | | | |
| 4 | 35 | 34 | 38 | 103.67 | 100.67 | 110.67 | | | |
| 5 | 54.67 | 55.67 | 56.67 | 134.67 | 127.67 | 143.67 | | | |
| 6 | 68 | 71 | 75 | 163 | 159 | 171 | | | |
| MAL (250 μM) | | | | | | | | | |
| 0 | −10.67 | −3.67 | −2.67 | −5.33 | −8.33 | −10.33 | −12.33 | −15.33 | −20.33 |
| 1 | 3.67 | 3.67 | 5.67 | −0.33 | −3.33 | −7.33 | −9.67 | −9.67 | −14.67 |
| 2 | −5 | 0 | 1 | −0.33 | −5.33 | −6.33 | −11 | −10 | −16 |
| 3 | −4.67 | −0.67 | 1.33 | 0.67 | −3.33 | −7.33 | −11.67 | −9.67 | −14.67 |
| 4 | −4.67 | −2.67 | −2.67 | −2.67 | −3.67 | −8.67 | −11.67 | −10.67 | −15.67 |
| 5 | −3.67 | −1.67 | −0.67 | 1 | −3 | −6 | −11 | −8 | −16 |
| 6 | −3.33 | −2.33 | −2.33 | 4.33 | −2.67 | −6.67 | −13 | −12 | −16 |
| MAL (500 μM) | | | | | | | | | |
| 0 | −9.33 | −11.33 | −1.33 | −14 | −16 | −13 | 5.33 | −6.67 | 3.33 |
| 1 | −1 | −12 | −4 | −10.33 | −12.33 | −13.33 | 5.33 | −2.67 | 1.33 |
| 2 | −4.33 | −7.33 | 4.67 | −5.67 | −5.67 | −7.67 | 8.67 | −2.33 | 1.67 |
| 3 | −3.67 | −6.67 | 5.33 | −2.67 | 0.33 | −2.67 | 7.67 | −2.33 | 1.67 |
| 4 | −4.33 | −7.33 | 3.67 | 0.67 | 3.67 | 1.67 | 9 | 0 | 2 |
| 5 | −1.33 | −6.33 | 6.67 | 4.33 | 7.33 | 7.33 | 10.67 | 0.67 | 4.67 |
| 6 | −3.33 | −5.33 | 6.67 | 8 | 11 | 8 | 8.67 | 0.67 | 2.67 |
| MAL (1000 μM) | | | | | | | | | |
| 0 | −17.33 | −10.33 | −10.33 | −1.67 | 2.33 | 3.33 | | | |
| 1 | −3 | 2 | −1 | −0.33 | 2.67 | 1.67 | | | |
| 2 | 21 | 28 | 21 | 9.67 | 10.67 | 11.67 | | | |
| 3 | 45 | 50 | 42 | 22.67 | 25.67 | 20.67 | | | |
| 4 | 70 | 74 | 64 | 34.33 | 39.33 | 30.33 | | | |
| 5 | 97.67 | 99.67 | 88.67 | 47.33 | 53.33 | 42.33 | | | |
| 6 | 122.67 | 124.67 | 108.67 | 62.33 | 65.33 | 55.33 | | | |
| MAL (250 μM) + CP94 (250 μM) | | | | | | | | | |
| 0 | −5.67 | −8.67 | −4.67 | −127 | −127 | −127 | 6 | 11 | 3 |
| 1 | 27.67 | 15.67 | 17.67 | 5.67 | 5.67 | 9.67 | 13 | 15 | 5 |
| 2 | 36.33 | 30.33 | 35.33 | 16.67 | 14.67 | 20.67 | 10.33 | 23.33 | 13.33 |
| 3 | 51 | 42 | 50 | 28 | 24 | 31 | 21.33 | 30.33 | 19.33 |
| 4 | 65.67 | 53.67 | 61.67 | 35.67 | 34.67 | 39.67 | 27.33 | 37.33 | 26.33 |
| 5 | 77.67 | 63.67 | 74.67 | 49.33 | 47.33 | 52.33 | 33.33 | 45.33 | 34.33 |
| 6 | 95 | 80 | 92 | 54.33 | 55.33 | 60.33 | 39 | 51 | 38 |
| MAL (500 μM) + CP94 (500 μM) | | | | | | | | | |
| 0 | −11 | −16 | −12 | −134 | −134 | −134 | 0.33 | −5.67 | −4.67 |
| 1 | 18 | 13 | 15 | 10.33 | −1.67 | −6.67 | 6 | 2 | 0 |
| 2 | 38 | 33 | 39 | 31.33 | 19.33 | 7.33 | 17.67 | 16.67 | 14.67 |
| 3 | 57 | 54 | 61 | 54.33 | 40.33 | 19.33 | 26 | 27 | 24 |
| 4 | 73.67 | 72.67 | 79.67 | 68.33 | 55.53 | 27.33 | 39.33 | 36.33 | 33.33 |

TABLE 2-continued

PpIX accumulation in human epithelial squamous cell carcinoma cells (A431)-
missing data is due to an infection present in these wells in this replicate and
therefore data was discarded

| Exposure Time (hours) | Drug | | | | | | | | |
|---|---|---|---|---|---|---|---|---|---|
| 5 | 93.33 | 95.33 | 103.33 | 87 | 75 | 39 | 50.33 | 50.33 | 43.33 |
| 6 | 112.33 | 119.33 | 123.33 | 108.33 | 91.33 | 48.33 | 51.67 | 57.67 | 51.67 |
| | MAL (1000 μM) + CP94 (1000 μM) | | | | | | | | |
| 0 | −12.67 | −8.67 | −0.67 | 19.67 | 11.67 | 6.67 | | | |
| 1 | −6 | −2 | −2 | 26.67 | 16.67 | 10.67 | | | |
| 2 | 13 | 18 | 15 | 55.67 | 44.67 | 37.67 | | | |
| 3 | 34.33 | 40.33 | 40.33 | 82.67 | 74.67 | 63.67 | | | |
| 4 | 51.33 | 61.33 | 60.33 | 110.67 | 96.67 | 86.67 | | | |
| 5 | 76.33 | 84.33 | 86.33 | 114.67 | 117.67 | 111.67 | | | |
| 6 | 93.67 | 107.67 | 104.67 | 144 | 147 | 137 | | | |
| | AP2-18 (250 μM) | | | | | | | | |
| 0 | −1.33 | −1.33 | −3.33 | 0.67 | −1.33 | −3.33 | 9.67 | 5.67 | 5.67 |
| 1 | 6.33 | 5.33 | 6.33 | 20.67 | 19.67 | 17.67 | 23 | 23 | 22 |
| 2 | 20.33 | 17.33 | 19.33 | 43.67 | 42.67 | 41.67 | 44.67 | 54.67 | 48.67 |
| 3 | 32 | 30 | 30 | 72.33 | 69.33 | 69.33 | 67 | 80 | 79 |
| 4 | 42.33 | 42.33 | 46.33 | 100.33 | 96.33 | 97.33 | 89.67 | 111.67 | 111.67 |
| 5 | 53.67 | 52.67 | 57.67 | 127.67 | 120.67 | 120.67 | 113.67 | 144.67 | 141.67 |
| 6 | 71.33 | 65.33 | 71.33 | 152.33 | 143.33 | 145.33 | 150.67 | 186.67 | 181.67 |
| | AP2-18 (500 μM) | | | | | | | | |
| 0 | 10.67 | 10.67 | 9.67 | 9.67 | 1.67 | 5.67 | 19.67 | 11.67 | 13.67 |
| 1 | 21.33 | 21.33 | 21.33 | 33.67 | 22.67 | 28.67 | 33 | 32 | 29 |
| 2 | 34.33 | 35.33 | 33.33 | 57.67 | 49.67 | 55.67 | 58.67 | 69.67 | 58.67 |
| 3 | 46 | 50 | 46 | 86.33 | 78.33 | 85.33 | 89 | 101 | 85 |
| 4 | 59.33 | 67.33 | 62.33 | 114.33 | 109.33 | 114.33 | 119.67 | 139.67 | 118.67 |
| 5 | 71.67 | 82.67 | 73.67 | 137.67 | 136.67 | 140.67 | 151.67 | 177.67 | 146.67 |
| 6 | 88.33 | 99.33 | 95.33 | 163.33 | 158.33 | 164.33 | 196.67 | 226.67 | 188.67 |
| | AP2-18 (1000 μM) | | | | | | | | |
| 0 | 26.67 | 22.67 | 34.67 | 9.67 | 9.67 | 16.67 | 31.67 | 28.67 | 29.67 |
| 1 | 41.33 | 38.33 | 49.33 | 33.67 | 34.67 | 36.67 | 49 | 51 | 51 |
| 2 | 58.33 | 58.33 | 69.33 | 58.67 | 58.67 | 63.67 | 78.67 | 97.67 | 93.67 |
| 3 | 76 | 79 | 92 | 89.33 | 86.33 | 88.33 | 109 | 135 | 134 |
| 4 | 96.33 | 100.33 | 116.33 | 117.33 | 114.33 | 118.33 | 144.67 | 180.67 | 182.67 |
| 5 | 113.67 | 119.67 | 140.67 | 145.67 | 139.67 | 141.67 | 177.67 | 221.67 | 225.67 |
| 6 | 136.33 | 147.33 | 168.33 | 167.33 | 163.33 | 164.33 | 226.67 | 276.67 | 286.67 |

TABLE 3

PpIX accumulation in human glioblastoma cells (U87MG)

| Exposure Time (hours) | Drug | | | | | | | | |
|---|---|---|---|---|---|---|---|---|---|
| | ALA (250 μM) | | | | | | | | |
| 0 | −1.33 | −0.33 | −1.33 | −2.33 | −4.33 | −2.33 | −3 | −5 | −4 |
| 1 | 6.67 | 6.67 | 6.67 | 26.67 | 21.67 | 27.67 | 0 | 0 | 1 |
| 2 | 27.67 | 24.67 | 24.67 | 71 | 66 | 77 | 14.67 | 13.67 | 15.67 |
| 3 | 44.33 | 43.33 | 45.33 | 120 | 114 | 132 | 27.67 | 26.67 | 28.67 |
| 4 | 67 | 63 | 67 | 173.33 | 164.33 | 190.33 | 42.33 | 42.33 | 44.33 |
| 5 | 84.33 | 82.33 | 84.33 | 213 | 203 | 230 | 54.67 | 53.67 | 56.67 |
| 6 | 102 | 100 | 102 | 258 | 250 | 281 | 69 | 69 | 70 |
| | ALA (500 μM) | | | | | | | | |
| 0 | −11 | −10 | −13 | −5.33 | −3.33 | −3.33 | −3.67 | −5.67 | −5.67 |
| 1 | 4.33 | 6.33 | 5.33 | 29.33 | 36.33 | 33.33 | 5.67 | 6.67 | 2.67 |
| 2 | 40.33 | 42.33 | 43.33 | 81.33 | 97.33 | 91.33 | 28 | 28 | 26 |
| 3 | 76.33 | 79.33 | 80.33 | 144.33 | 164.33 | 153.33 | 55.67 | 53.67 | 49.67 |
| 4 | 118.33 | 122.33 | 125.33 | 212 | 248 | 230 | 76.33 | 78.33 | 73.33 |
| 5 | 159.67 | 163.67 | 170.67 | 269.67 | 306.67 | 285.67 | 101.33 | 103.33 | 95.33 |
| 6 | 202 | 202 | 211 | 345.33 | 389.33 | 366.33 | 128 | 129 | 119 |
| | ALA (1000 μM) | | | | | | | | |
| 0 | −8 | −9 | −1 | −6.33 | −4.33 | 2.67 | −5 | −5 | −6 |
| 1 | 15.67 | 14.67 | 18.67 | 43 | 42 | 43 | 7 | 7 | 8 |
| 2 | 53.33 | 56.33 | 60.33 | 113 | 106 | 105 | 26 | 31 | 29 |
| 3 | 93.67 | 93.67 | 99.67 | 188 | 178 | 169 | 49 | 54 | 52 |

TABLE 3-continued

PpIX accumulation in human glioblastoma cells (U87MG)

| Exposure Time (hours) | | | | Drug | | | | | |
|---|---|---|---|---|---|---|---|---|---|
| 4 | 135 | 141 | 144 | 266.33 | 258.33 | 245.33 | 67.67 | 74.67 | 73.67 |
| 5 | 181.67 | 187.67 | 189.67 | 329.33 | 319.33 | 304.33 | 90.67 | 99.67 | 95.67 |
| 6 | 224.67 | 229.67 | 232.67 | 414.33 | 404.33 | 381.33 | 114.33 | 123.33 | 117.33 |
| ALA (250 μM) + CP94 (250 μM) | | | | | | | | | |
| 0 | −2.67 | −5.67 | −8.67 | −5 | −7 | −12 | −8.33 | −6.33 | −6.33 |
| 1 | 18.67 | 14.67 | 12.67 | 33 | 33 | 30 | 5.33 | 6.33 | 6.33 |
| 2 | 47.67 | 49.67 | 43.67 | 86.33 | 94.33 | 92.33 | 26.67 | 30.67 | 31.67 |
| 3 | 77.33 | 78.33 | 68.33 | 148.67 | 162.67 | 158.67 | 44.67 | 54.67 | 51.67 |
| 4 | 107.33 | 111.33 | 92.33 | 213 | 239 | 226 | 61.67 | 70.67 | 70.67 |
| 5 | 139.33 | 142.33 | 118.33 | 262 | 297 | 278 | 79 | 88 | 90 |
| 6 | 165 | 170 | 144 | 325.33 | 363.33 | 341.33 | 97.67 | 108.67 | 107.67 |
| ALA (500 μM) + CP94 (500 μM) | | | | | | | | | |
| 0 | −4 | 0 | 0 | −18.33 | −14.33 | −11.33 | −3.67 | −7.67 | −4.67 |
| 1 | 25.33 | 19.33 | 15.33 | 36 | 43 | 44 | 11.67 | 11.67 | 11.67 |
| 2 | 67.67 | 50.67 | 42.67 | 104 | 121 | 118 | 38.67 | 36.67 | 38.67 |
| 3 | 105.67 | 81.67 | 67.67 | 180.67 | 201.67 | 197.67 | 63.67 | 62.67 | 64.67 |
| 4 | 154.67 | 116.67 | 96.67 | 263.67 | 292.67 | 282.67 | 87.33 | 81.33 | 84.33 |
| 5 | 201.67 | 154.67 | 130.67 | 333.33 | 361.33 | 348.33 | 112.67 | 110.67 | 110.67 |
| 6 | 245.33 | 188.33 | 156.33 | 418 | 446 | 438 | 137.33 | 133.33 | 136.33 |
| ALA (1000 μM) + CP94 (1000 μM) | | | | | | | | | |
| 0 | −10.67 | −10.67 | −15.67 | −18.67 | −17.67 | −16.67 | −8.67 | −9.67 | −9.67 |
| 1 | 3.67 | 12.67 | 13.67 | 58.67 | 45.67 | 59.67 | 8.67 | 3.67 | 1.67 |
| 2 | 25 | 49 | 47 | 146.33 | 122.33 | 154.33 | 33.67 | 30.67 | 24.67 |
| 3 | 44 | 77 | 77 | 243 | 205 | 248 | 56.33 | 53.33 | 45.33 |
| 4 | 69.67 | 114.67 | 116.67 | 340 | 294 | 349 | 78 | 73 | 63 |
| 5 | 95.67 | 152.67 | 154.67 | 413 | 360 | 419 | 102.67 | 93.67 | 83.67 |
| 6 | 118.67 | 185.67 | 189.67 | 509.67 | 448.67 | 516.67 | 123.33 | 114.33 | 103.33 |
| MAL (250 μM) | | | | | | | | | |
| 0 | −11.33 | −1.33 | −2.33 | −20 | −21 | −22 | −12.67 | −12.67 | −10.67 |
| 1 | 4 | −7 | 11 | −14 | −16 | −15 | −10 | −7 | −7 |
| 2 | 2.67 | −2.33 | 4.67 | −10.67 | −12.67 | −14.67 | −10.67 | −8.67 | −7.67 |
| 3 | 8 | 6 | 12 | −6.67 | −10.67 | −9.67 | −9.33 | −7.33 | −9.33 |
| 4 | 16.67 | 13.67 | 20.67 | −5.33 | −6.33 | −6.33 | −9.33 | −6.33 | −7.33 |
| 5 | 27.33 | 22.33 | 29.33 | 1 | 0 | −2 | −9 | −7 | −9 |
| 6 | 32 | 25 | 34 | 1.67 | 4.67 | −1.33 | −9.67 | −6.67 | −7.67 |
| MAL (500 μM) | | | | | | | | | |
| 0 | −11 | −23 | −21 | −25.67 | −22.67 | −26.67 | −5 | −10 | −3 |
| 1 | 23.33 | 10.33 | 6.33 | −20 | −16 | −17 | 2 | −4 | 1 |
| 2 | 40.33 | 33.33 | 29.33 | −5 | −4 | −4 | 7 | 1 | 7 |
| 3 | 70 | 60 | 53 | 7 | 11 | 10 | 13 | 11 | 12 |
| 4 | 96 | 82 | 74 | 15 | 21 | 19 | 22.33 | 21.33 | 19.33 |
| 5 | 123.67 | 108.67 | 98.67 | 27.33 | 33.33 | 33.33 | 29.67 | 28.67 | 22.67 |
| 6 | 149 | 129 | 117 | 39.33 | 47.33 | 44.33 | 35 | 31 | 27 |
| MAL (1000 μM) | | | | | | | | | |
| 0 | −7.67 | −5.67 | −6.67 | −25.67 | −19.67 | −2.67 | −7.33 | −9.33 | −1.33 |
| 1 | 20.67 | 21.67 | 19.67 | 14 | 17 | 37 | 2 | 1 | 11 |
| 2 | 67 | 70 | 64 | 69.33 | 72.33 | 87.33 | 24.33 | 22.33 | 27.33 |
| 3 | 107.33 | 109.33 | 103.33 | 137.33 | 135.33 | 147.33 | 42.33 | 41.33 | 49.33 |
| 4 | 148.67 | 151.67 | 143.67 | 204 | 204 | 210 | 59.67 | 60.67 | 67.67 |
| 5 | 190.67 | 192.67 | 186.67 | 259.33 | 255.33 | 259.33 | 79.33 | 78.33 | 89.33 |
| 6 | 232.33 | 231.33 | 223.33 | 334.33 | 325.33 | 324.33 | 101.67 | 97.67 | 112.67 |
| MAL (250 μM) + CP94 (250 μM) | | | | | | | | | |
| 0 | −0.33 | −14.33 | −5.33 | −19.67 | −22.67 | −21.67 | 0.67 | 9.67 | 5.67 |
| 1 | 44 | 32 | 26 | −13 | −4 | −5 | 11.67 | 19.67 | 14.67 |
| 2 | 72 | 58 | 50 | 5.33 | 4.33 | 2.33 | 17.67 | 30.67 | 23.67 |
| 3 | 95.67 | 86.67 | 68.67 | 15.67 | 14.67 | 12.67 | 23.67 | 36.67 | 28.67 |
| 4 | 120 | 115 | 88 | 21 | 23 | 19 | 33.67 | 43.67 | 35.67 |
| 5 | 148.67 | 142.67 | 109.67 | 33.33 | 35.33 | 32.33 | 36.33 | 50.33 | 44.33 |
| 6 | 164.33 | 166.33 | 128.33 | 39.67 | 41.67 | 38.67 | 43.33 | 54.33 | 44.33 |
| MAL (500 μM) + CP94 (500 μM) | | | | | | | | | |
| 0 | 8.33 | −19.67 | −19.67 | −6.33 | −10.33 | −27.33 | 9 | 1 | 1 |
| 1 | 21.33 | −0.67 | 1.33 | 1.67 | 0.67 | −7.33 | 9.67 | 20.67 | 15.67 |
| 2 | 22.67 | 3.67 | 11.67 | 22 | 19 | 15 | 15 | 36 | 33 |
| 3 | 37.67 | 14.67 | 23.67 | 40 | 36 | 35 | 19.33 | 45.33 | 43.33 |

TABLE 3-continued

PpIX accumulation in human glioblastoma cells (U87MG)

| Exposure Time (hours) | Drug | | | | | | | | |
|---|---|---|---|---|---|---|---|---|---|
| 4 | 50 | 24 | 34 | 58.67 | 50.67 | 48.67 | 29.67 | 54.67 | 54.67 |
| 5 | 65.33 | 33.33 | 47.33 | 78 | 70 | 63 | 35.33 | 63.33 | 67.33 |
| 6 | 78.67 | 43.67 | 56.67 | 94.67 | 82.67 | 81.67 | 40 | 70 | 76 |
| MAL (1000 μM) + CP94 (1000 μM) | | | | | | | | | |
| 0 | −6 | −6 | −3 | 1.33 | 5.33 | 4.33 | −3 | −3 | −3 |
| 1 | 2.67 | 4.67 | 2.67 | 54.33 | 52.33 | 39.33 | 7 | 11 | 6 |
| 2 | 30 | 31 | 28 | 120.67 | 113.67 | 82.67 | 28.33 | 33.33 | 31.33 |
| 3 | 57.67 | 56.67 | 45.67 | 192.67 | 179.67 | 131.67 | 47.33 | 59.33 | 50.33 |
| 4 | 80 | 83 | 72 | 270 | 253 | 186 | 62 | 82 | 73 |
| 5 | 107.33 | 114.33 | 93.33 | 325.67 | 305.67 | 226.67 | 78.67 | 101.67 | 93.67 |
| 6 | 135.33 | 141.33 | 113.33 | 407.67 | 379.67 | 284.67 | 101.33 | 124.33 | 117.33 |
| AP2-18 (250 μM) | | | | | | | | | |
| 0 | 5.3 | −1.7 | −111.7 | −6.67 | −4.67 | 0 | −1.33 | 8.67 | 0 |
| 1 | 50.3 | 57.3 | 66.3 | 53.67 | 50.67 | 55.67 | 57.33 | 52.33 | 56.33 |
| 2 | 114.3 | 128.3 | 146.3 | 125.67 | 126.67 | 129.67 | 130.67 | 128.67 | 129.67 |
| 3 | 172 | 199 | 221 | 195 | 196 | 199 | 189.33 | 195.33 | 184.33 |
| 4 | 230 | 267 | 308 | 268 | 270 | 275 | 254 | 273 | 253 |
| 5 | 293.7 | 331.7 | 383.7 | 319 | 326 | 328 | 313.67 | 346.67 | 308.67 |
| 6 | 346.3 | 373.3 | 437.3 | 370 | 371 | 380 | 388.33 | 447.33 | 379.33 |
| AP2-18 (500 μM) | | | | | | | | | |
| 0 | 9.3 | 9.3 | 12.3 | 2.33 | −1.67 | 7.33 | 1.67 | 5.67 | 8.67 |
| 1 | 101.3 | 96.3 | 88.3 | 79.67 | 71.67 | 96.67 | 66.33 | 74.33 | 77.33 |
| 2 | 211.3 | 203.3 | 180.3 | 181.67 | 168.67 | 207.67 | 166.67 | 176.67 | 182.67 |
| 3 | 312 | 308 | 267 | 279 | 267 | 308 | 251.33 | 271.33 | 273.33 |
| 4 | 421 | 417 | 371 | 392 | 380 | 425 | 353 | 374 | 373 |
| 5 | 540.7 | 526.7 | 470.7 | 473 | 455 | 506 | 460.67 | 479.67 | 480.67 |
| 6 | 655.3 | 637.3 | 561.3 | 555 | 538 | 581 | 582.33 | 610.33 | 599.33 |
| AP2-18 (1000 μM) | | | | | | | | | |
| 0 | 46.3 | 31.3 | 46.3 | 14.33 | 17.33 | 24.33 | 39.67 | 21.67 | 28.67 |
| 1 | 144.3 | 126.3 | 107.3 | 100.67 | 104.67 | 112.67 | 116.33 | 101.33 | 119.33 |
| 2 | 271.3 | 242.3 | 194.3 | 217.67 | 219.67 | 228.67 | 245.67 | 229.67 | 258.67 |
| 3 | 386 | 351 | 270 | 320 | 337 | 341 | 354.33 | 333.33 | 369.33 |
| 4 | 519 | 469 | 361 | 447 | 468 | 469 | 478 | 456 | 499 |
| 5 | 642.7 | 580.7 | 436.7 | 534 | 546 | 559 | 601.67 | 581.67 | 633.67 |
| 6 | 762.3 | 688.3 | 528.3 | 623 | 650 | 651 | 753.33 | 718.33 | 792.33 |

Accumulation of PpIX fluorescence produced by each of the prodrugs investigated (AP2-18 (8), ALA, ALA and CP94 (3), MAL, and MAL and CP94 (3)) increased over time in each of the three cell types examined. Novel compound AP2-18 (8), which is a compound according to the first aspect of the invention, was found to significantly increase PpIX accumulation in all three cell types, above and beyond that achieved with ALA or MAL administration either alone or in combination with the iron chelator CP94 (3). These findings suggested that in vitro AP2-18 (8) represents a compound which is able to produce a significantly greater level of PpIX in a potentially significantly shorter time, and hence that AP2-18 (8) has the potential to substantially improve PpIX-induced PDT. Further experimentation to determine whether this significant increase in PpIX accumulation could be translated into increased cell kill on irradiation was undertaken.

2C. PDT Efficacy

Figure 5A:
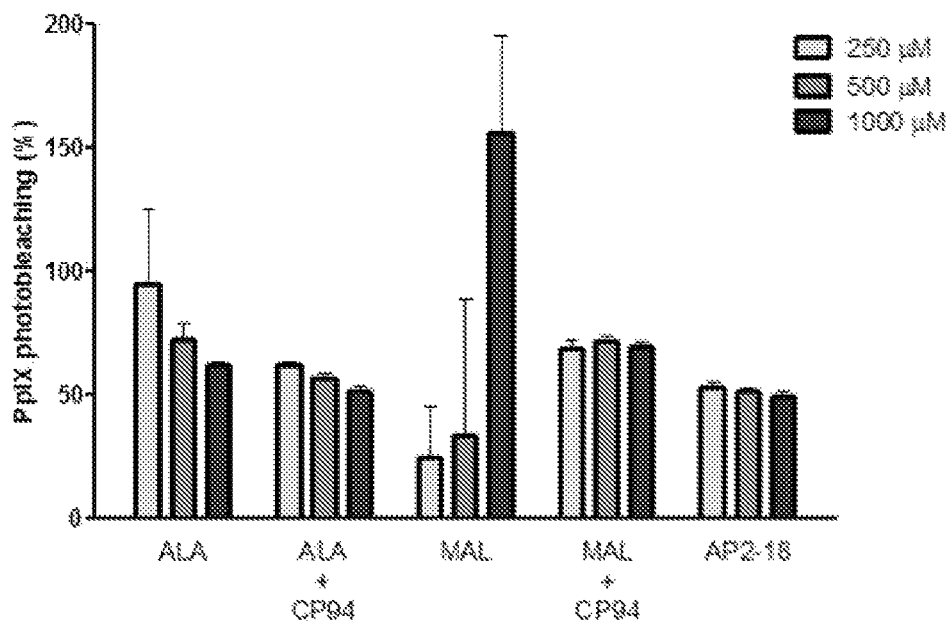
FIG. 5A shows the percentage PpIX photobleaching immediately post irradiation in human dermal fibroblasts (84BR) following exposure to ALA, ALA and CP94 (3), MAL, MAL and CP94 (3), and compound AP2-18 (8).
Figure 5B:
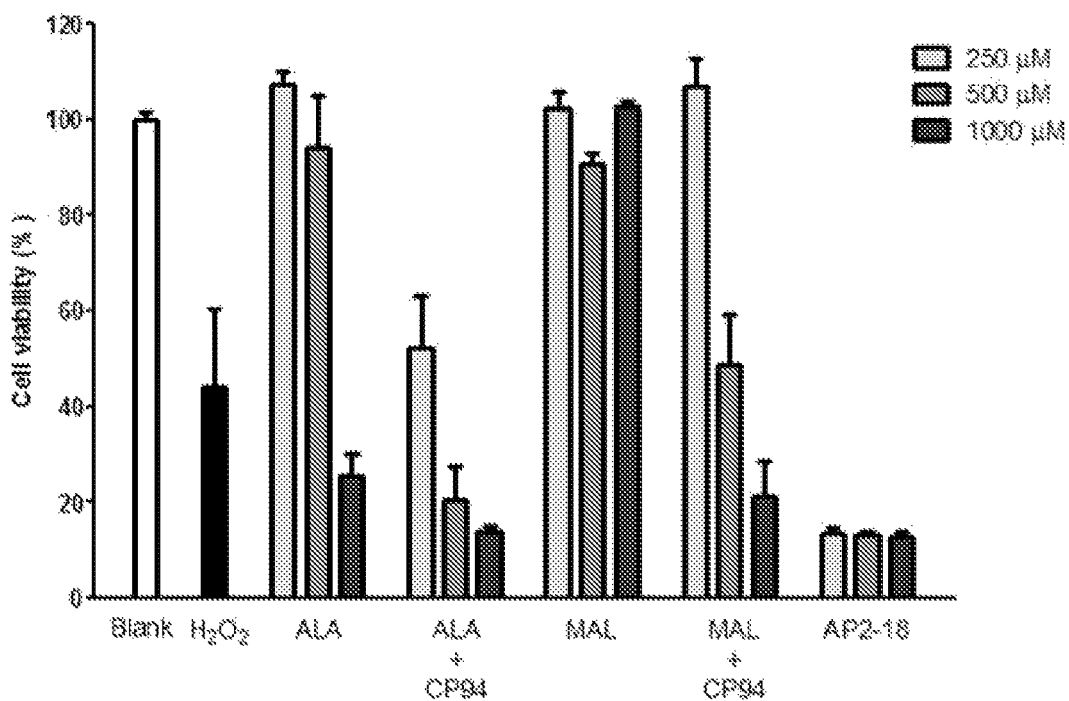
FIG. 5B shows the effect on viability of human dermal fibroblasts (84BR) following exposure to ALA, ALA and CP94 (3), MAL, MAL and CP94 (3), and compound AP2-18 (8), and irradiation with red light.
Figure 6A:
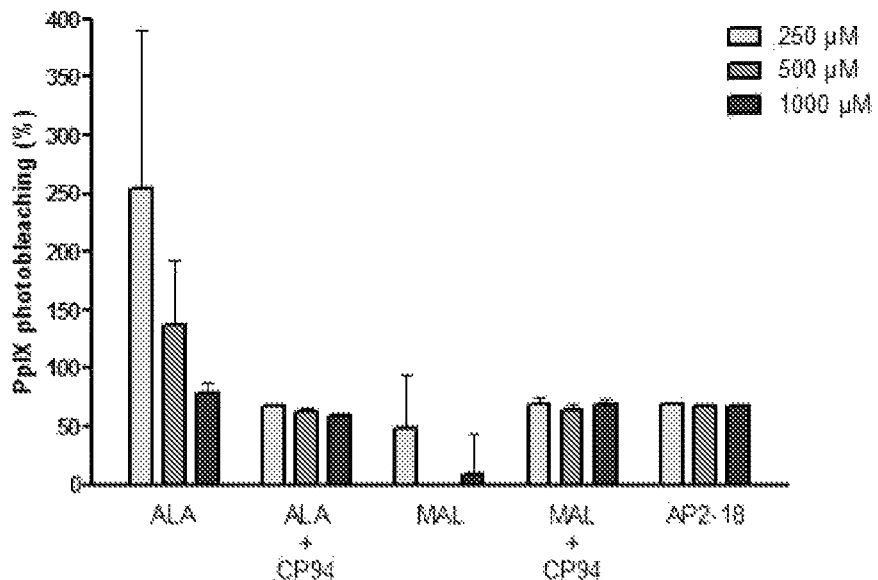
FIG. 6A shows the percentage PpIX photobleaching immediately post irradiation in human epithelial squamous cell carcinoma cells (A431) following exposure to ALA, ALA and CP94 (3), MAL, MAL and CP94 (3), and compound AP2-18 (8).
Figure 6B:
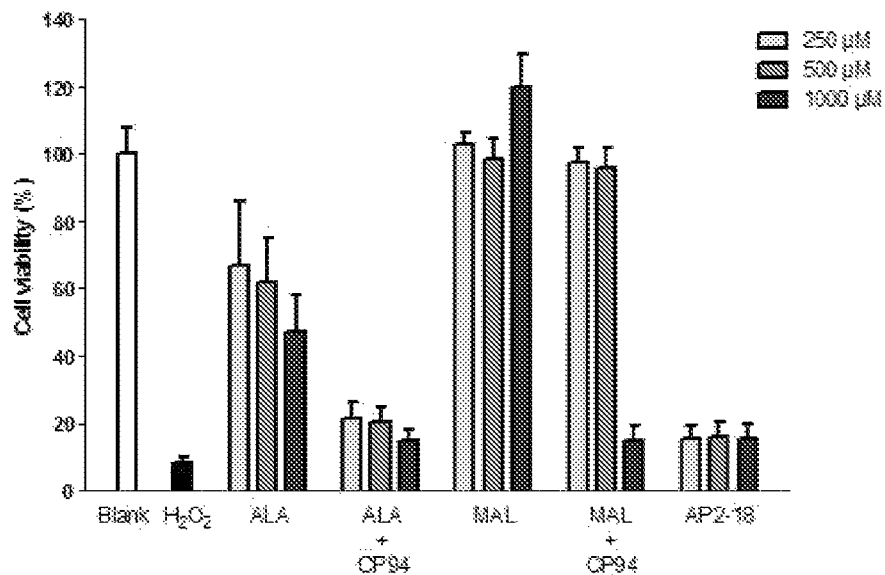
FIG. 6B shows the effect on viability of human epithelial squamous cell carcinoma cells (A431) following exposure to ALA, ALA and CP94 (3), MAL, MAL and CP94 (3), and compound AP2-18 (8), and irradiation with red light.
Figure 7A:
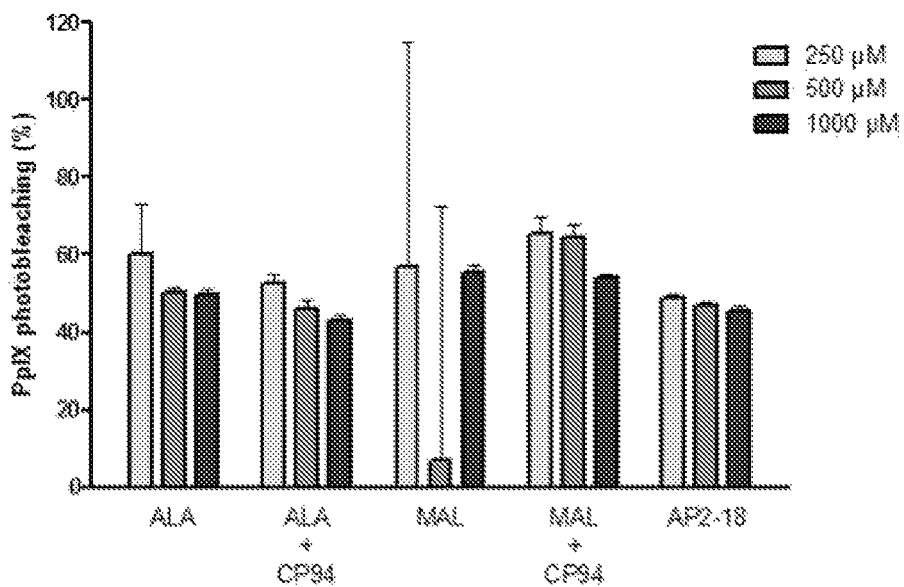
FIG. 7A shows the percentage PpIX photobleaching immediately post irradiation in human glioblastoma cells (U87MG) following exposure to ALA, ALA and CP94 (3), MAL, MAL and CP94 (3), and compound AP2-18 (8).
Figure 7B:
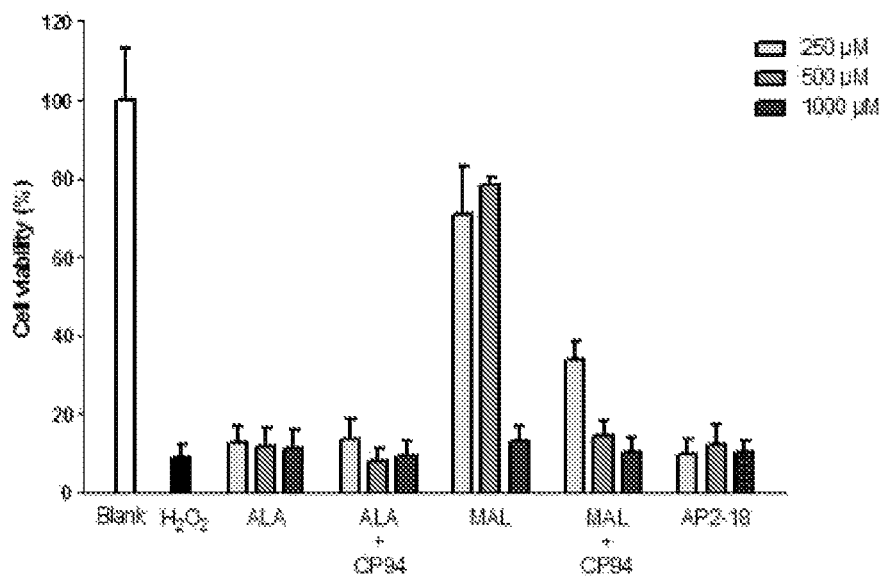
FIG. 7B shows the effect on viability of human glioblastoma cells (U87MG) following exposure to ALA, ALA and CP94 (3), MAL, MAL and CP94 (3), and compound AP2-18 (8), and irradiation with red light.

To assess the effect of AP2-18 (8) on PpIX-induced PDT efficacy, the same three cell types were exposed to equimolar concentrations of ALA, ALA and CP94 (3), MAL, MAL and CP94 (3), and AP2-18 (8) (as described previously) and incubated in the dark for 4 hours. The level of PpIX accumulation was then quantified as before, prior to irradiation with red light (37 J/cm$^2$; 635±2 nm; Aktilite, Galderma, UK). The level of PpIX remaining immediately post irradiation was also ascertained and the change in PpIX level (PpIX photobleaching) was calculated as a percentage (FIGS. 5A, 6A and 7A). Cell viability was then assessed using the NRU assay (as described previously) with these data being normalised against the blank control cells (which were exposed to normal cell media) and presented as a percentage of viable cells (FIGS. 5B, 6B and 7B). The results of the statistical analyses which were subsequently undertaken are presented in FIGS. 5C, 6C and 7C respectively.

The results of the tests with human dermal fibroblasts (84BR) are given in Tables 4 and 5 below and in FIGS. 5A, 5B and 5C. The results of the tests with human epithelial squamous cell carcinoma cells (A431) are given in Tables 6 and 7 below and shown in FIGS. 6A, 6B and 6C. The results of the tests with human glioblastoma cells (U87MG) are given in Tables 8 and 9 below and shown in FIGS. 7A, 7B and 7C.

TABLE 4

PpIX photobleaching in human dermal fibroblasts (84BR) following irradiation - missing data is due to an infection present in these wells in this replicate and therefore data was discarded

| ALA (250 μM) | ALA (500 μM) | ALA (1000 μM) | ALA (250 μM) + CP94 (250 μM) | ALA (500 μM) + CP94 (500 μM) | ALA (1000 μM) + CP94 (1000 μM) | MAL (250 μM) |
|---|---|---|---|---|---|---|
| 57.89474 | 61.57407 | 54.84728 | 57.2327 | 52.15947 | 42.77899 | −13.33333 |
| 66.66666 | 65.75343 | 62.6936 | 62.92974 | 59.41023 | 52.19751 | −66.66666 |
| 65.51724 | 65.90909 | 64.55782 | 66.66666 | 61.27367 | 54.96354 | −83.33334 |
| 200 | 73.91304 | 59.47712 | 61.90476 | 61.25461 | 59.10364 | 70.83334 |
| 200 | 122.5 | 64.88095 | 69.65174 | 60.86956 | 56.86274 | 52.38095 |
| −100 | 69.38776 | 71.28205 | 67.55556 | 66.47565 | 60.36036 | 27.77778 |
| 107.1429 | 60.60606 | 56.08856 | 51.6 | 48.20513 | 41.24294 | 73.68421 |
| 163.6364 | 65.05376 | 61.78571 | 57.08502 | 49.39173 | 47.09302 | 83.87096 |
| 89.18919 | 68.01802 | 61.35135 | 60.42403 | 54.56475 | 50 | 75.75758 |

| MAL (500 μM) | MAL (1000 μM) | MAL (250 μM) + CP94 (250 μM) | MAL (500 μM) + CP94 (500 μM) | MAL (1000 μM) + CP94 (1000 μM) | AP2-18 (250 μM) | AP2-18 (500 μM) | AP2-18 (1000 μM) |
|---|---|---|---|---|---|---|---|
| 45.94595 | 64.23529 | 67.03297 | 72.17281 | 67.97181 | 62.67039 | 58.38767 | 49.67301 |
| 38.80597 | 59.0389 | 62.95547 | 65.1497 | 63.98787 | 57.09666 | 52.30593 | 46.28474 |
| 42.04082 | 54.82063 | 55.53236 | 56.54206 | 55.94615 | 46.36871 | 42.8165 | 39.24669 |
| 56.25 | 46.66667 | 77.90697 | 82.48175 | 79.42583 | 59.53238 | 57.44681 | 61.74636 |
|  | 300 | 61.79775 | 67.15328 | 68.83721 | 54.44265 | 57.77385 | 58.00416 |
| 300 | 116.6667 | 58.42697 | 73.8255 | 64.2534 | 56.63866 | 52.58765 | 54.76674 |
| −75 | 209.6774 | 90.32258 | 83.13953 | 79.18216 | 47.49164 | 48.56828 | 44.37799 |
|  | 167.8571 | 69.23077 | 72.95918 | 71.83099 | 47.4359 | 46.92388 | 45.3348 |
| −171.4286 | 380 | 73.68421 | 68.29269 | 70.70064 | 45.45454 | 44.21699 | 43.99142 |

TABLE 5 human dermal fibroblasts (84BR) cell viability following irradiation

| Untreated | H2O2 (0.01%) | ALA (250 μM) | ALA (500 μM) | ALA (1000 μM) | ALA (250 μM) + CP94 (250 μM) | ALA (500 μM) + CP94 (500 μM) | ALA (1000 μM) + CP94 (1000 μM) |
|---|---|---|---|---|---|---|---|
| 101.2462 | 104.6063 | 102.4162 | 100.2316 | 23.58852 | 102.195 | 72.97579 | 20.42218 |
| 100.1073 | 109.0359 | 100.3211 | 90.5835 | 15.83537 | 84.85323 | 19.46058 | 15.74945 |
| 98.64657 | 112.9591 | 98.90434 | 77.44377 | 15.98893 | 74.06719 | 16.07303 | 15.14433 |
| 104.4733 | 9.466929 | 108.0406 | 84.67118 | 52.72737 | 51.34414 | 14.40936 | 12.83199 |
| 92.99485 | 9.475019 | 110.2246 | 93.22134 | 24.20525 | 25.726 | 9.418395 | 10.93105 |
| 102.5319 | 10.47807 | 115.0942 | 91.31232 | 15.5661 | 15.46903 | 8.253566 | 10.21921 |
| 104.7793 | 13.74779 | 121.2573 | 150.8582 | 48.11189 | 76.61053 | 21.76957 | 16.72478 |
| 91.68063 | 12.79837 | 111.3528 | 127.6699 | 17.93166 | 26.58907 | 12.08228 | 12.12251 |
| 103.5402 | 14.5041 | 100.1126 | 31.14306 | 14.311 | 12.02596 | 11.14869 | 12.19493 |

| MAL (250 μM) | MAL (500 μM) | MAL (1000 μM) | MAL (250 μM) + CP94 (250 μM) | MAL (500 μM) + CP94 (500 μM) | MAL (1000 μM) + CP94 (1000 μM) | AP2-18 (250 μM) | AP2-18 (500 μM) | AP2-18 (1000 μM) |
|---|---|---|---|---|---|---|---|---|
| 89.28648 | 80.92455 | 97.25169 | 105.9153 | 83.20242 | 16.72019 | 15.28693 | 16.63427 | 15.33811 |
| 85.813 | 97.40708 | 109.2407 | 98.83304 | 78.8295 | 19.45144 | 16.318 | 16.76407 | 15.13336 |
| 96.99026 | 87.44188 | 101.8751 | 111.4728 | 102.5935 | 79.80573 | 15.48254 | 15.41673 | 18.64888 |
| 109.2863 | 95.90692 | 97.31442 | 96.00399 | 18.29212 | 12.19295 | 14.29611 | 11.1171 | 10.50233 |
| 100.3397 | 89.15253 | 107.9354 | 88.64292 | 23.6471 | 11.0443 | 9.119099 | 9.555909 | 9.476019 |
| 100.8655 | 85.88836 | 105.4763 | 82.96438 | 46.13477 | 10.39717 | 9.71769 | 8.010893 | 7.824844 |
| 108.4321 | 100.1609 | 98.04485 | 111.7068 | 22.2845 | 13.51446 | 13.07998 | 13.2248 | 12.55699 |
| 121.8447 | 86.03229 | 101.4322 | 132.4733 | 25.06034 | 13.434 | 14.02135 | 13.08802 | 13.20067 |
| 107.4264 | 93.77246 | 103.8781 | 133.9538 | 37.99013 | 14.02135 | 15.34088 | 13.46618 | 12.88687 |

TABLE 6

PpIX photobleaching in human epithelial squamous cell carcinoma cells (A431) following irradiation - missing data is due to an infection present in these wells in this replicate and therefore data was discarded

| ALA (250 μM) | ALA (500 μM) | ALA (1000 μM) | ALA (250 μM) + CP94 (250 μM) | ALA (500 μM) + CP94 (500 μM) | ALA (1000 μM) + CP94 (1000 μM) | MAL (250 μM) |
|---|---|---|---|---|---|---|
| 68.34532 | 71.24183 | 98.34711 | 63.38028 | 60.22727 | 58.84058 | −52.94118 |
| 78.37838 | 77.12418 | 100.7194 | 60 | 63 | 56.33075 | −112.5 |
| 86.92308 | 83.33334 | 100.6897 | 67.20779 | 67.64706 | 58.99705 | 187.5 |

TABLE 6-continued

PpIX photobleaching in human epithelial squamous cell carcinoma cells (A431) following irradiation - missing data is due to an infection present in these wells in this replicate and therefore data was discarded

| | | | | | | | |
|---|---|---|---|---|---|---|---|
| 71.42857 | 88.88889 | 42.3913 | 76.47059 | 66.66666 | 61.34752 | | 81.05264 |
| 387.5 | 101.4493 | 66.34615 | 74.83443 | 72.36842 | 63.57388 | | 100 |
| 77.27273 | 93.58974 | 115.3846 | 70.19231 | 72.36842 | 59.52381 | | 92.77109 |
| 1300 | 583.3333 | 61.68224 | 60.56338 | 55.86855 | 62.06897 | | |
| 123.0769 | 60.31746 | 75 | 71.42857 | 54.07407 | 59.82659 | | |
| 100 | 69.84127 | 51.72414 | 63.80368 | 56.49123 | 53.30296 | | |

| MAL (500 μM) | MAL (1000 μM) | MAL (250 μM) + CP94 (250 μM) | MAL (500 μM) + CP94 (500 μM) | MAL (1000 μM) + CP94 (1000 μM) | AP2-18 (250 μM) | AP2-18 (500 μM) | AP2-18 (1000 μM) |
|---|---|---|---|---|---|---|---|
| −216.6667 | 72.22222 | 48 | 42.96296 | 76.72414 | 71.23746 | 67.94118 | 70.70064 |
| −183.3333 | 52.99145 | 58.06452 | 58.66667 | 70.75813 | 72.34727 | 73.35767 | 69.68839 |
| −33.33333 | 45.51282 | 66.66666 | 65.89147 | 68.92857 | 68.21918 | 68.26347 | 66.26865 |
| −212.5 | 40.25974 | 68.60465 | 67.40741 | 77.61194 | 72.69231 | 74.51737 | 75.68627 |
| −400 | −209.0909 | 85 | 72.32704 | 83.87096 | 72.37354 | 68.67088 | 67.60125 |
| −250 | −110.7143 | 89.53488 | 80.24691 | 53.68421 | 67.63636 | 64.47369 | 72.35773 |
| | 24.63768 | | | 47.24638 | 65.61404 | 62.43386 | 57.71812 |
| | 17.70833 | | | 73.05936 | 60.13746 | 65.86021 | 66.96429 |
| | 144.4444 | | | 74.39613 | 66.31206 | 62.72966 | 57.23684 |

TABLE 7 human epithelial squamous cell carcinoma cells (A431) cell viability following irradiation - missing data is due to an infection present in these wells in this replicate and therefore data was discarded

| Untreated | H2O2 (0.01%) | ALA (250 μM) | ALA (500 μM) | ALA (1000 μM) | ALA (250 μM) + CP94 (250 μM) | ALA (500 μM) + CP94 (500 μM) | ALA (1000 μM) + CP94 (1000 μM) |
|---|---|---|---|---|---|---|---|
| 96.65799 | 4.849673 | 82.00658 | 67.68867 | 59.29512 | 13.57674 | 14.4515 | 7.172601 |
| 103.6911 | 5.759535 | 64.97372 | 28.72551 | 27.29197 | 5.364579 | 5.806345 | 7.371542 |
| 99.65088 | 4.993027 | 20.13594 | 8.056132 | 6.353432 | 5.812196 | 5.215373 | 8.129272 |
| 104.3352 | 5.718442 | 125.0307 | 111.2275 | 109.5082 | 42.7303 | 35.39415 | 8.76577 |
| 92.51461 | 4.676331 | 150.1618 | 105.7573 | 86.84508 | 19.92049 | 11.32778 | 8.318076 |
| 103.1502 | 4.089438 | 127.1037 | 29.3785 | 18.6677 | 7.212009 | 8.348173 | 9.096837 |
| 80.40414 | 12.24248 | 6.313455 | 108.0828 | 42.58255 | 36.20996 | 32.91277 | 26.64367 |
| 65.16018 | 13.02612 | 9.566289 | 59.77822 | 43.46969 | 30.38443 | 36.18039 | 30.56185 |
| 154.4357 | 18.54115 | 15.90932 | 39.69936 | 28.34401 | 32.23263 | 32.12913 | 26.14096 |

| MAL (250 μM) | MAL (500 μM) | MAL (1000 μM) | MAL (250 μM) + CP94 (250 μM) | MAL (500 μM) + CP94 (500 μM) | MAL (1000 μM) + CP94 (1000 μM) | AP2-18 (250 μM) | AP2-18 (500 μM) | AP2-18 (1000 μM) |
|---|---|---|---|---|---|---|---|---|
| 109.5656 | 90.23782 | 91.78101 | 84.56491 | 78.0531 | 5.721502 | 7.087759 | 6.022839 | 6.315399 |
| 90.46208 | 110.2301 | 85.804 | 93.39406 | 86.45865 | 5.949699 | 6.581629 | 6.335878 | 6.00236 |
| 107.8629 | 98.69321 | 110.3323 | 95.46222 | 87.3723 | 5.455272 | 5.92922 | 6.645992 | 5.891187 |
| 109.4385 | 113.2846 | 138.7061 | 93.81889 | 115.7124 | 5.778636 | 7.339921 | 7.159339 | 7.607033 |
| 93.63615 | 104.0869 | 132.5587 | 98.55262 | 103.9825 | 7.023902 | 6.990043 | 7.629605 | 8.758245 |
| 106.3667 | 74.42279 | 155.8802 | 118.7493 | 103.9999 | 8.3256 | 6.619776 | 6.692834 | 7.362494 |
| | | 165.2883 | | | 33.6964 | 32.02563 | 42.87827 | 38.08773 |
| | | 91.72992 | | | 33.74076 | 32.79448 | 32.5727 | 34.19911 |
| | | 106.1163 | | | 27.57516 | 31.10892 | 25.10596 | 25.29818 |

TABLE 8

PpIX photobleaching in human glioblastoma cells (U87MG) following irradiation - missing data is due to an infection present in these wells in this replicate and therefore data was discarded

| ALA (250 μM) | ALA (500 μM) | ALA (1000 μM) | ALA (250 μM) + CP94 (250 μM) | ALA (500 μM) + CP94 (500 μM) | ALA (1000 μM) + CP94 (1000 μM) | MAL (250 μM) |
|---|---|---|---|---|---|---|
| 40.90452 | 41.88931 | 44.39164 | 39.88439 | 32.35639 | 41.33226 | 107.6923 |
| 48.36717 | 44.51561 | 46.24574 | 43.04462 | 38.65863 | 42.78642 | −220 |
| 48.02933 | 46.74267 | 47.24733 | 46.95432 | 38.89717 | 44.4619 | 200 |
| 51.39319 | 48.48485 | 47.14286 | 51.61871 | 48.80546 | 40.42715 | 83.49515 |
| 58.07365 | 51.81024 | 48.47909 | 53.81818 | 50.625 | 38.49028 | 86.40777 |
| 51.31004 | 53.53535 | 49.48742 | 55.44933 | 52.01342 | 37.32336 | 82.47423 |
| 35.71429 | 56.53595 | 52.17391 | 55.60166 | 46.44195 | 49.12043 | |
| 47.82609 | 54.02299 | 55.2 | 65.24064 | 52.26337 | 47.18217 | |

TABLE 8-continued

PpIX photobleaching in human glioblastoma cells (U87MG) following irradiation - missing data is due to an infection present in these wells in this replicate and therefore data was discarded

| 160 | 53.9548 | 55.82609 | 59.84556 | 51.51515 | 45.81993 | | |
|---|---|---|---|---|---|---|---|

| MAL (500 µM) | MAL (1000 µM) | MAL (250 µM) + CP94 (250 µM) | MAL (500 µM) + CP94 (500 µM) | MAL (1000 µM) + CP94 (1000 µM) | AP2-18 (250 µM) | AP2-18 (500 µM) | AP2-18 (1000 µM) |
|---|---|---|---|---|---|---|---|
| −300 | 51.95823 | 52.43903 | 59.74026 | 55.04056 | 46.44444 | 44.79452 | 42.67241 |
| 0 | 47.68133 | 58.22785 | 57.89474 | 52.07226 | 45.11111 | 43.0593 | 41.29032 |
| 0 | 46.84579 | 63.73626 | 55.80111 | 50.3006 | 45.47368 | 41.8983 | 41.50943 |
| 133.3333 | 64.26735 | 72.34042 | 66.5 | 53.6036 | 51.3369 | 47.68392 | 49.03181 |
| 118.5185 | 60.25317 | 80 | 76.37363 | 53.57143 | 49.8954 | 47.31707 | 47.21635 |
| 89.74359 | 57.65306 | 66.98113 | 70.38835 | 48.66071 | 47.11014 | 43.60746 | 42.07534 |
| | 63.88889 | | | 59.95204 | 53.73406 | 53.25814 | 49.05063 |
| | 54.76191 | | | 55.78704 | 52.04991 | 50.39282 | 49.34641 |
| | 49.68554 | | | 57.08061 | 48.93268 | 49.36999 | 47.38676 |

TABLE 9 human glioblastoma cells (U87MG) cell viability following irradiation - missing data is due to an infection present in these wells in this replicate and therefore data was discarded

| Untreated | H2O2 (0.01%) | ALA (250 µM) | ALA (500 µM) | ALA (1000 µM) | ALA (250 µM) + CP94 (250 µM) | ALA (500 µM) + CP94 (500 µM) | ALA (1000 µM) + CP94 (1000 µM) |
|---|---|---|---|---|---|---|---|
| 94.14043 | 2.062079 | 2.360617 | 2.474841 | 3.147201 | 3.38084 | 2.295717 | 1.964729 |
| 106.7374 | 1.960835 | 1.71811 | 2.548826 | 2.012755 | 1.934875 | 2.489119 | 1.784308 |
| 99.12212 | 2.282737 | 2.596852 | 2.951204 | 2.583872 | 2.481331 | 2.557912 | 2.277546 |
| 90.18543 | 1.812221 | 34.20962 | 2.057359 | 2.260388 | 6.414209 | 2.857444 | 1.854331 |
| 102.0784 | 2.215271 | 6.522491 | 1.809213 | 1.848315 | 2.338592 | 1.475343 | 2.165642 |
| 107.7362 | 1.56257 | 4.05757 | 1.765599 | 2.174665 | 2.078414 | 1.721986 | 1.705443 |
| 190.5658 | 23.02261 | 22.80774 | 26.52205 | 25.96951 | 31.15727 | 25.23278 | 23.20679 |
| 60.7797 | 21.33429 | 18.63297 | 36.00737 | 29.56104 | 37.94127 | 20.04502 | 24.98721 |
| 48.65446 | 23.57516 | 21.48777 | 27.22808 | 32.69211 | 32.90699 | 14.21263 | 24.097 |

| MAL (250 µM) | MAL (500 µM) | MAL (1000 µM) | MAL (250 µM) + CP94 (250 µM) | MAL (500 µM) + CP94 (500 µM) | MAL (1000 µM) + CP94 (1000 µM) | AP2-18 (250 µM) | AP2-18 (500 µM) | AP2-18 (1000 µM) |
|---|---|---|---|---|---|---|---|---|
| 101.0185 | 81.62376 | 2.524164 | 29.45828 | 20.62864 | 2.172408 | 3.188737 | 2.369703 | 2.589064 |
| 89.24873 | 83.80233 | 2.394365 | 27.85205 | 18.05314 | 2.509886 | 2.865536 | 3.016104 | 2.554018 |
| 101.7108 | 72.46181 | 3.03168 | 48.08683 | 27.24741 | 2.26197 | 2.446285 | 3.171863 | 2.373597 |
| 38.90113 | 73.95813 | 3.553757 | 29.13108 | 6.831562 | 1.726498 | 1.828764 | 2.064879 | 2.4183 |
| 42.22094 | 78.24413 | 4.85615 | 46.93977 | 8.16876 | 1.989683 | 1.718978 | 2.875491 | 1.795678 |
| 53.14267 | 80.69823 | 16.7356 | 21.84219 | 5.285668 | 2.673966 | 1.660325 | 2.078414 | 12.01029 |
| | | 27.74992 | | | 24.74163 | 31.61772 | 37.17385 | 22.71564 |
| | | 26.52205 | | | 26.82902 | 25.01791 | 36.95897 | 25.87742 |
| | | 29.31546 | | | 25.29418 | 17.71206 | 21.08871 | 17.61997 |

Substantial PpIX photobleaching (i.e. a reduction in PpIX fluorescence during light irradiation) was observed in the vast majority of the treatment groups investigated (see FIGS. 5A, 6A and 7A). This demonstrated that PpIX was being consumed during the light treatment and indicated that PDT was occurring within all three cell types investigated. Complete PpIX photobleaching was rarely achieved with the particular treatment parameters employed here however.

Analysis of the cell viability results (see FIGS. 5B and 5C, 6B and 6C, and 7B and 7C) revealed that both the blank control and hydrogen peroxide positive control groups were successful in all three cell types, producing little cytotoxicity and considerable cell death respectively. In human dermal fibroblasts (84BR; FIGS. 5B and 5C), the use of the iron chelator CP94 (3) improved the PDT effect of both ALA and MAL in a concentration dependent manner, but the novel compound AP2-18 (8) was found to be significantly better (than any of the other treatment parameters investigated) at reducing cell viability following PDT when the lowest concentration employed (250 µM) was considered. At higher doses when significance was not achieved, the level of cell kill produced by AP2-18 (8) was equivalent to (or better than) that observed with the other treatment groups. Very similar trends and significant reductions in cell viability were also observed in the human epithelial squamous carcinoma cells (A431; FIGS. 6B and 6C). It can therefore be concluded in these particular cell types that AP2-18 (8) is an efficacious prodrug for PpIX-induced PDT which achieved this effect at lower concentrations than possible with ALA or MAL with or without administration of the iron chelator CP94 (3). Less significant improvements in cell kill over and above the other prodrugs administered with and without the iron chelator CP94 (3) were observed with AP2-18 (8) in the human glioblastoma cells (U87MG; FIGS. 7B and 7C) however, as these cells appear to be more susceptible to the cytotoxic effects of PpIX-PDT at lower doses. Despite this, AP2-18 (8) still produced highly effective PpIX-induced PDT cell kill in this cell type as well.

The significant increases in cytotoxicity observed for PpIX-induced PDT conducted with compound AP2-18 (8) could potentially be translated into clinical PDT settings to produce substantial benefits for patients undergoing dermatological PDT and other PDT applications.

Figure 8A:
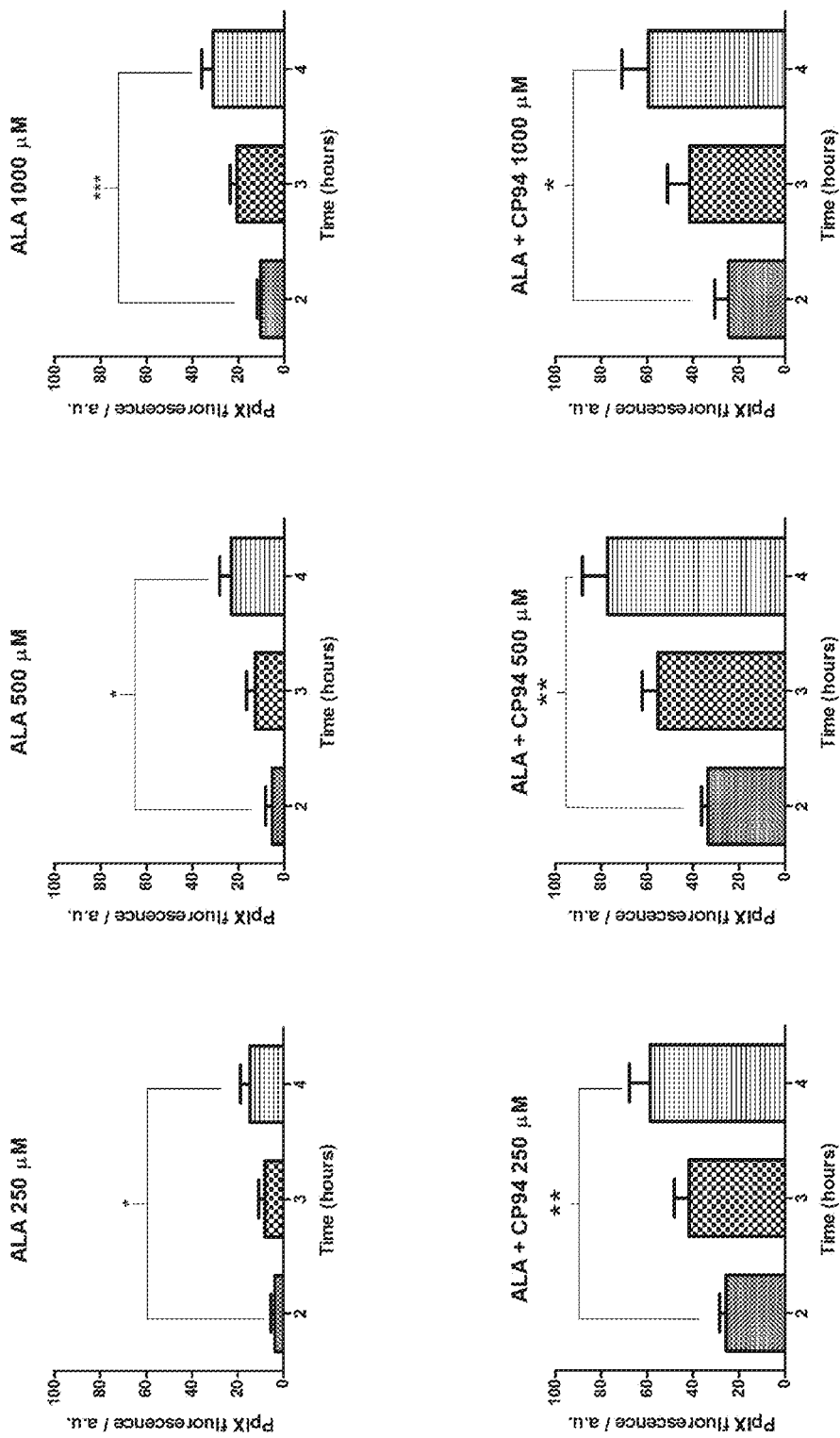
FIG. 8 shows the mean PpIX fluorescence measured in A431 cells following increasing doses (250, 500 or 1000 μM) of (A) ALA+/− CP94, (B) MAL+/− CP94 and (C) AP2-18 after varying incubation periods (2, 3 or 4 hours); *,  and * indicates statistical significance at the 0.050, 0.010 and 0.001 levels respectively.
Figure 8B:
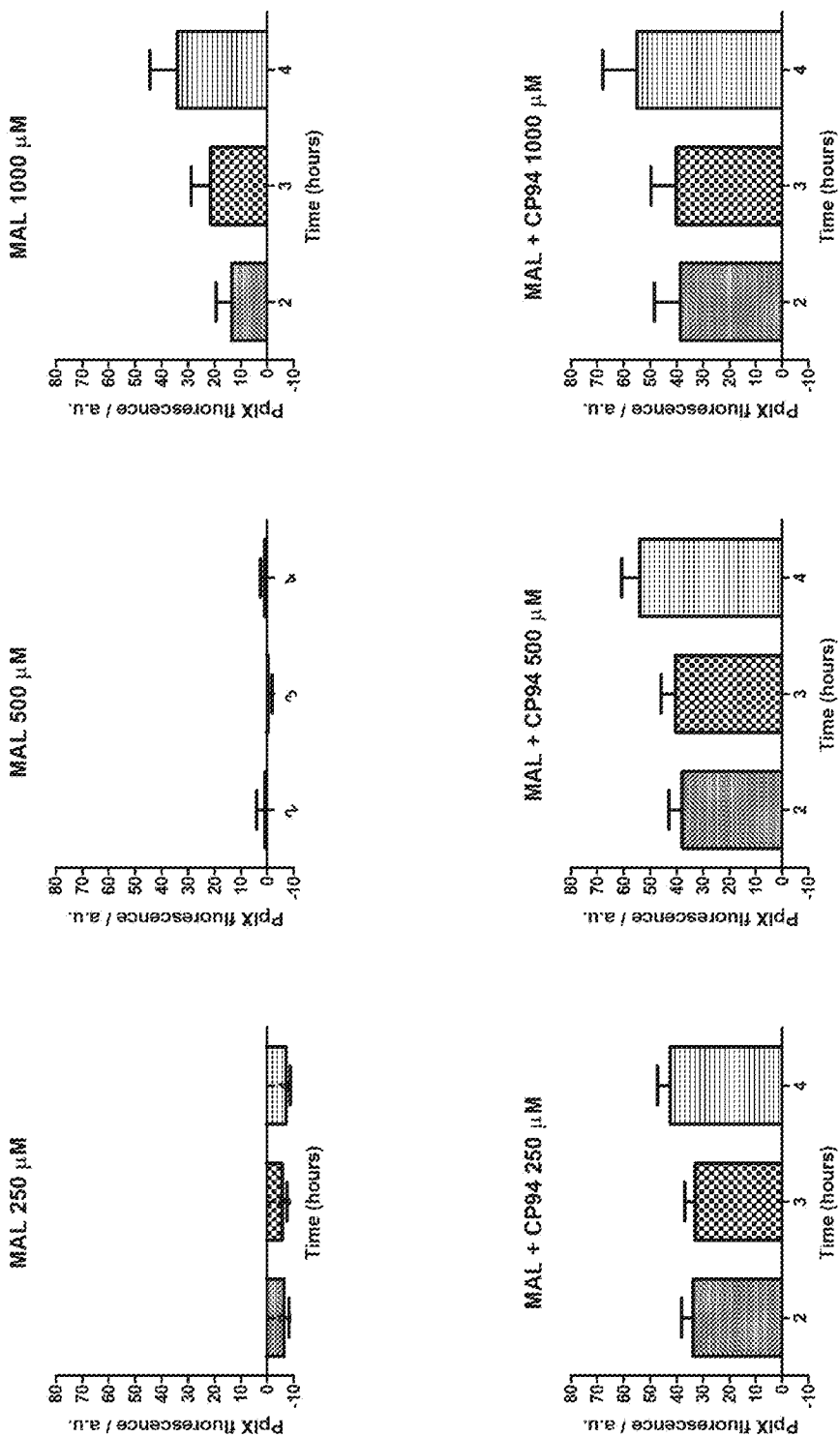
Figure 8C:
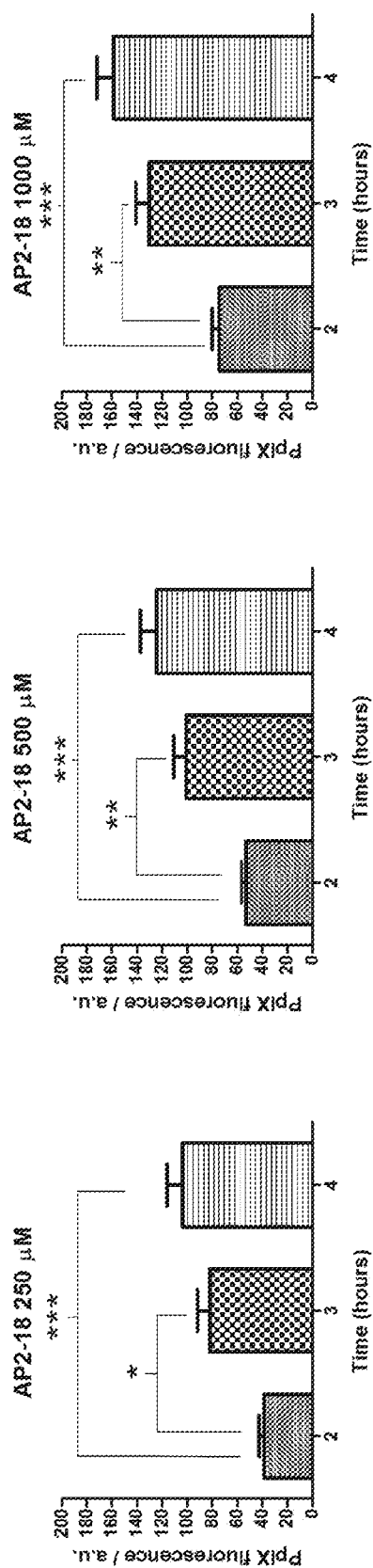
Figure 9A:
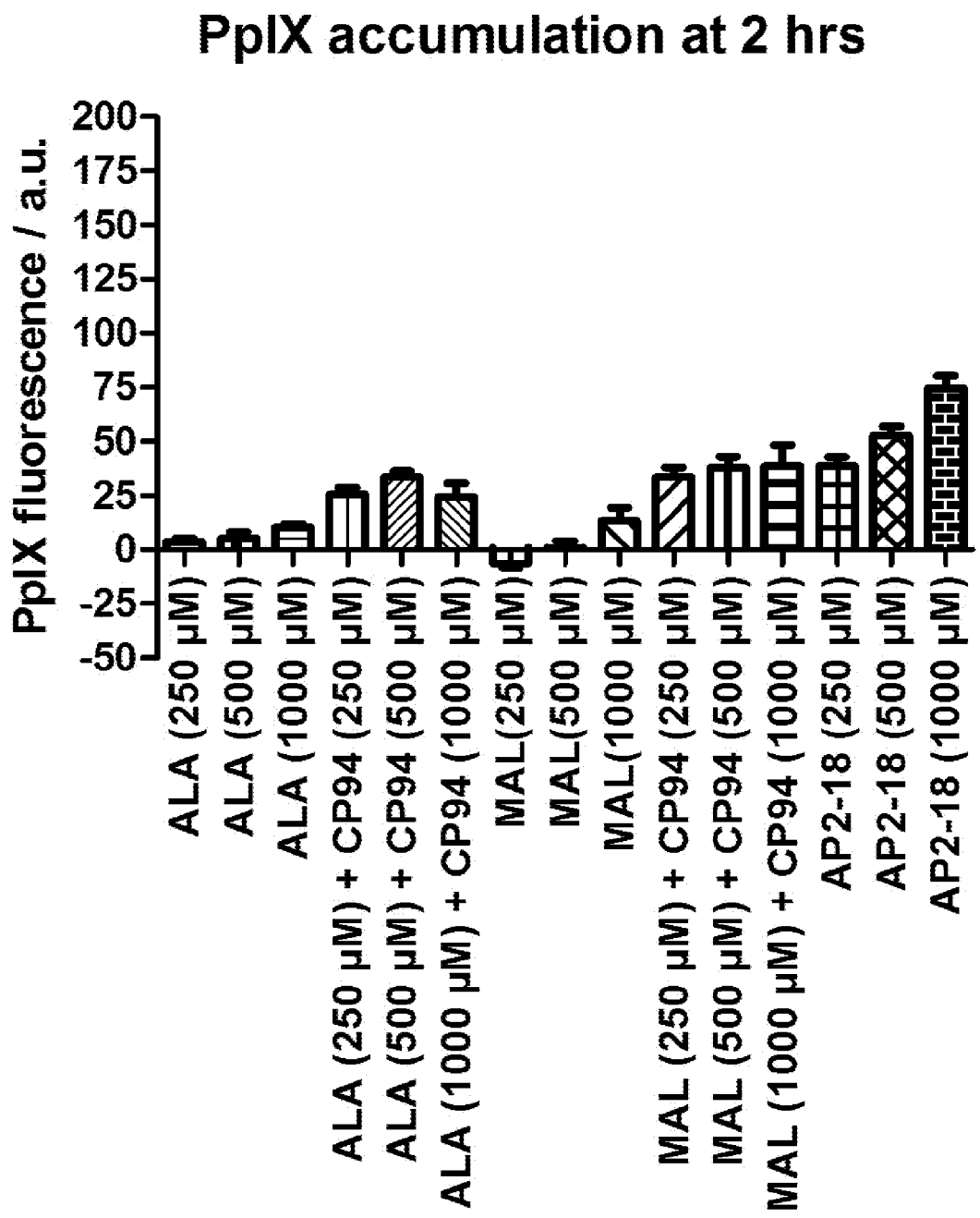
Figure 9B:
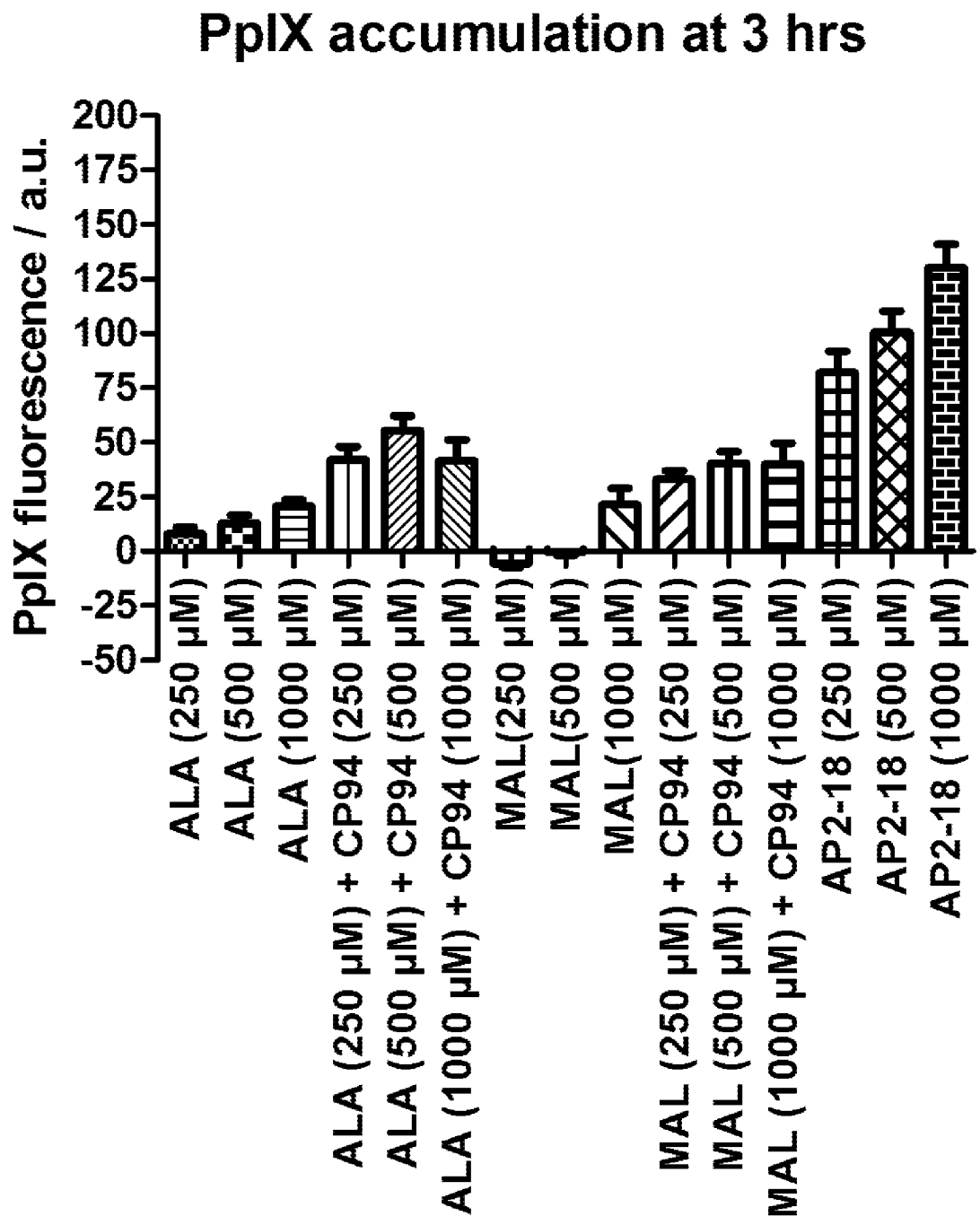
Figure 9C:
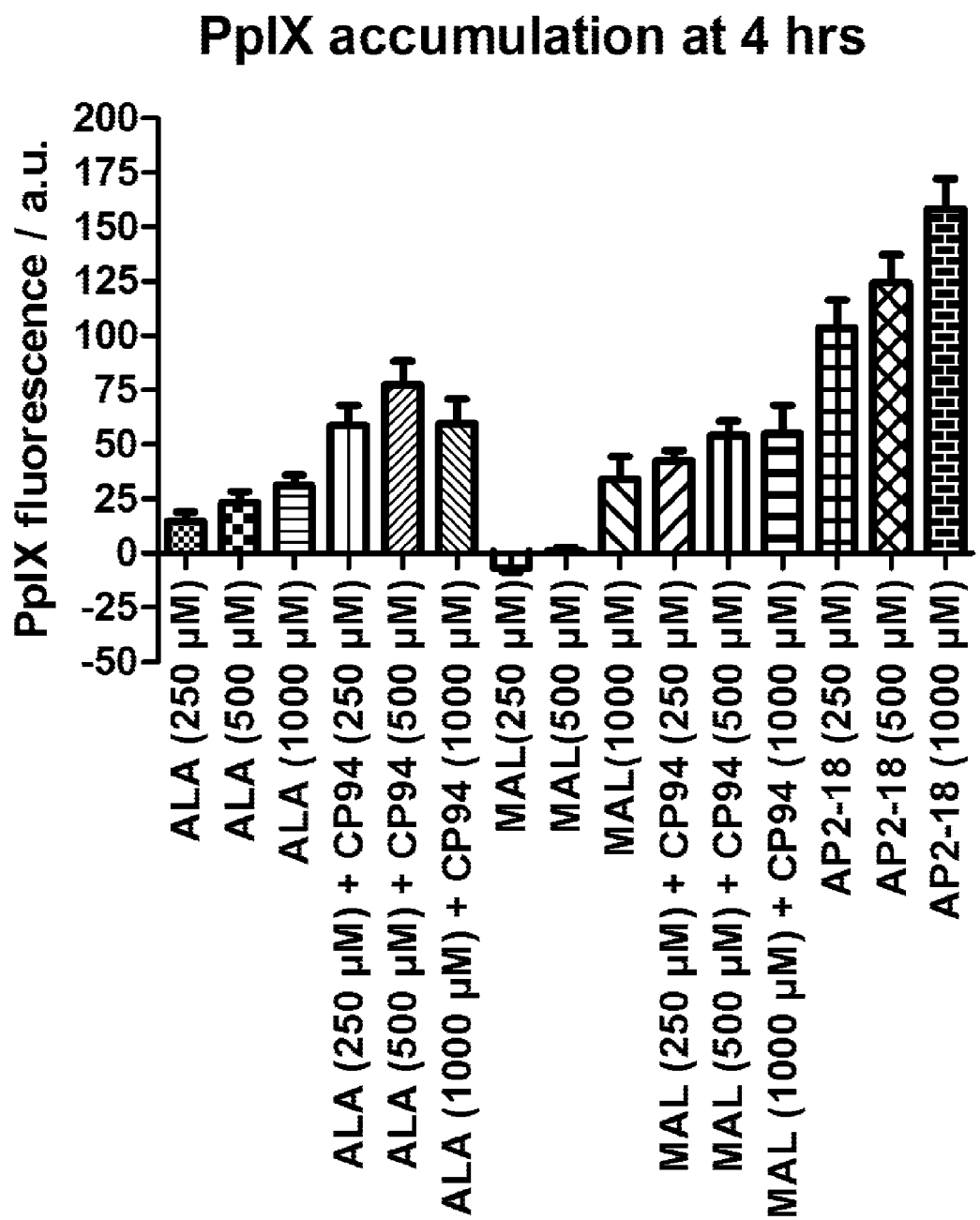

2D. PDT Efficacy in Human Epithelial Squamous Carcinoma Cells (A431) with Variable Incubation Periods Human epithelial squamous carcinoma cells (A431) were exposed to equimolar concentrations of ALA, ALA and CP94 (3), MAL, MAL and CP94 (3), and AP2-18 (8) (as described previously) and incubated in the dark for incubation periods of 2, 3 or 4 hours. The level of PpIX accumulation was then measured; the results are given in Table 10 below and are shown in FIG. 8A (ALA, ALA and CP94 (3)), FIG. 8B (MAL, MAL and CP94 (3)) and FIG. 8C (CP94 (3)). FIG. 9 compares the level of PpIX accumulation measured in human epithelial squamous cell carcinoma cells (A431) following exposure to ALA, ALA and CP94 (3), MAL, MAL and CP94 (3), and AP2-18 (8), after the cells had been incubated with the compound(s) for 2 hours (FIG. 9A(i)), 3 hours (FIG. 9B(i)) and 4 hours (FIG. 9C(i)). The results of corresponding statistical analyses for each incubation period are presented in FIG. 9A(ii) (2 hours), FIG. 9B(ii) (3 hours), and FIG. 9C(ii) (4 hours).

Figure 11A:
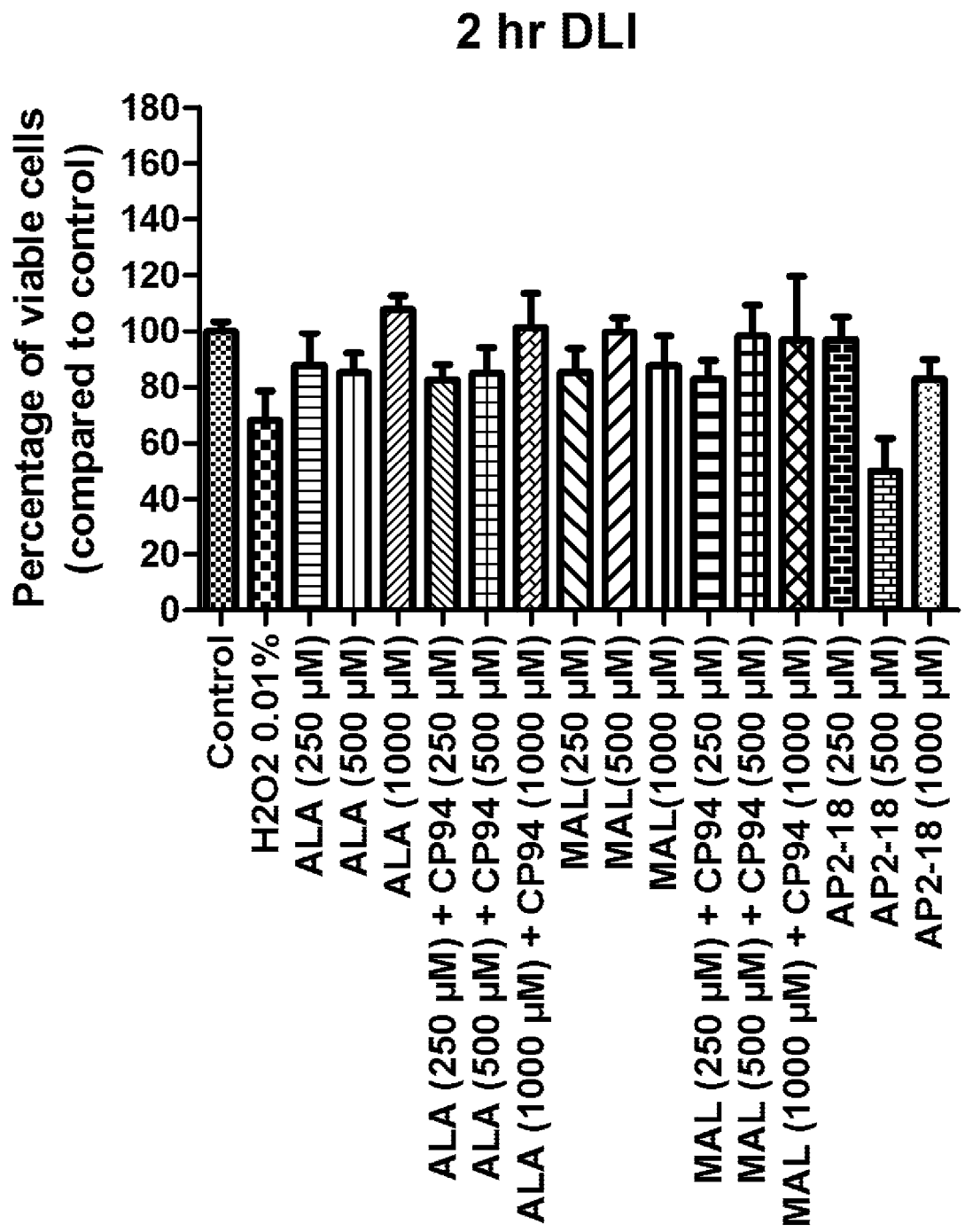
Figure 11B:
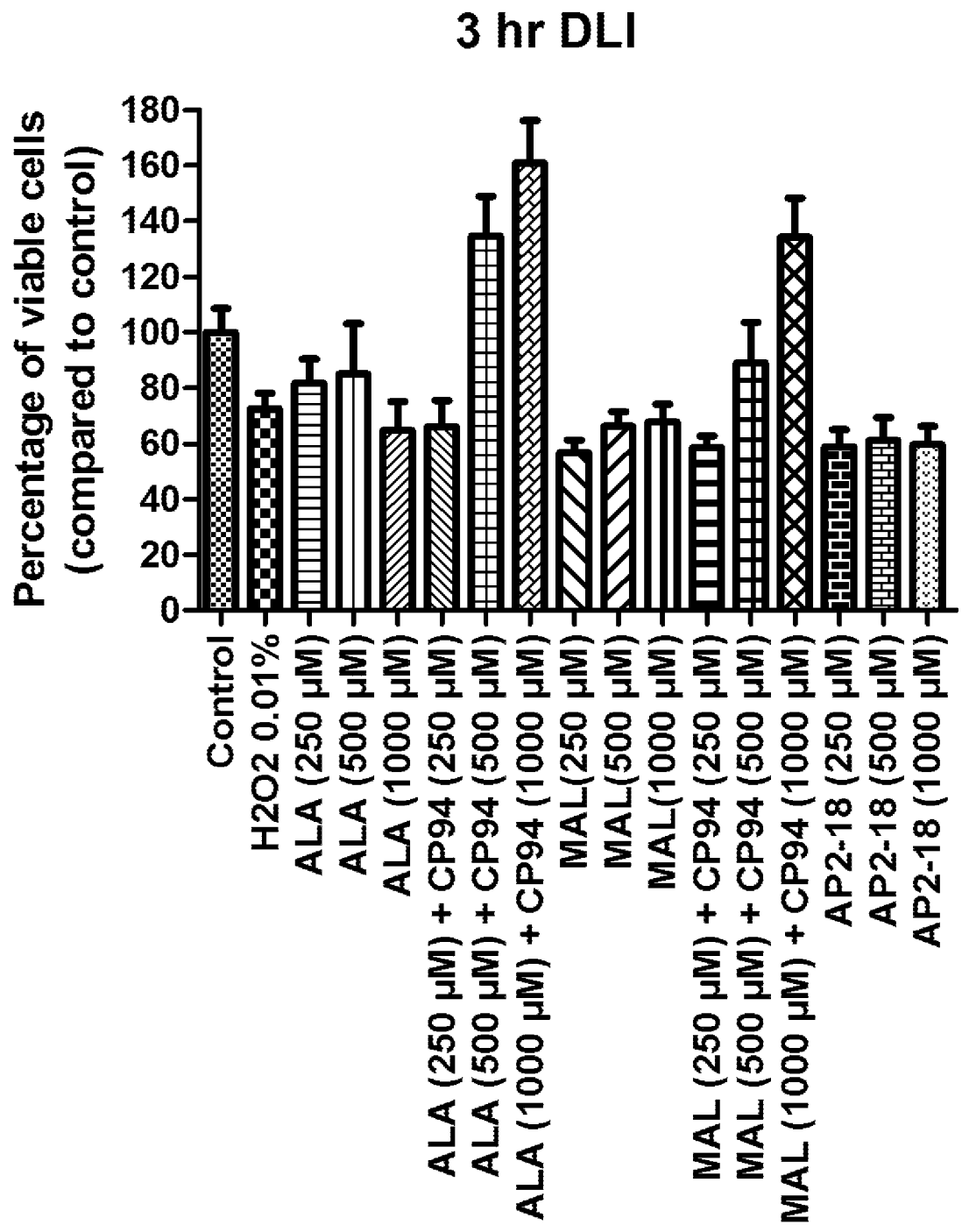
Figure 11C:
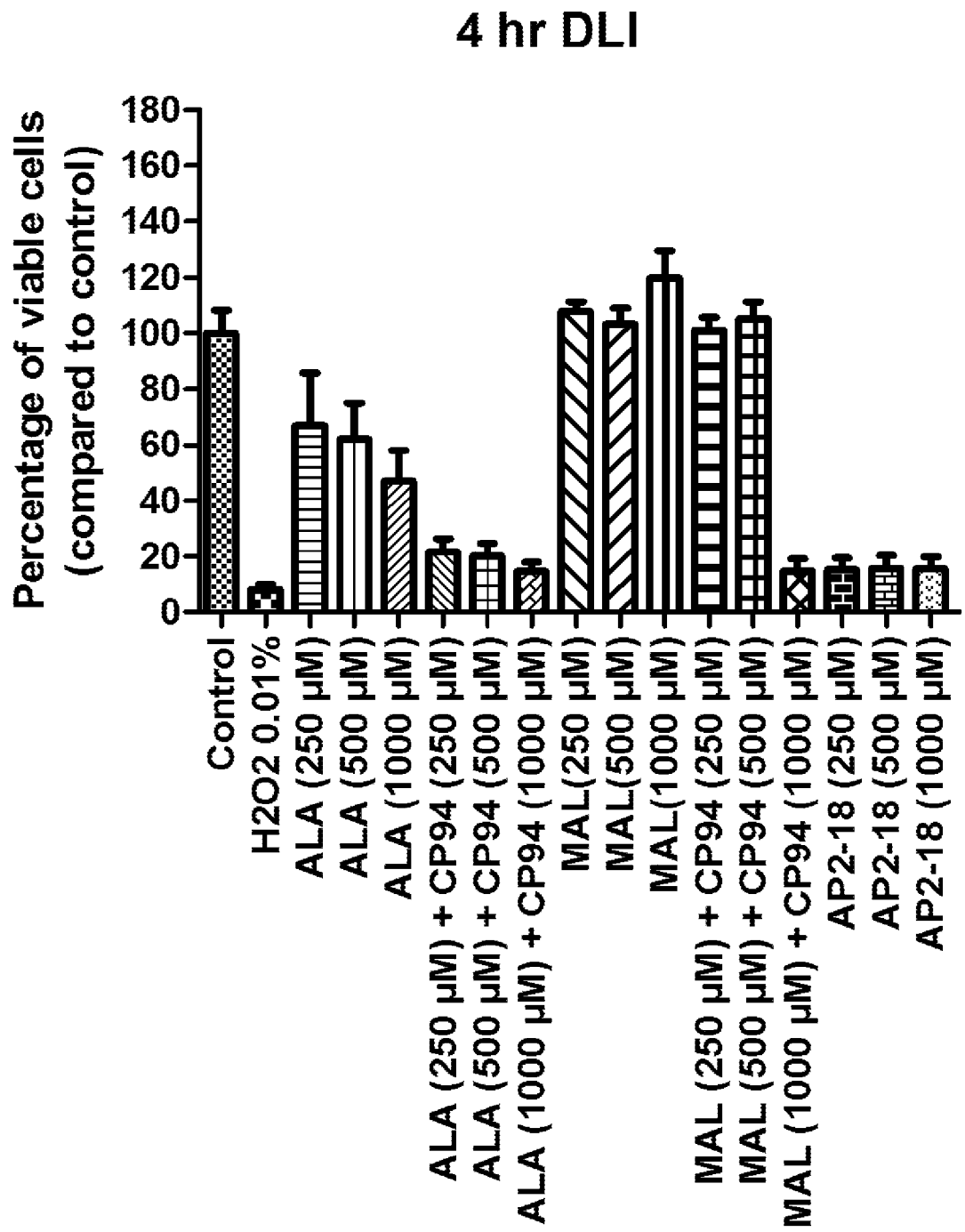

After the relevant incubation period, the cells were irradiated with red light (37 J/cm$^2$; 635±2 nm; Aktilite, Galderma, UK). Cell viability was then assessed using the NRU assay (as described previously); the results of the cell viability tests are given in Table 11 below. These data were normalised against the blank control cells (which were exposed to normal cell media) and presented as a percentage of viable cells in FIGS. 10A (ALA, ALA and CP94 (3)), 10B (MAL, MAL and CP94 (3)), and 10C (AP2-18 (8)). FIG. 11 compares the percentage of viable cells following exposure to ALA, ALA and CP94 (3), MAL, MAL and CP94 (3), and AP2-18 (8), after the cells had been incubated with the compound(s) for 2 hours (FIG. 11A(i)), 3 hours (FIG. 11B(i)) and 4 hours (FIG. 11C(i)). The results of corresponding statistical analyses for each incubation period are presented in FIG. 11A(ii) (2 hours), FIG. 11B(ii) (3 hours), and FIG. 11C(ii) (4 hours).

TABLE 10

PpIX fluorescence measured in human epithelial squamous cell carcinoma cells (A431) after varying incubation periods

| ALA (250 µM) | | | ALA (500 µM) | | | ALA (1000 µM) | | |
|---|---|---|---|---|---|---|---|---|
| 2 hours | 3 hours | 4 hours | 2 hours | 3 hours | 4 hours | 2 hours | 3 hours | 4 hours |
| −1.33 | 3 | 13.33 | −3.67 | 7 | 22.67 | 1.33 | 14.33 | 32.33 |
| 1.67 | 8 | 17.33 | −1.67 | 9 | 25.67 | 9.33 | 25.33 | 45.33 |
| 3.67 | 8 | 17.33 | −2.67 | 6 | 27.67 | 14.33 | 26.33 | 43.33 |
| 10 | 18 | 28 | 15.33 | 27 | 38 | 12.33 | 27.33 | 38.33 |
| 9 | 19 | 28 | 12.33 | 24 | 36 | 15.33 | 28.33 | 38.33 |
| 11 | 18 | 28 | 19.33 | 32 | 43 | 16.33 | 32.33 | 45.33 |
| −1 | −0.66667 | −0.33333 | 3.666667 | 2.666667 | 5 | 8.333333 | 12.33333 | 12.33333 |
| −1 | 0.333333 | −0.33333 | 0.666667 | 2.666667 | 4 | 6.333333 | 10.33333 | 12.33333 |
| 1.333333 | −0.66667 | 1.333333 | 5 | 4.666667 | 6.666667 | 9.666667 | 9.333333 | 12 |

| ALA (250 µM) + CP94 (250 µM) | | | ALA (500 µM) + CP94 (500 µM) | | | ALA (1000 µM) + CP94 (1000 µM) | | |
|---|---|---|---|---|---|---|---|---|
| 2 hours | 3 hours | 4 hours | 2 hours | 3 hours | 4 hours | 2 hours | 3 hours | 4 hours |
| 26.67 | 46 | 70.67 | 38.67 | 69.33 | 108 | 4 | 15.67 | 35 |
| 24.67 | 46 | 71.67 | 33.67 | 61.33 | 95 | 4 | 17.67 | 34 |
| 19.67 | 38 | 61.67 | 37.67 | 69.33 | 102 | 5 | 15.67 | 38 |
| 37 | 62 | 87.33 | 38 | 68 | 95 | 45 | 76.67 | 103.67 |
| 34 | 58 | 77.33 | 44 | 73 | 100 | 46 | 77.67 | 100.67 |
| 39 | 67 | 89.33 | 40 | 71 | 94 | 50 | 81.67 | 110.67 |
| 18 | 23.33333 | 25 | 28.33333 | 33.66667 | 39 | 22 | 27 | 37 |
| 16 | 19.33333 | 25 | 23.33333 | 30.66667 | 37 | 22 | 33 | 42 |
| 15.33333 | 17.33333 | 20.66667 | 18.66667 | 21.66667 | 25.66667 | 22.33333 | 29 | 34.66667 |

| MAL (250 µM) | | | MAL (500 µM) | | | MAL (1000 µM) | | |
|---|---|---|---|---|---|---|---|---|
| 2 hours | 3 hours | 4 hours | 2 hours | 3 hours | 4 hours | 2 hours | 3 hours | 4 hours |
| −5 | −4.67 | −4.67 | −7.33 | −3.67 | −4.33 | 28 | 45 | 70 |
| 1 | −0.67 | −2.67 | 4.67 | −6.67 | −7.33 | 21 | 50 | 74 |
| −0.33 | 1.33 | −2.67 | −5.67 | 5.33 | 3.67 | 9.67 | 42 | 64 |
| −5.33 | 0.67 | −2.67 | −5.67 | −2.67 | 0.67 | 10.67 | 22.67 | 34.33 |
| −6.33 | −3.33 | −3.67 | −7.67 | 0.33 | 3.67 | 11.67 | 25.67 | 39.33 |
| −11 | −7.33 | −8.67 | 8.67 | −2.67 | 1.67 | −3.66667 | 20.67 | 30.33 |
| −10 | −11.67 | −11.67 | −2.33 | 7.67 | 9 | 0.333333 | −3.33333 | −2 |
| −16 | −9.67 | −10.67 | 1.67 | −2.33 | 0 | −8.33333 | 0.666667 | 4 |
| −4.33 | −14.67 | −15.67 | 21 | 1.67 | 2 | 51 | −10.3333 | −8.33333 |

TABLE 10-continued

PpIX fluorescence measured in human epithelial squamous cell carcinoma cells (A431) after varying incubation periods Drug

| MAL (250 μM) + CP94 (250 μM) | | | MAL (500 μM) + CP94 (500 μM) | | | MAL (1000 μM) + CP94 (1000 μM) | | |
|---|---|---|---|---|---|---|---|---|
| Incubation time: | | | | | | | | |
| 2 hours | 3 hours | 4 hours | 2 hours | 3 hours | 4 hours | 2 hours | 3 hours | 4 hours |
| 42 | 51 | 65.67 | 54 | 57 | 73.67 | 40.33 | 34.33 | 51.33 |
| 50 | 42 | 53.67 | 61 | 54 | 72.67 | 40.33 | 40.33 | 61.33 |
| 28 | 50 | 61.67 | 54.33 | 61 | 79.67 | 82.67 | 40.33 | 60.33 |
| 24 | 28 | 35.67 | 40.33 | 54.33 | 68.33 | 74.67 | 82.67 | 110.67 |
| 31 | 24 | 34.67 | 19.33 | 40.33 | 55.33 | 63.67 | 74.67 | 96.67 |
| 21.33 | 31 | 39.67 | 26 | 19.33 | 27.33 | 9.666667 | 63.67 | 86.67 |
| 30.33 | 21.33 | 27.33 | 27 | 26 | 39.33 | 11.66667 | 9.666667 | 11.33333 |
| 19.33 | 30.33 | 37.33 | 24 | 27 | 36.33 | 3.666667 | 11.66667 | 10.33333 |
| 57 | 19.33 | 26.33 | 34.33 | 24 | 33.33 | 20.33 | 3.666667 | 5 |

| AP2-18 (250 μM) | | | AP2-18 (500 μM) | | | AP2-18 (1000 μM) | | |
|---|---|---|---|---|---|---|---|---|
| Incubation time: | | | | | | | | |
| 2 hours | 3 hours | 4 hours | 2 hours | 3 hours | 4 hours | 2 hours | 3 hours | 4 hours |
| 17.33 | 42.33 | 53.67 | 35.33 | 59.33 | 71.67 | 58.33 | 96.33 | 113.67 |
| 19.33 | 42.33 | 52.67 | 33.33 | 67.33 | 82.67 | 69.33 | 100.33 | 119.67 |
| 43.67 | 46.33 | 57.67 | 57.67 | 62.33 | 73.67 | 58.67 | 116.33 | 140.67 |
| 42.67 | 100.33 | 127.67 | 49.67 | 114.33 | 137.67 | 58.67 | 117.33 | 145.67 |
| 41.67 | 96.33 | 120.67 | 55.67 | 109.33 | 136.67 | 63.67 | 114.33 | 139.67 |
| 44.67 | 97.33 | 120.67 | 58.67 | 114.33 | 140.67 | 78.67 | 118.33 | 141.67 |
| 54.67 | 89.67 | 113.67 | 69.67 | 119.67 | 151.67 | 97.67 | 144.67 | 177.67 |
| 48.67 | 111.67 | 144.67 | 58.67 | 139.67 | 177.67 | 93.67 | 180.67 | 221.67 |
| 34.33 | 111.67 | 141.67 | 58.33 | 118.67 | 146.67 | 93.67 | 182.67 | 225.67 |

TABLE 11 cell viability of human epithelial squamous cell carcinoma cells (A431) after varying incubation periods - an extra viability experiment (of three more replicates) was conducted for the 3 hour time point resulting in more data at this time point than at 2 hours or 4 hours.

Drug

| ALA (250 μM) | | | ALA (500 μM) | | | ALA (1000 μM) | | |
|---|---|---|---|---|---|---|---|---|
| Incubation time: | | | | | | | | |
| 2 hours | 3 hours | 4 hours | 2 hours | 3 hours | 4 hours | 2 hours | 3 hours | 4 hours |
| 104.2825 | 124.0654 | 82.00658 | 99.83801 | 118.05 | 67.68867 | 87.30403 | 146.327 | 59.29512 |
| 103.9063 | 135.6267 | 64.97372 | 113.3557 | 77.38437 | 28.72551 | 106.5283 | 79.28516 | 27.29197 |
| 123.5695 | 95.30766 | 20.13594 | 112.7404 | 69.99367 | 8.056132 | 118.4391 | 120.4428 | 6.353432 |
| 112.4377 | 55.77225 | 125.0307 | 95.2285 | 77.17889 | 111.2275 | 110.6882 | 43.81615 | 109.5082 |
| 117.6227 | 55.32471 | 150.1618 | 69.93956 | 78.53456 | 105.7573 | 113.0739 | 38.84751 | 86.84508 |
| 97.70968 | 62.01816 | 127.1037 | 82.25002 | 70.10976 | 29.3785 | 122.8714 | 34.80008 | 18.6677 |
| 44.14486 | 56.04799 | 6.313455 | 65.55643 | 42.15261 | 108.0828 | 119.6405 | 39.78674 | 42.58255 |
| 34.7079 | 85.67144 | 9.566289 | 62.54295 | 44.3852 | 59.77822 | 111.0759 | 27.42419 | 43.46969 |
| 50.72694 | 55.08164 | 15.90932 | 64.52551 | 60.84639 | 39.69936 | 80.14803 | 54.74842 | 28.34401 |
| | 120.1384 | | | 274.4678 | | | 57.2548 | |
| | 57.17644 | | | 51.10357 | | | 73.63197 | |
| | 77.31487 | | | 55.09991 | | | 60.03657 | |

| ALA (250 μM) + CP94 (250 μM) | | | ALA (500 μM) + CP94 (500 μM) | | | ALA (1000 μM) + CP94 (1000 μM) | | |
|---|---|---|---|---|---|---|---|---|
| Incubation time: | | | | | | | | |
| 2 hours | 3 hours | 4 hours | 2 hours | 3 hours | 4 hours | 2 hours | 3 hours | 4 hours |
| 80.84892 | 118.2625 | 13.57674 | 62.6829 | 179.602 | 14.4515 | 88.87176 | 187.2722 | 7.172601 |
| 94.75857 | 105.4936 | 5.364579 | 58.74007 | 194.7971 | 5.806345 | 83.52973 | 187.8648 | 7.371542 |
| 89.78888 | 107.0143 | 5.812196 | 74.94252 | 178.8193 | 5.215373 | 54.14272 | 188.6922 | 8.129272 |
| 65.13625 | 79.84451 | 42.7303 | 80.40504 | 156.1218 | 35.39415 | 133.3051 | 159.1827 | 8.76577 |
| 64.84996 | 81.08912 | 19.92049 | 101.4314 | 169.8354 | 11.32778 | 164.7651 | 150.049 | 8.318076 |
| 96.65995 | 72.26578 | 7.212009 | 91.4113 | 152.0678 | 8.348173 | 135.2773 | 146.1486 | 9.096837 |
| 86.5715 | 39.38687 | 36.20996 | 114.9617 | 60.24659 | 32.91277 | 68.80782 | 78.64045 | 26.64367 |
| 105.5247 | 20.22659 | 30.38443 | 130.7428 | 63.47884 | 36.18039 | 78.08617 | 109.7634 | 30.56185 |

TABLE 11-continued cell viability of human epithelial squamous cell carcinoma cells (A431) after varying
incubation periods - an extra viability experiment (of three more replicates) was conducted
for the 3 hour time point resulting in more data at this time point than at 2 hours or 4 hours.

Drug

| 58.41924 | 30.35655 | 32.23263 | 49.85461 | 55.64812 | 32.12913 | 105.3661 | 78.87371 | 26.14096 |
|---|---|---|---|---|---|---|---|---|
|  | 52.82748 |  |  | 130.1685 |  |  | 257.5813 |  |
|  | 37.6257 |  |  | 120.4127 |  |  | 178.438 |  |
|  | 49.26211 |  |  | 154.1857 |  |  | 208.3714 |  |

| MAL (250 µM) | | | MAL (500 µM) | | | MAL (1000 µM) | | |
|---|---|---|---|---|---|---|---|---|
| | | | | Incubation time: | | | | |
| 2 hours | 3 hours | 4 hours | 2 hours | 3 hours | 4 hours | 2 hours | 3 hours | 4 hours |
| 78.62667 | 92.90373 | 109.5656 | 103.8357 | 40.77746 | 90.23782 | 113.344 | 93.27271 | 91.78101 |
| 100.9237 | 73.67224 | 90.46208 | 110.62 | 47.70974 | 110.2301 | 113.9162 | 84.83098 | 85.804 |
| 89.57724 | 65.45414 | 107.8629 | 117.5455 | 49.73352 | 98.69321 | 113.1911 | 88.71082 | 110.3323 |
| 117.6227 | 62.6519 | 109.4385 | 82.91804 | 71.70718 | 113.2846 | 108.366 | 39.35058 | 138.7061 |
| 107.2209 | 51.74115 | 93.63615 | 108.8432 | 76.88815 | 104.0869 | 113.6783 | 38.50124 | 132.5587 |
| 106.7755 | 54.37083 | 106.3667 | 82.88622 | 81.86658 | 74.42279 | 85.84456 | 43.00928 | 155.8802 |
| 45.7309 | 33.35555 | 111.1665 | 99.49775 | 74.40853 | 104.4856 | 45.88951 | 59.91336 | 165.2883 |
| 63.25668 | 40.45318 | 115.1445 | 114.8824 | 55.24825 | 97.35677 | 39.14882 | 53.88204 | 91.72992 |
| 57.86413 | 63.31223 | 124.4547 | 75.70711 | 104.0986 | 135.6405 | 53.81972 | 52.9157 | 106.1163 |
|  | 38.2134 |  |  | 49.37965 |  |  | 75.55178 |  |
|  | 54.70811 |  |  | 75.04244 |  |  | 92.94763 |  |
|  | 47.85164 |  |  | 67.40237 |  |  | 90.51848 |  |

| MAL (250 µM) + CP94 (250 µM) | | | MAL (500 µM) + CP94 (500 µM) | | | MAL (1000 µM) + CP94 (1000 µM) | | |
|---|---|---|---|---|---|---|---|---|
| | | | | Incubation time: | | | | |
| 2 hours | 3 hours | 4 hours | 2 hours | 3 hours | 4 hours | 2 hours | 3 hours | 4 hours |
| 86.58288 | 80.44799 | 84.56491 | 83.34945 | 156.0993 | 78.0531 | 83.34945 | 167.2245 | 5.721502 |
| 72.87312 | 79.66531 | 93.39406 | 49.87458 | 170.7465 | 86.45865 | 49.87458 | 183.0345 | 5.949699 |
| 99.5323 | 74.53319 | 95.46222 | 52.11251 | 178.2043 | 87.3723 | 52.11251 | 162.685 | 5.455272 |
| 116.0004 | 40.28812 | 93.81889 | 92.87457 | 47.54998 | 115.7124 | 92.87457 | 69.35842 | 5.778636 |
| 67.87191 | 40.98719 | 98.55262 | 142.53 | 52.36509 | 103.9825 | 142.53 | 82.5134 | 7.023902 |
| 90.32977 | 40.64093 | 118.7493 | 127.0067 | 32.83026 | 103.9999 | 127.0067 | 158.9965 | 8.3256 |
| 60.4811 | 55.6148 | 102.8575 | 107.9831 | 53.08231 | 124.7128 | 107.9831 | 76.27457 | 33.6964 |
| 57.38832 | 64.94501 | 92.07208 | 94.10521 | 63.21226 | 130.2821 | 94.10521 | 107.4309 | 33.74076 |
| 95.29474 | 50.08331 | 127.9532 | 133.4391 | 81.17294 | 114.8864 | 133.4391 | 71.57614 | 27.57516 |
|  | 55.68761 |  |  | 75.35588 |  |  | 202.8471 |  |
|  | 61.64294 |  |  | 83.07431 |  |  | 156.5757 |  |
|  | 58.07758 |  |  | 74.25885 |  |  | 170.8763 |  |

| AP2-18 (250 µM) | | | AP2-18 (500 µM) | | | AP2-18 (1000 µM) | | |
|---|---|---|---|---|---|---|---|---|
| | | | | Incubation time: | | | | |
| 2 hours | 3 hours | 4 hours | 2 hours | 3 hours | 4 hours | 2 hours | 3 hours | 4 hours |
| 97.70197 | 86.93302 | 7.087759 | 12.85666 | 102.5418 | 6.022839 | 96.31454 | 92.46767 | 6.315399 |
| 86.78668 | 101.2448 | 6.581629 | 12.73516 | 125.9215 | 6.335878 | 83.65123 | 93.28389 | 6.00236 |
| 91.72502 | 79.69885 | 5.92922 | 16.03522 | 67.09776 | 6.645992 | 82.62045 | 87.84988 | 5.891187 |
| 133.2414 | 62.45917 | 7.339921 | 53.68466 | 33.03933 | 7.159339 | 98.18683 | 39.73278 | 7.607033 |
| 62.65508 | 60.17248 | 6.990043 | 42.01039 | 31.45498 | 7.629605 | 107.1891 | 38.73971 | 8.758245 |
| 106.5847 | 62.3481 | 6.519776 | 55.46601 | 38.58617 | 6.692834 | 53.90733 | 37.67804 | 7.362494 |
| 64.28761 | 33.55548 | 32.02563 | 60.63971 | 68.87704 | 42.87827 | 80.38594 | 45.15162 | 38.08773 |
| 96.80148 | 37.88737 | 32.79448 | 70.31457 | 42.18594 | 32.5727 | 46.20671 | 47.25092 | 34.19911 |
| 131.2186 | 49.01699 | 31.10892 | 124.24 | 58.38054 | 25.10596 | 97.83241 | 41.05298 | 25.29818 |
|  | 32.64986 |  |  | 49.61473 |  |  | 50.59423 |  |
|  | 47.7341 |  |  | 46.3628 |  |  | 59.84067 |  |
|  | 52.74912 |  |  | 69.55727 |  |  | 82.36907 |  |

FIGS. 8 and 9 indicate a time dependent increase in PpIX levels with all three PpIX-prodrugs investigated. It is clear that although the addition of the iron chelator CP94 (3) to the ALA or MAL incubation period improved PpIX levels, this was outperformed by the combinational iron chelating PpIX-prodrug AP2-18 (8) (with four hours incubation of 1000 µM AP2-18 (8) in A431 human squamous epithelial carcinoma cells producing statistically significant higher PpIX levels than any other treatment parameters investigated). It should also be noted that the lowest dose of AP2-18 (8) (250 µM) at the shortest incubation time (2 hours) investigated also produced more PpIX than the highest doses of ALA or MAL (1000 µM) employed at the longest incubation time (4 hours). Importantly the increased PpIX accumulation observed with AP2-18 (8) was also translated on irradiation (FIGS. 10 and 11) into statistically significant increases in cell kill (when compared with that produced by either ALA or MAL) with the greatest cytotoxicity being produced at 4 hours.

The invention claimed is:
1. A compound of formula (I) or any salt thereof:

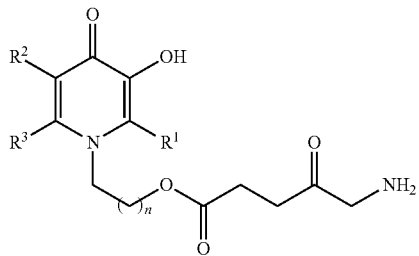

(I)

wherein
$R^1$ is a $C_1$-$C_6$ alkyl group,
$R^2$ is H or a $C_1$-$C_6$ alkyl group,
$R^3$ is H or a $C_1$-$C_6$ alkyl group, and
n is an integer from 0 to 5.

2. The compound according to claim 1 which is a salt of formula (Ia) or a salt of formula (Ib):

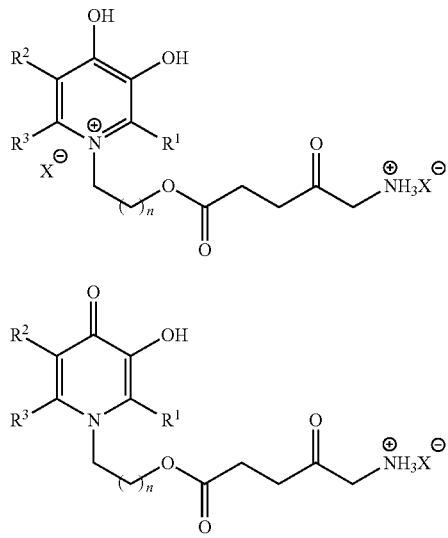

wherein
$R^1$, $R^2$, $R^3$ and n are as defined in claim 1; and
each $X^-$is independently selected from monovalent counterions.

3. The compound according to claim 2, wherein $X^-$ is $Cl^-$.
4. The compound according to claim 1, wherein $R^1$ is ethyl, $R^2$ and $R^3$ are H, and n is 1.
5. The compound according to claim 1 which is a salt of formula (Ic):

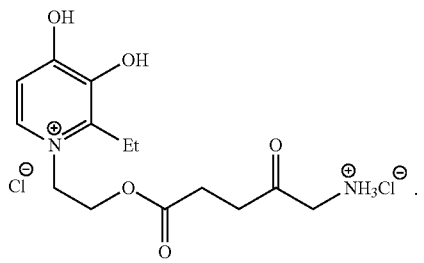

6. A pharmaceutical composition comprising the compound according to claim 1 and a pharmaceutically acceptable carrier.

7. The pharmaceutical composition according to claim 6, wherein the compound is a salt of formula (Ic):

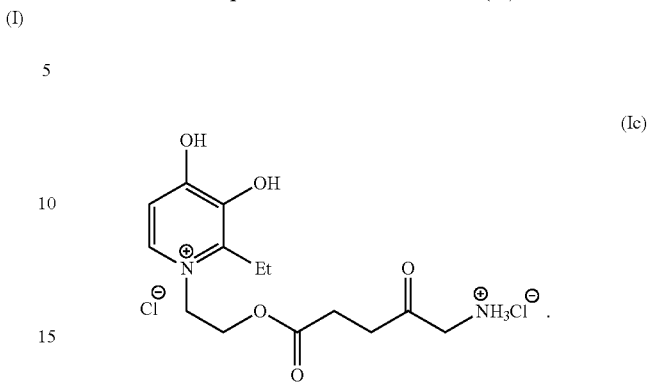

8. A process for making the compound according to claim 1, the method comprising the step of:
(a) reacting a compound of formula (II) with a compound of formula (III) via an esterification reaction to form a compound of formula (IV);
in accordance with the following reaction scheme:

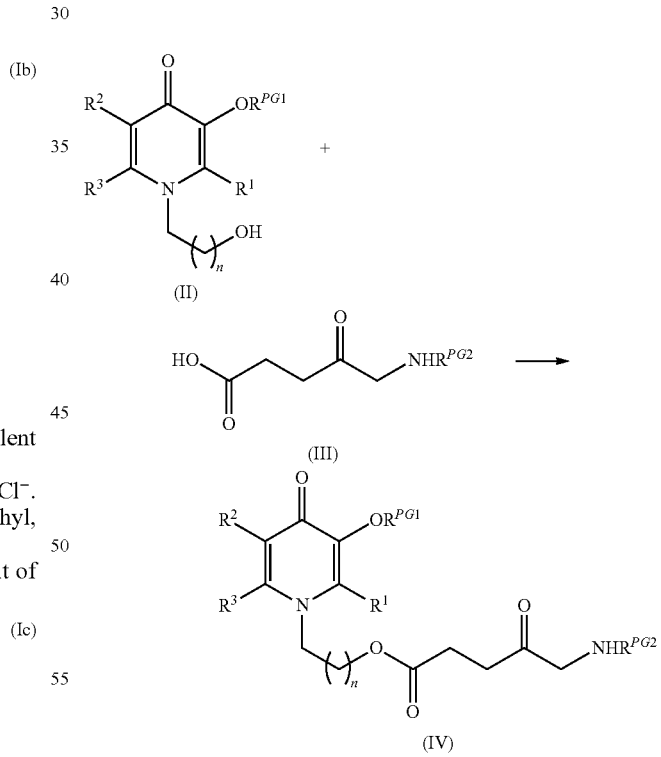

wherein
$R^1$, $R^2$, $R^3$ and n are as defined in claim 1; and
$R^{PG1}$ and $R^{PG2}$ are protecting groups.

9. The process according to claim 8, further comprising the step of:
(b1) deprotecting the compound of formula (IV) to give a compound of formula (I);

in accordance with the following reaction scheme:

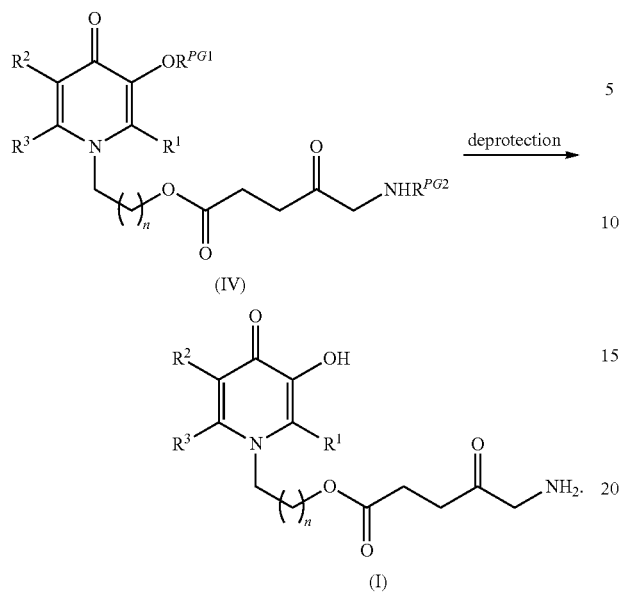

10. The process according to claim 8, further comprising the step of:

(b2) deprotecting the compound of formula (IV) in the presence of acid $H^+X^-$ to give a salt of formula (Ia);

in accordance with the following reaction scheme:

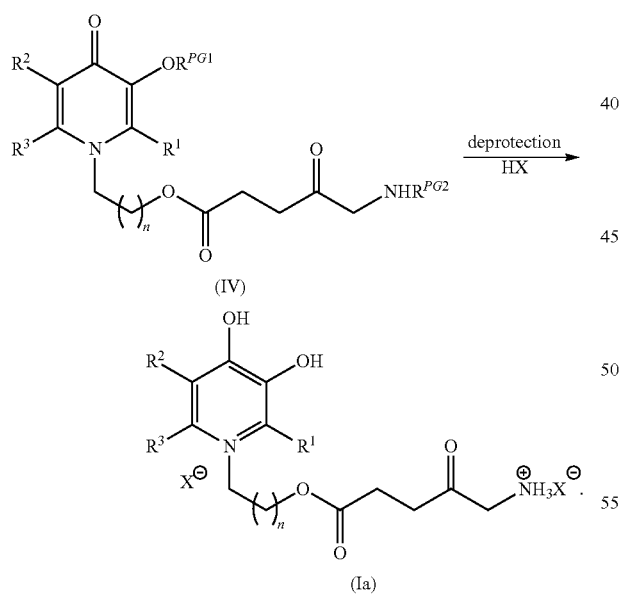

11. The process according to claim 8, further comprising the step of:

(b3) deprotecting the compound of formula (IV) in the presence of acid $H^+X^-$ to give a salt of formula (Ib);

in accordance with the following reaction scheme:

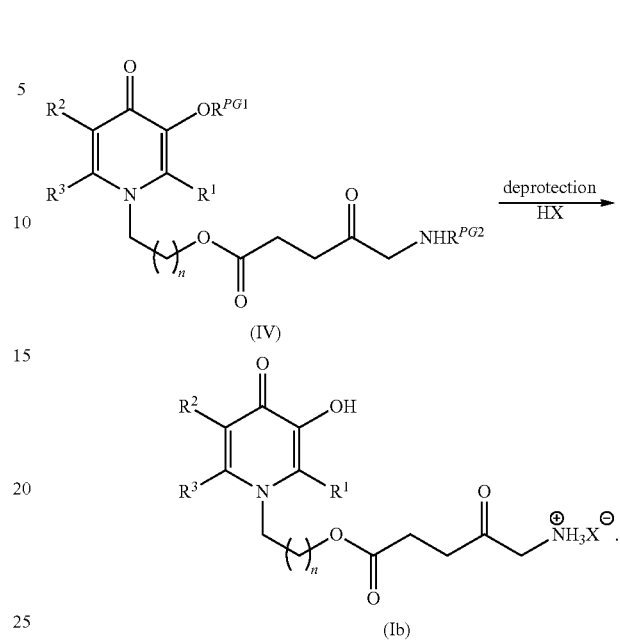

12. A method for treating or assisting the treatment of a proliferative, skin, inflammatory, or infectious condition in a subject in need thereof by photodynamic therapy, the method comprising:

(a) administering to the subject a compound of formula (I) or any salt thereof:

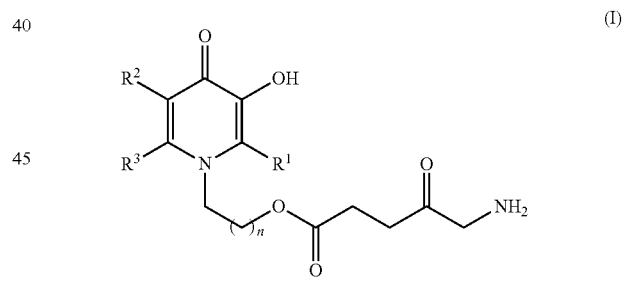

wherein $R^1$ is a $C_1$-$C_6$ alkyl group, $R^2$ is H or a $C_1$-$C_6$ alkyl group, $R^3$ is H or a $C_1$-$C_6$ alkyl group, and n is an integer from 0 to 5;

and (b) exposing a region of the subject containing the compound to light, thereby treating the subject.

13. The method according to claim 12, wherein the compound of formula (I) is a salt of formula (Ia) or a salt of formula (Ib):

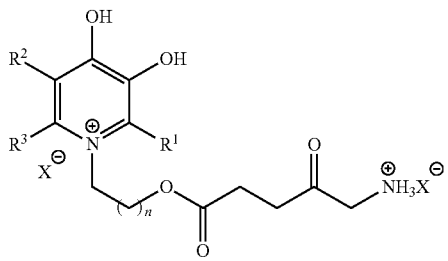

wherein
R¹, R², R³ and n are as defined in claim 12; and
each X⁻ is independently selected from monovalent counterions.

14. The method according to claim 13, wherein X⁻ is Cl⁻.

15. The method according to claim 12, wherein R¹ is ethyl, R² and R³ are H, and n is 1.

16. The method according to claim 12, wherein the subject is a human or an animal.

17. The method according to claim 12, wherein the proliferative condition is cancer.

18. The method according to claim 17, wherein the cancer is a skin cancer or an internal cancer.

19. The method according to claim 17, wherein the cancer is leukemia and the treatment comprises bone marrow purging.

20. The method according to claim 12, wherein the skin, inflammatory, or infectious condition is scleroderma, lichen sclerosus, psoriasis, warts, chronic wounds, acne, a microbial infection, a viral infection, a parasitic infestation, or rheumatoid arthritis.

21. The method according to claim 12, wherein the condition is cosmetic.

22. The method according to claim 12, wherein the compound is a salt of formula (Ic):

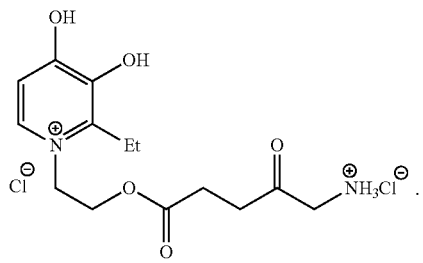

23. The method according to claim 22, wherein the subject is a human or an animal.

24. The method according to claim 23, wherein the proliferative condition is cancer.

25. The method according to claim 24, wherein the cancer is a skin cancer or an internal cancer.

* * * * *